(12) United States Patent
Vriezen

(10) Patent No.: US 9,622,430 B2
(45) Date of Patent: Apr. 18, 2017

(54) SOLANUM LYCOPERSICUM PLANTS HAVING NON-TRANSGENIC ALTERATIONS IN THE ACS4 GENE

(71) Applicant: NUNHEMS B.V., AC Nunhem (NL)

(72) Inventor: Willem Hendrik Vriezen, BM Haelen (NL)

(73) Assignee: NUNHEMS B.V., Nunhem (NL)

( * ) Notice: Subject to any disclaimer, the term of this patent is extended or adjusted under 35 U.S.C. 154(b) by 0 days.

(21) Appl. No.: 14/430,971

(22) PCT Filed: Sep. 25, 2013

(86) PCT No.: PCT/EP2013/069985
§ 371 (c)(1),
(2) Date: Mar. 25, 2015

(87) PCT Pub. No.: WO2014/049002
PCT Pub. Date: Apr. 3, 2014

(65) Prior Publication Data
US 2015/0237816 A1 Aug. 27, 2015

(30) Foreign Application Priority Data
Sep. 28, 2012 (EP) .................................... 12186606

(51) Int. Cl.
*A01H 5/08* (2006.01)
*C12N 15/82* (2006.01)
*C12N 9/88* (2006.01)
*A01H 1/02* (2006.01)
*A23L 19/00* (2016.01)

(52) U.S. Cl.
CPC ................ *A01H 5/08* (2013.01); *A01H 1/02* (2013.01); *A23L 19/00* (2016.08); *C12N 9/88* (2013.01); *C12N 15/8249* (2013.01); *A23V 2002/00* (2013.01)

(58) Field of Classification Search
None
See application file for complete search history.

(56) References Cited

U.S. PATENT DOCUMENTS 5,723,766 A 3/1998 Theologis et al.
8,099,245 B2 * 1/2012 Minoprio .................. C12N 9/90
435/4

FOREIGN PATENT DOCUMENTS

| EP | 1963505 B1 | 8/2012 |
|---|---|---|
| WO | WO 97/01952 A1 | 1/1997 |
| WO | WO 2005/016504 A2 | 2/2005 |
| WO | WO 2006/016504 A1 | 2/2006 |
| WO | WO 2007/044043 A2 | 4/2007 |

OTHER PUBLICATIONS

Lincoln et al, J. Biol. Chem., 1993, vol. 268, No. 26, pp. 1942-1943.*
Tarun and Theologist, The Journal of Biological Chemistry, 1998, vol. 273, No. 20, pp. 12509-12514.*
Capitani et al, Journal of Molecular Biology, 1999, vol. 294, pp. 745-756.*
TILLING, http://tilling.ucdavis.edu/index.php/Tomato_Tilling, last accessed Jul. 29, 2015, pp. 1-3.*
Alexander et al., "Ethylene biosynthesis and action in tomato: a model for climacteric fruit ripening", Journal of Experimental Botany, 2002, vol. 53, No. 377, pp. 2039-2055.
Barry et al., "The Regulation of 1-Aminocyclopropane-1-Carboxylic Acid Synthase Gene Expression during the Transition from System-1 to System-2 Ethylene Synthesis in Tomato", Plant Physiology, 2000, vol. 123, pp. 979-986.
Bui et al., Postharvest Ripening Characterization of Greenhouse Tomatoes, International Journal of Food Properties, 2010, vol. 13, pp. 830-846.
Clement et al., "Nondestructive Measurement of Fresh Tomato Lycopene Content and Other Physicochemical Characteristics Using Visible—NIR Spectroscopy", J. Agric. Food Chem., 2008, vol. 56, pp. 9813-9818.
Comai et al., "Efficient discovery of DNA polymorphisms in natural populations by Ecotilling", Plant J, 2004, vol. 37, pp. 778-786.
Cristecu et al., "Laser-based systems for trace gas detection in life sciences", Appl. Phys., 2008, B 92, pp. 343-349.
European Search Report issued in European Patent Application No. 1286606 dated Feb. 8, 2013.
Fish et al., "A quantitative assay for lcyopene that utilizes reduced volumes of organic solvents". J. Food Compos. Anal., 2002, vol. 15, pp. 309-317.
Henikoff et al., "Amino acid substitution matrices from protein blocks", PNAS, 1992, vol. 89, pp. 10915-10919.
Henikoff et al., "TILLING. Traditional Mutagenesis Meets Functional Genomics", Plant Physiology, 2004, vol. 135, pp. 630-636.
International Search Report and Written Opinion issued in International Patent Application No. PCT/EP2013/069985 dated Dec. 17, 2013.
Lincoln et al., "LE-ACS4, a Fruit Ripening and Wound-Induced 1-Aminocyclopropane-1-carboxlate Synthase Gene of Tomato (*Lycopersicon esculentum*)", The Journal of Biological Chemistry, 1993, vol. 268, No. 26, pp. 19422-19430.
Martinez-Madrid et al., "Polyamine Levels and Ethylene Production in Tomato Fruit Development and Ripening", Acta Horticulturae, 1995, vol. 412, pp. 463-469.

(Continued)

Primary Examiner — Eileen B O Hara
(74) Attorney, Agent, or Firm — Arent Fox LLP

(57) ABSTRACT

The present invention relates to cultivated plant of the species *Solanum lycopersicum* comprising an ACS4 allele having one or more mutations, said mutations resulting in production of a mutant acs4 protein having loss of-function acs4 protein or reduced function compared to wild type Acs4 protein.

25 Claims, 7 Drawing Sheets

(56) References Cited

OTHER PUBLICATIONS

Minoia et al., "A New Mutant Genetic Resource for Tomato Crop Improvement by TILLING Technology", BMC Research Notes, 2010, 3:69, pp. 1-8.

Mutschler et al, "Tomato Fruit Quality and Shelf Life in Hybrids Heterozygous for the alc Ripening Mutant", Hortscience, 1992, vol. 27, No. 4, pp. 352-355.

Rigola et al., "High Throughput Detection of Induced Mutations and Natural Variation Using KeyPoingTM Technology", PloS One, Mar. 2009, vol. 4, Issue 3, e4761, pp. 1-9.

Stearns et al., "Transgenic Plants with Altered Ethylene Biosynthesis or Perception", Biotechnology Advances 2003, vol. 21, pp. 193-210.

Tarun et al., "Complementation Analysis of Mutants of 1-Aminocyclopropane-1-carboxylate Synthase Reveals the Enzyme is a Dimer with Shared Active Sites", The Journal of Biological Chemistry, 1998, vol. 273, No. 20, pp. 12509-12514.

Till et al., "Discovery of chemically induced mutations in rice by TILLING", BMC Plant Biology, 2007, vol. 7, No. 19, pp. 1-12.

Till et al., "A protocol for TILLING and Ecotilling in plants and animals", Nature Protocols 2006, vol. 1, No. 5, pp. 2465-2477.

Till et al., "Discovery of induced point mutations in maize genes by TILLING", BMC Plant Biol, 2004, vol. 4, No. 12, pp. 1-8.

Till et al., "High-Throughput TILLING for Arabidopsis", Methods Mol Biol, 2006, vol. 323, pp. 127-135.

Tsuchisaka et al., "A Combinatorial Interplay Among the 1-Aminocyclopropane-1-Carboxylate Isoforms Regulates Ethylene Biosynthesis in Arabidopsis thaliana", The Genetics Society of America, 2009, vol. 183, pp. 979-1003.

U.S. Dept of Agriculture, US standards for grades of fresh tomatoes, U.S. Dept Agr. Mktg. Serv.,.Washington D.C, 1973, pp. 1-10.

Yokotani et al., "Ripening-associated Ethylene Biosynthesis in Tomato Fruit is Autocatalytically and Developmentally Regulated", Journal of Experimental Botany, 2009, vol. 60, No. 12, pp. 3433-3442.

Capitani et al. (1999) *Journal of Molecular Biology* 194: 745-756.

\* cited by examiner

Figure 4

Small domain

ACS4_WT_ID1       MDLETSEISN YKSSVVLSKL ASNEQHGENS PYFDGWKAYD NDPFHLVNNL 50

ACS4_2477_ID2     MDLETSEISN YKSSVVLSKL ASNEQHGENS PYFDGWKAYD NDPFHLVNNL

ACS4_4043_ID3     MDLETSEISN YKSSVVLSKL ASNEQHGENS PYFDGWKAYD NDPFHLVNNL

ACS4_4222_ID4     MDLETSEISN YKSSVVLSKL ASNEQHGENS PYFDGWKAYD NDPFHLVNNL

ACS4_4303_ID5     MDLETSEISN YKSSVVLSKL ASNEQHGENS PYFDGWKAYD NDPFHLVNNL

ACS4_4691_ID6     MDLETSEISN YKSSVVLSKL ASNEQHGENS PYFDGWKAYD NDPFHLVNNL

ACS4_5251_ID7     MDLETSEISN YKSSVVLSKL ASNEQHGENS PYFDGWKAYD NDPFHLVNNL

Large domain

ACS4_WT_ID1       NGVIQMGLAE NQLSVDLIEE WIKRNPKASI CTNDGIESFR RIANFQDYHG 100

ACS4_2477_ID2     NGVIQMGLAE NQLSVDLIEE WIKRNPKASI CTNDGIESFR RIANFQDYHG

ACS4_4043_ID3     NGVIQMGLAE NQLSVDLIEE WIKRNPKASI CTNDGIESFR RIANFQDYHG

ACS4_4222_ID4     NGVIQMGLAE NQLSVDLIEE WIKRNPKASI CTNDGIESFR RIANFQDYHG

ACS4_4303_ID5     NGVIQMGLAE NQLSVDLIEE WIKRNPKASI CTNDGIESFR RIANFQDYHG

ACS4_4691_ID6     NGVIQMGLAE NQLSVDLIEE WIKRNPKASI CTNDGIESFR RIANFQDYHG

ACS4_5251_ID7     NGVIQMGLAE NQLSVDLIEE WIKRNPKASI CTNDGIESFR RIANFQDYHG

ACS4_WT_ID1       LPEFTNAIAK FMEKTRGGKV KFDAKRVVMA GGATGANETL ILCLADPGDA 150

ACS4_2477_ID2     LPEFTNAIAK FMEKTRGGKV KFDAKRVVMA GGATGANETL ILCLADPGDA

ACS4_4043_ID3     LPEFTNAIAK FMEKTRGGKV KFDAKRVVMA GGATGANETL ILCLADPGDA

ACS4_4222_ID4     LPEFTNAIAK FMEKTRGGKV KFDAKRVVMA GGATGANETL ILCLADPGDA

ACS4_4303_ID5     LPEFTNAIAK FMEKTRGGKV KFDAKRVVMA GGATGANETL ILCLADPGDA

ACS4_4691_ID6     LPEFTNAIAK FMEKTRGGKV KFDAKRVVMA GGATGANETL ILCLADPGDA

ACS4_5251_ID7     LPEFTNAIAK FMEKTRGGKV KFDAKRVVMA GGATGANETL ILCLADPGDA

Figure 4 (Continued)

```
ACS4_WT_ID1    FLVPTPYYPG FNRDLRWRSG VQLLPISCKS CNNFKITIEA IEEAYEKGQQ 200

ACS4_2477_ID2  FLVPTPYYPG FNRDLRWRSG VQLLPISCKS CNNFKITIEA IEEAYEKGQQ

ACS4_4043_ID3  FLVPTPYYPG FNRDLRWRSG VQLLPISCKS CNNFKITIEA IEEAYEKGQQ

ACS4_4222_ID4  FLVPTPYYPG FNRDLRWRSG VQLLPISCKS CNNFKITIEA IEEAYEKGQQ

ACS4_4303_ID5  FLVPTPYYPG FNRDLRWRSG VQLLPISCKS CNNFKITIEA IEEAYEKGQQ

ACS4_4691_ID6  FLVPTPYYPG FNRDLRWRSG VQLLPISCKS CNNFKITIEA IEEAYEKGQQ

ACS4_5251_ID7  FLVPTPYYPG FNRDLRWRSG VQLLPISCKS CNNFKITIEA IEEAYEKGQQ

ACS4_WT_ID1    ANVKIKGLIL TNPCNPLGTI LDRDTLKKIS TFTNEHNIHL VCDEIYAATV 250

ACS4_2477_ID2  ANVKIKGLIL TNPCNPLGTI LDRDTLKKIS TFTNEHNIHL VCDEIYAATV

ACS4_4043_ID3  ANVKIKGLIL TNPCNPLGTI LDRDTLKKIS TFTNEHNIHL VCDEIYAVTV

ACS4_4222_ID4  ANV*

ACS4_4303_ID5  ANVKIKGLIL TNPCNPLGTI LDRDTLKKIS TFTNEHNIHL VCDEIYAATV

ACS4_4691_ID6  ANVKIKGLIL TNPCNPLGTI LDRDTLKKIS TFTNEHNIHL VCDEIYAATE

ACS4_5251_ID7  ANVKIKGLIL TNPCNPLGTI LDRDTLKKIS TFTNEHNIHL VCDEIYAATV

ACS4_WT_ID1    FNSPKFVSIA EIINEDNCIN KDLVHIVSSL SKDLGFPGFR VGIVYSFNDD 300

ACS4_2477_ID2  FNSPKFVSIA EIINEDNCIN KDLVHIVSNL SKDLGFPGFR VGIVYSFNDD

ACS4_4043_ID3  FNSPKFVSIA EIINEDNCIN KDLVHIVSSL SKDLGFPGFR VGIVYSFNDD

ACS4_4222_ID4

ACS4_4303_ID5  FNSPKFVSIA EIINEDNCIN KDLVHIVSSL SKDLGFPGFR VGIVYSFNDD

ACS4_4691_ID6  FNSPKFVSIA EIINEDNCIN KDLVHIVSSL SKDLGFPGFR VGIVYSFNDD

ACS4_5251_ID7  FNSPKFVSIA EIINEDNCIN KDLVHIVSSL SKDLGFPGFR VGIVYSFNDD
```

Figure 4 (Continued)

```
                                                              Small domain
ACS4_WT_ID1      VVNCARKMSS FGLVSTQTQH LLAFMLSDDE FVEEFLIESA KRLRERYEKF  350

ACS4_2477_ID2    VVNCARKMSS FGLVSTQTQH LLAFMLSDDE FVEEFLIESA KRLRERYEKF

ACS4_4043_ID3    VVNCARKMSS FGLVSTQTQH LLAFMLSDDE FVEEFLIESA KRLRERYEKF

ACS4_4222_ID4

ACS4_4303_ID5    VVNCARKMSS FGLVSTQTQH FLAFMLSDDE FVEEFLIESA KRLRERYEKF

ACS4_4691_ID6    VVNCARKMSS FGLVSTQTQH LLAFMLSDDE FVEEFLIESA KRLRERYEKF

ACS4_5251_ID7    VVNCARKMSS FGLVSIQTQH LLAFMLSDDE FVEEFLIESA KRLRERYEKF

ACS4_WT_ID1      TRGLEEIGIK CLESNAGVYC WMDLRSLLKE ATLDAEMSLW KLIINEVKLN  400

ACS4_2477_ID2    TRGLEEIGIK CLESNAGVYC WMDLRSLLKE ATLDAEMSLW KLIINEVKLN

ACS4_4043_ID3    TRGLEEIGIK CLESNAGVYC WMDLRSLLKE ATLDAEMSLW KLIINEVKLN

ACS4_4222_ID4

ACS4_4303_ID5    TRGLEEIGIK CLESNAGVYC WMDLRSLLKE ATLDAEMSLW KLIINEVKLN

ACS4_4691_ID6    TRGLEEIGIK CLESNAGVYC WMDLRSLLKE ATLDAEMSLW KLIINEVKLN

ACS4_5251_ID7    TRGLEEIGIK CLESNAGVYC WMDLRSLLKE ATLDAEMSLW KLIINEVKLN

ACS4_WT_ID1      VSPGSSFNCS EVGWFRVCFA NIDDQTMEIA LARIRMFMDA YNNVNKNGVM  450

ACS4_2477_ID2    VSPGSSFNCS EVGWFRVCFA NIDDQTMEIA LARIRMFMDA YNNVNKNGVM

ACS4_4043_ID3    VSPGSSFNCS EVGWFRVCFA NIDDQTMEIA LARIRMFMDA YNNVNKNGVM

ACS4_4222_ID4

ACS4_4303_ID5    VSPGSSFNCS EVGWFRVCFA NIDDQTMEIA LARIRMFMDA YNNVNKNGVM

ACS4_4691_ID6    VSPGSSFNCS EVGWFRVCFA NIDDQTMEIA LARIRMFMDA YNNVNKNGVM

ACS4_5251_ID7    VSPGSSFNCS EVGWFRVCFA NIDDQTMEIA LARIRMFMDA YNNVNKNGVM
```

Figure 4 (Continued)

```
ACS4_WT_ID1      KNKHNGRGTT YDLTPQMGST MKMLLA

ACS4_2477_ID2    KNKHNGRGTT YDLTPQMGST MKMLLA

ACS4_4043_ID3    KNKHNGRGTT YDLTPQMGST MKMLLA

ACS4_4222_ID4

ACS4_4303_ID5    KNKHNGRGTT YDLTPQMGST MKMLLA

ACS4_4691_ID6    KNKHNGRGTT YDLTPQMGST MKMLLA

ACS4_5251_ID7    KNKHNGRGTT YDLTPQMGST MKMLLA
```

SOLANUM LYCOPERSICUM PLANTS HAVING NON-TRANSGENIC ALTERATIONS IN THE ACS4 GENE

CROSS-REFERENCE TO RELATED APPLICATIONS

This application is the U.S. National Phase of International Patent Application No. PCT/EP2013/069985, filed Sep. 25, 2013, which claims the benefit of priority to European Application No. 12186606.5, filed Sep. 28, 2012, the contents of each are hereby incorporated by reference in their entireties.

FIELD OF THE INVENTION

This invention relates to the field of plant biotechnology and plant breeding. Provided are *Solanum lycopersicum* plants comprising an acs4 allele having one or more mutations, said mutations resulting in production of a mutant acs4 protein having loss-of-function acs4 protein or reduced activity compared to wild type Acs4 protein. The invention provides plants the fruits of which show a lower ethylene production and/or slower fruit ripening and/or a longer shelf life compared to *Solanum lycopersicum* being homozygous for the wild type Acs4 allele. In addition, the invention provides tomato fruit, seeds, pollen, plant parts, and progeny of the *Solanum lycopersicum* plants of the invention. Food and food products comprising or consisting of fruits of the plants of the invention are provided too.

The invention further provides an endogenous acs4 gene and acs4 protein encoded by said gene, having at least one human-induced non-transgenic mutation.

In another embodiment methods for making tomato plants comprising one or more mutant acs4 alleles in their genome are provided herein.

BACKGROUND OF THE INVENTION

Breeding of *Solanum lycopersicum* aims at the production of commercial varieties optimally adapted to growing and storage conditions. A challenge breeders are facing is finding an improved balance between fruit firmness post-harvest and consumer desires in terms of taste, texture and colour. These consumer desires relate strongly to fruit ripening. Fruit ripening is a complex developmental process responsible for the transformation of the seed-containing organ into a tissue attractive to seed dispersers and agricultural consumers. The changes associated with fruit ripening, in particular post-harvest softening, limit the shelf life of fresh tomatoes.

For tomato fruit growth and development, a number of consecutive phases can be discerned: floral development, pollination, then early fruit development takes place which is characterised by a high frequency of cell division and the fruit is rapidly increasing in size mainly due to cell expansion. At the end of the third phase the fruit reaches the mature green stage. During the fourth phase, fruit ripening takes place which is characterised by a change in colour and flavour as well as fruit firmness and texture.

The build-up of the characteristic red colour of the tomato fruit is caused by the accumulation of lycopene and carotene. In general, different colouration phases are distinguished: mature green, breaker, pink and red. At the breaker stage, the typical red pigmentation initiates. Red ripe stage or red ripe harvested fruit stage is the stage where the fruit has reached its mature colour on the major part of the fruit.

In addition to the colour changes, during fruit ripening enzymatic activity leads to degradation of the middle lamellar region of the cell walls which leads to cell loosening which is manifested as softening and loss of texture of the fruit. Softening of the fruit is often measured as external resistance to compression which can be quantified for example by a penetrometer.

Modification of single genes known to be involved in ripening has not yet resulted in a fruit with normal ripening but minimal tissue softening.

Ripening and senescence in climacteric fruits such as tomatoes are promoted by ethylene. Ethylene is autocatalytic for its own biosynthesis through increases in 1-Aminocyclopropane-1-carboxylic acid (ACC) synthase (ACS) and ACC oxidase (ACO). ACS is also referred to as 1-aminocyclopropane-1-carboxylate synthase; Le-ACS; or S-adenosyl-L-methionine methylthioadenosine-lyase. An increase in the amount of ACS and ACO thus leads to an increased conversion of L-methionine into ethylene. At least eight ACS genes (LEACS1A, LEACS1B, and LEACS2-7) have been identified in tomato (Alexander et. al., Journal of Experimental Botany, Vol 53, No 377, pp 2039-2055, 2002) and each ACS has a different expression pattern.

ACC synthase (ACS) is an enzyme that catalyzes the synthesis of 1-aminocyclopropane-1-carboxylic acid (ACC) from S-Adenosyl methionine. ACC is then converted into ethylene catalyzed by ACO. The biosynthesis of ethylene is for example described by Stearns and Glick (Biotechnology Advances 2003, vol 21 pp 193-210), which is enclosed by reference.

ACS belongs to the α-family of pyridoxal-5'-phosphate (PLP) dependent enzymes and shares a modest level of similarity with other members of this family like aspartate amino-transferase (AATase and tyrosine aminotransferase (TATase). The structure of ACS from various sources has been described by Capitani et al. In a sequence alignment of eight ACS proteins (*Malus domestica, Phaseolus aureus, Solanum tuberosum, Pelargonium hortorum, Nicotiana tabacum, Cucumis melo, Lycopersicon esculentum,* and *Brassica oleracea*) they describe conserved regions which are indicated in red and yellow in FIG. 1 in this Capitani publication. Three domains are defined: one large domain ranging from residue 52 to 318 and two small domains, ranging from residues 20 to 49 and 333 to 430. An helix α12 is defined connecting the large domain with the second small domain (Capitani et al., Journal of Molecular Biology, 1999, vol 294, pp 745-756).

Two systems have been proposed to operate in climacteric plants regulating ethylene production. The first is functional during normal vegetative growth (system 1); it is auto inhibitory and responsible for production of basal ethylene levels that are detected in all tissues including those in non-climacteric plants. System 1 continues during fruit development until a competence to fruit ripening is attained. Then a transition period is reached wherein LEACS1A and LEACS4 are activated resulting in an increased level of ethylene. This increased ethylene level induces the expression of LEACS2 which starts system 2 which is active during the ripening of climacteric fruit. In system 2, ethylene production is auto catalytic. This complexity of the ethylene regulation has been studied using antisense inhibition of LEACS2 in transgenic plants (Barry et al., Plant Physiology vol 123, pp 979-986, 2000).

WO2005/016504 discloses "stay green" plants, i.e. a plant phenotype whereby leaf senescence is delayed compared to a standard reference. It discloses plants with disrupted ACS2, ACS6, ASC7 genes which disruption inhibits the expression or activity of said ACS.

Yokotani et al describe transgenic tomatoes with all known LeEIL genes (Ethylene Insensitive Like genes) suppressed to study the regulatory mechanisms of ethylene biosynthesis (Yokotani et al, Journal of Experimental Botany, vol 60, pp 3433-3442, 2009).

There is thus a need for cultivated tomato plants with a modified ethylene production having a delayed ripening and/or longer shelf-life of the tomato fruits compared to wild type tomato plants.

SUMMARY OF THE INVENTION

It is, thus, an object of the invention to generate and identify cultivated plants of the species Solanum lycopersicum having fruits that have delayed ripening and/or a longer shelf-life of the fruits.

The invention thus relates to a cultivated plant of the species Solanum lycopersicum comprising an acs4 allele having one or more mutations, said mutations resulting in production of a mutant acs4 protein having loss-of-function acs4 protein or reduced activity compared to wild type Acs4 protein, but which comprises sufficient function to result in ripening of the tomato fruits to the red stage when the mutant allele is present in heterozygous or homozygous form.

GENERAL DEFINITIONS

The term "nucleic acid sequence" (or nucleic acid molecule) refers to a DNA or RNA molecule in single or double stranded form, particularly a DNA encoding a protein or protein fragment according to the invention. An "isolated nucleic acid sequence" refers to a nucleic acid sequence which is no longer in the natural environment from which it was isolated, e.g. the nucleic acid sequence in a bacterial host cell or in the plant nuclear or plastid genome.

The terms "protein" or "polypeptide" are used interchangeably and refer to molecules consisting of a chain of amino acids, without reference to a specific mode of action, size, 3-dimensional structure or origin. A "fragment" or "portion" of Acs4 protein may thus still be referred to as a "protein". An "isolated protein" is used to refer to a protein which is no longer in its natural environment, for example in vitro or in a recombinant bacterial or plant host cell.

The term "gene" means a DNA sequence comprising a region (transcribed region), which is transcribed into an RNA molecule (e.g. an mRNA or an RNAi molecule) in a cell, operably linked to suitable regulatory regions (e.g. a promoter). A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sites. A gene may be an endogenous gene (in the species of origin) or a chimeric gene (e.g. a transgene or cis-gene).

"Expression of a gene" refers to the process wherein a DNA region, which is operably linked to appropriate regulatory regions, particularly a promoter, is transcribed into an RNA, which is biologically active, i.e. which is capable of being translated into a biologically active protein or peptide (or active peptide fragment) or which is active itself (e.g. in posttranscriptional gene silencing or RNAi). The coding sequence may be in sense-orientation and encodes a desired, biologically active protein or peptide, or an active peptide fragment.

An "active protein" or "functional protein" is a protein which has protein activity as measurable in vitro, e.g. by an in vitro activity assay, and/or in vivo, e.g. by the phenotype conferred by the protein. A "wild type" protein is a fully functional protein, as present in the wild type plant. A "mutant protein" is herein a protein comprising one or more mutations in the nucleic acid sequence encoding the protein, whereby the mutation results in (the mutant nucleic acid molecule encoding) a "reduced-function" or "loss-of-function" protein, as e.g. measurable in vivo, e.g. by the phenotype conferred by the mutant allele.

A "reduced function acs4 protein" or "reduced activity acs4 protein" refers to a mutant acs4 protein which has a reduced catalytic activity in synthesizing ACC from S-Adenosyl methionine, leading to reduced ethylene synthesis compared to wild-type Acs4 protein. Said reduced catalytic activity of the acs4 protein affects the ripening behaviour of the fruits comprising such reduced function acs4 protein when the allele encoding the mutant protein is present in homozygous or heterozygous form in the tomato plant, i.e. delayed ripening and/or longer shelf-life of the fruits. Such a reduced function acs4 protein can be obtained by the transcription and translation of a "partial knockout mutant acs4 allele" which is, for example, a wild-type Acs4 allele, which comprises one or more mutations in its nucleic acid sequence. In one aspect, such a partial knockout mutant acs4 allele is a wild-type Acs4 allele, which comprises one or more mutations that preferably result in the production of an acs4 protein wherein at least one conserved and/or functional amino acid is substituted for another amino acid, such that the biological activity is significantly reduced but not completely abolished. However, other mutations, such as one or more non-sense, missense, splice-site or frameshift mutations in the tomato Acs4 allele may also result in reduced function acs4 protein and such reduced function proteins may have one or more amino acids replaced, inserted or deleted, relative to the wild type ACS4 protein. Such partial knockout mutant acs4 allele may also encode a dominant negative acs4 protein, which is capable of adversely affecting the biological activity of other Acs4 proteins within the same cell. Such a dominant negative acs4 protein can be an acs4 protein that is still capable of interacting with the same elements as the wild-type Acs4 protein, but that blocks some aspect of its function. Examples of dominant negative acs4 proteins are acs4 proteins that lack, or have modifications in specific amino acid residues critical for activation, but still contain their binding domain, such that not only their own biological activity is reduced or abolished, but that they further reduce the total acs4 activity in the cell by competing with wild type and/or partial knockout acs4 proteins present in the cell for binding sites. Mutant alleles can be either "natural mutant" alleles, which are mutant alleles found in nature (e.g. produced spontaneously without human application of mutagens) or "induced mutant" alleles, which are induced by human intervention, e.g. by mutagenesis.

A "loss-of-function acs4 protein" refers to a mutant acs4 protein which has essentially no catalytic activity in synthesising ACC from S-Adenosyl methionine compared to wild-type Acs4 protein, leading to reduced ethylene synthesis compared to wild type Acs4 protein. Said lack of catalytic activity synthesis affects the ripening behaviour of the fruits comprising such loss-of-function acs4 protein when the allele encoding the mutant protein is present in homozygous or heterozygous form in the tomato plant. Fruits of tomato plants homozygous for such a "loss-of-function acs4 protein" may still produce ethylene catalysed by other proteins (e.g. other Acs proteins like Acs1A). As a consequence, fruits of tomato plants homozygous for such a "loss-of-function acs4 protein" may still ripen, but ripening may be delayed and/or shelf life may be longer.

A "mutation" in a nucleic acid molecule coding for a protein is a change of one or more nucleotides compared to the wild type sequence, e.g. by replacement, deletion or insertion of one or more nucleotides. A "point mutation" is the replacement of a single nucleotide, or the insertion or deletion of a single nucleotide.

A "nonsense" mutation is a (point) mutation in a nucleic acid sequence encoding a protein, whereby a codon is changed into a stop codon. This results in a premature stop codon being present in the mRNA and in a truncated protein. A truncated protein may have reduced function or loss of function.

A "missense" or non-synonymous mutation is a (point) mutation in a nucleic acid sequence encoding a protein, whereby a codon is changed to code for a different amino acid. The resulting protein may have reduced function or loss of function.

A "splice-site" mutation is a mutation in a nucleic acid sequence encoding a protein, whereby RNA splicing of the pre-mRNA is changed, resulting in an mRNA having a different nucleotide sequence and a protein having a different amino acid sequence than the wild type. The resulting protein may have reduced function or loss of function.

A "frame-shift" mutation is a mutation in a nucleic acid sequence encoding a protein by which the reading frame of the mRNA is changed, resulting in a different amino acid sequence. The resulting protein may have reduced function or loss of function.

A mutation in a regulatory sequence, e.g. in a promoter of a gene, is a change of one or more nucleotides compared to the wild type sequence, e.g. by replacement, deletion or insertion of one or more nucleotides, leading for example to reduced or no mRNA transcript of the gene being made.

"Silencing" refers to a down-regulation or complete inhibition of gene expression of the target gene or gene family.

A "target gene" in gene silencing approaches is the gene or gene family (or one or more specific alleles of the gene) of which the endogenous gene expression is down-regulated or completely inhibited (silenced) when a chimeric silencing gene (or 'chimeric RNAi gene') is expressed and for example produces a silencing RNA transcript (e.g. a dsRNA or hairpin RNA capable of silencing the endogenous target gene expression). In mutagenesis approaches, a target gene is the endogenous gene which is to be mutated, leading to a change in (reduction or loss of) gene expression or a change in (reduction or loss of) function of the encoded protein.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous and, where necessary to join two protein encoding regions, contiguous and in reading frame so as to produce a "chimeric protein". A "chimeric protein" or "hybrid protein" is a protein composed of various protein "domains" (or motifs) which is not found as such in nature but which a joined to form a functional protein, which displays the functionality of the joined domains. A chimeric protein may also be a fusion protein of two or more proteins occurring in nature.

The term "food" is any substance consumed to provide nutritional support for the body. It is usually of plant or animal origin, and contains essential nutrients, such as carbohydrates, fats, proteins, vitamins, or minerals. The substance is ingested by an organism and assimilated by the organism's cells in an effort to produce energy, maintain life, or stimulate growth. The term food includes both substance consumed to provide nutritional support for the human and animal body.

The term "shelf life" or "post-harvest shelf life" designates the (average) length of time that a fruit is given before it is considered unsuitable for sale or consumption ('bad'). Shelf life is the period of time that products can be stored, during which the defined quality of a specified proportion of the goods remains acceptable under expected conditions of distribution, storage and display. Shelf life is influenced by several factors: exposure to light and heat, transmission of gases (including humidity), mechanical stresses, and contamination by things such as micro-organisms. Product quality is often mathematically modelled around the fruit firmness/softness parameter. Shelf-life can be defined as the (average) time it takes for fruits of a plant line to start to become bad and unsuitable for sale or consumption, starting for example from the first fruit of a plant entering breaker stage or turning stage or from the first fruit becoming fully red or from harvest. In one embodiment the mutants according to the invention have a shelf life that is significantly longer than the shelf life of wild type plants, for example the number of days from the first fruit being in breaker stage (or turning stage, pink stage, red stage or from harvest) up to the first fruit starting to become 'bad' and unsuitable for sale or consumption is significantly longer, e.g. at least 1, 2, 3, 4, 5, 6, 7, 8, 9, 10, or more, days longer than fruits of control plants (such as wild type Acs4/Acs4 plants), when plants are grown under the same conditions and fruits are treated the same way and kept under the same conditions. Thus, to determine the number of days required from a certain stage (e.g. from breaker stage or a later stage) to 'bad' stage, the day when the first fruit of the wild type control plant (gown under the same conditions as the mutant plants and being at the same developmental stage) enters a certain stage (e.g. breaker stage or a later stage) can, for example, be taken as the starting point (day 1) from when on periodically (at certain time intervals, e.g. after 1, 2, 3, 4, 5 or 6 days) the fruits are observed until the day that the first fruit has passed the fully ripe stage and becomes 'bad' (as determinable visually and/or through assessing fruit softness).

In this application the words "improved", "increased", "longer" and "extended" as used in conjunction with the word "shelf-life" are interchangeable and all mean that the fruits of a tomato plant according to the invention have on average, a longer shelf-life than the control fruits (Acs4/Acs4 fruits).

"Delayed ripening" means that the fruits of a tomato plant or plant line (e.g. a mutant) according to the invention require on average significantly more days to reach the red stage from the mature green, breaker, turning stage, and/or pink stages of tomato fruit ripening compared to wild type control fruits of plants homozygous for the wild type Acs4 allele (Acs4/Acs4). Delayed ripening can be measured on the plant and/or after harvest as days required for a certain percentage of fruits (e.g. 10%, 20%, 30%, 40%, 50%, 60%, 70%, 80%, 90% and/or 100% of fruits) to reach the red stage. A plant is said to have a delayed ripening phenotype if it takes at least 2, 3, 4, 5, 6, 7, 8, 9, 10, 11, 12, 13, 14 or 15 days longer for 10%, 20%, 30% 40%, 50%, 60%, 70%, 80%, 90% and/or 100% of fruits to reach the red stage than it takes for the wild type control fruits to develop the same percentage of red fruits. It is understood that each combination of above-cited number of days (i.e. 2, 3, 4, 5, 6, 7, 8, 9, 10, 11, 12, 13, 14 or 15) with each % of fruits to reach the red stage (i.e. 10%, 20%, 30% 40%, 50%, 60%, 70%, 80%, 90% and/or 100%) is enclosed herein, both for the delayed ripening to be measured on the plant and after harvest. For example if it takes at least 2 days longer for 10%, 20%, 30% 40%, 50%, 60%, 70%, 80%, 90% and/or 100% of fruits to reach the red stage than it takes for the wild type control fruits to develop the same percentage of red fruits. Another example of how delayed ripening can be measured on the plant and/or after harvest is it takes at least 2, 3, 4, 5, 6, 7, 8, 9, 10, 11, 12, 13, 14 or 15 days longer for 100% of fruits to reach the red stage than it takes for the wild type control fruits to develop the same percentage of red fruits. The day when the first fruit of the wild type control plant (grown under the same conditions as the mutant plants and being at the same developmental stage) enters a certain stage (e.g. breaker stage) can, for example, be taken as the starting point (day 1) from when on periodically (at certain time intervals (e.g. after 1, 2, 3, 4, 5 or 6 days) the number of fruits that are in breaker stage and the number of fruit that are in red stage are counted, both for the mutant plant line and control plants (see Examples).

As used herein, "reduced ethylene production" refers herein to statistically significant reduced amounts of ethylene being produced by tomato fruits according to the invention (compared to wild type Acs4/Acs4 fruits) during fruit ripening, e.g. at the pink stage and/or at the light red stage and/or at the red stage, as described in the Examples, and as measurable by real time ethylene measurements. In one embodiment, ethylene levels are significantly reduced throughout fruit ripening from pink stage through to red stage.

It is understood that comparisons between different plant lines involves growing a number of plants of a line (e.g. at least 5 plants, preferably at least 10 plants per line) under the same conditions as the plants of one or more control plant lines (preferably wild type plants) and the determination of statistically significant differences between the plant lines when grown under the same environmental conditions.

"Delay of breaker stage" refers to the mutants according to the invention requiring significantly more days than wild type controls for the first fruits and/or for all fruits to have entered breaker stage, e.g. at least 1 more day, preferably at least 2, 3, 4, 5, 6, 7, 8, 9, 10, 11 or 12 more days than the wild type control, when grown under the same conditions.

The "ripening stage" of a tomato fruit can be divided as follows: (1) Mature green stage: surface is completely green; the shade of green may vary from light to dark. (2) Breaker stage: there is a definite break in color from green to tannish-yellow, pink or red on not more than 10% of the surface; (3) Turning stage: 10% to 30% of the surface is not green; in the aggregate, shows a definite change from green to tannish-yellow, pink, red, or a combination thereof (4) Pink stage: 30% to 60% of the surface is not green; in the aggregate, shows pink or red color. (5) Light red stage: 60% to 90% of the surface is not green; in the aggregate, shows pinkish-red or red. (6) Red stage: More than 90% of the surface is not green; in the aggregate, shows red color.

"Sequence identity" and "sequence similarity" can be determined by alignment of two peptide or two nucleotide sequences using global or local alignment algorithms. Sequences may then be referred to as "substantially identical" or "essentially similar" when they are optimally aligned by for example the programs GAP or BESTFIT or the Emboss program "Needle" (using default parameters, see below) share at least a certain minimal percentage of sequence identity (as defined further below). These programs use the Needleman and Wunsch global alignment algorithm to align two sequences over their entire length, maximizing the number of matches and minimises the number of gaps. Generally, the default parameters are used, with a gap creation penalty=10 and gap extension penalty=0.5 (both for nucleotide and protein alignments). For nucleotides the default scoring matrix used is DNAFULL and for proteins the default scoring matrix is Blosum62 (Henikoff & Henikoff, 1992, PNAS 89, 1091510919). Sequence alignments and scores for percentage sequence identity may for example be determined using computer programs, such as EMBOSS (world wide web at ebi.ac.uk/Tools/psa/emboss_needle/). Alternatively sequence similarity or identity may be determined by searching against databases such as FASTA, BLAST, etc., but hits should be retrieved and aligned pairwise to compare sequence identity. Two proteins or two protein ebi.ac.uk/Tools/psa/e domains, or two nucleic acid sequences have "substantial sequence identity" if the percentage sequence identity is at least 90%, 95%, 98%, 99% or more (as determined by Emboss "needle" using default parameters, i.e. gap creation penalty=10, gap extension penalty=0.5, using scoring matrix DNAFULL for nucleic acids an Blosum62 for proteins). Such sequences are also referred to as 'variants' herein, e.g. other variants of mutant acs4 alleles and mutant acs4 proteins than the specific nucleic acid and protein sequences disclosed herein can be identified, which have the same effect on delayed ripening and/or longer shelf-life of the fruits comprising such variants.

The amino acid sequence alignment of five of the sequences given in FIG. 1 of Capitani et al. (Journal of Molecular Biology, 1999, vol 194, pp 745-756) (*Cucumis melo* Accession Q42668, *Pelargonium hortorum* Accession Q43810, *Brassica oleracea* Accession Q43747, *Phaseolus aureus* Accession Q41688, and *Solanum tuberosum* Accession Q43166) with the wild type *Solanum lycopersicum* ACS4 amino acid sequence as given in SEQ ID NO 1 (Le-ACS4) is shown in FIG. 1 of this application. This alignment reveals, see FIG. 1, that the conserved amino acids as indicated in yellow and red in FIG. 1 of Capitani et al. are also conserved in wild type *Solanum lycopersicum* ACS4 amino acid sequence. Note that the amino acid numbering in FIG. 1 of this application as indicated does not correspond to the numbering in FIG. 1 of Capitani et al.

The ACS4 "large domain" refers to amino acid residues from amino acid 65 to amino acid 327 of SEQ ID NO: 1 (see also FIG. 4). The ACS4 small domains refer to either amino acid residues 33 to 62 of SEQ ID NO: 1 (see FIG. 4) and/or from amino acid 339 to amino acid 438 of SEQ ID NO: 1 (see FIG. 4) of this application. The ACS4 catalytic centre is believed to be in the "large domain".

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one". It is further understood that, when referring to "sequences" herein, generally the actual physical molecules with a certain sequence of subunits (e.g. amino acids) are referred to.

As used herein, the term "plant" includes the whole plant or any parts or derivatives thereof, such as plant organs (e.g., harvested or non-harvested fruits, flowers, leaves, etc.), plant cells, plant protoplasts, plant cell or tissue cultures from which whole plants can be regenerated, regenerable or non-regenerable plant cells, plant calli, plant cell clumps, and plant cells that are intact in plants, or parts of plants, such as embryos, pollen, ovules, ovaries, fruits (e.g., harvested tissues or organs, such as harvested tomatoes or parts thereof), flowers, leaves, seeds, tubers, clonally propagated plants, roots, stems, cotyledons, hypocotyls, root tips and the like. Also any developmental stage is included, such as seedlings, immature and mature, etc.

A "plant line" or "breeding line" refers to a plant and its progeny. As used herein, the term "inbred line" refers to a plant line which has been repeatedly selfed.

"Plant variety" is a group of plants within the same botanical taxon of the lowest grade known, which (irrespective of whether the conditions for the recognition of plant breeder's rights are fulfilled or not) can be defined on the basis of the expression of characteristics that result from a certain genotype or a combination of genotypes, can be distinguished from any other group of plants by the expression of at least one of those characteristics, and can be regarded as an entity, because it can be multiplied without any change. Therefore, the term "plant variety" cannot be used to denote a group of plants, even if they are of the same kind, if they are all characterized by the presence of 1 locus or gene (or a series of phenotypical characteristics due to this single locus or gene), but which can otherwise differ from one another enormously as regards the other loci or genes.

"F1, F2, etc." refers to the consecutive related generations following a cross between two parent plants or parent lines. The plants grown from the seeds produced by crossing two plants or lines is called the F1 generation. Selfing the F1 plants results in the F2 generation, etc. "F1 hybrid" plant (or F1 seed) is the generation obtained from crossing two inbred parent lines. An "M1 population" is a plurality of mutagenized seeds/plants of a certain plant line or cultivar. "M2, M3, M4, etc." refers to the consecutive generations obtained following selfing of a first mutagenized seed/plant (M1).

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous).

The term "locus" (loci plural) means a specific place or places or a site on a chromosome where for example a gene or genetic marker is found. The ACS4 locus is thus the location in the genome where the ACS4 gene is found.

"Wild type allele" (WT) refers herein to a version of a gene encoding a fully functional protein (wild type protein). Such a sequence encoding a fully functional Acs4 protein is for example the wild type Acs4 cDNA (mRNA) sequence depicted in SEQ ID NO: 8, based on GenBank Accession M63490.1 or the wild type Acs4 genomic sequence depicted in SEQ ID NO: 15. The protein sequence encoded by this wild type Acs4 mRNA is depicted in SEQ ID NO: 1 and in SEQ ID NO: 15. It consists of 476 amino acids. Three domains have been mentioned to occur on the Acs4 protein i.e. a first small domain ranging from amino acid 33 to 62 of SEQ ID NO: 1, a "large domain", presumed to contain the catalytic centre of the protein (ranging from amino acid 65 to 327 of SEQ ID NO: 1 and a second small domain ranging from amino acid residue 339 to 438 of SEQ ID NO: 1 (see FIG. 4). Other fully functional Acs4 protein encoding alleles (i.e. alleles which confer ripening and ethylene production to the same extent as the protein of SEQ ID NO 1) may exist in other *Solanum lycopersicum* plants and may comprise substantial sequence identity with SEQ ID NO: 1, i.e. at least about 90%, 95%, 98%, 99%, 99.2%, 99.3%, 99.4%, 99.5%, 99.6%, 99.7% sequence identity with SEQ ID NO: 1. Such fully functional wild type Acs4 proteins are herein referred to as "variants" of SEQ ID NO: 1. Likewise the nucleotide sequences encoding such fully functional Acs4 proteins are referred to as variants of SEQ ID NO: 8 and SEQ ID NO: 15.

The following mutant acs4 alleles are exemplary of the reduced ethylene production and/or delayed-ripening and/or extended shelf-life conferring acs4 mutations identified according to the present invention. It is noted that nucleotide sequences referred to herein (SEQ ID NO: 8-14) are cDNA, i.e. coding DNA sequences, encoding the proteins of SEQ ID NO: 1-7. Obviously, when reference is made to these cDNA nucleotide sequences, it is understood that the cDNA is the coding region of the corresponding *Solanum lycopersicum* genomic acs4 sequence, which, however, additionally contains introns and therefore the nucleotides have different numbering. Thus, when reference is made to a tomato plant comprising an acs4 sequence according to e.g. any one of SEQ ID NO: 8-14, it is, therefore, understood that the tomato plant comprising the genomic acs4 sequence which comprises the coding DNA (cDNA), from which the mRNA of SEQ ID NO: 8-14 is transcribed (and which is in turn translated into protein). The mRNA has the same nucleotide sequence as the cDNA, accept that Thymine (t) is Uracil (u) in the mRNA. Further, when reference is made to a tomato plant comprising a nucleotide sequence encoding a protein according to the invention (such as a mutant protein of SEQ ID No: 2-7, or a different mutant), this encompasses different nucleotide sequences, due to the degeneracy of the genetic code. In one embodiment the plant comprises the genomic Acs4 sequence depicted in SEQ ID NO:15 or a genomic Acs4 sequence substantially identical thereto (e.g. having at least about 70%, 75%, 80%, 85%, 90%, 95%, 98%, 99%, 99.2%, 99.3%, 99.4%, 99.5%, 99.6%, 99.7% sequence identity with SEQ ID NO: 15), but with one or more mutations in said sequence, especially in the exons of said genomic sequence (exon 1 ranges from nucleotide 1 to 318; exon 2 ranges from nucleotide 796 to 955 and exon 3 ranges from nucleotide 1689 to 2638), causing reduced function or loss of function of the encoded mutant acs4 protein.

One exemplary mutant acs4 allele (mutant 2477, or Nun 2477) conferring reduced ethylene production and/or delayed ripening and/or extended shelf-life identified according to the present invention, comprises a mutation resulting in a serine (Ser or S) to asparagine (Asn or N) substitution at amino acid 279 in the encoded protein (SEQ ID NO: 2). The S279N mutation is within the large-domain of the ACS4 protein. The protein sequence of mutant 2477 is depicted in SEQ ID NO: 2. The amino acid substitution is due to a G to A mutation at nucleotide 836 of SEQ ID NO: 8 counting A in the ATG of the START CODON as nucleotide position 1. The mutant cDNA is depicted in SEQ ID NO: 9.

Another exemplary mutant acs4 allele (mutant 4043, or Nun 4043) conferring reduced ethylene production and/or delayed ripening and/or extended shelf-life identified according to the present invention, comprises a mutation resulting in a change from alanine (Ala or A) to valine (Val or V) at amino acid 248 in the encoded protein (SEQ ID NO: 3). The A248V mutation is within the large-domain of the ACS4 protein. The protein sequence of mutant 4043 is depicted in SEQ ID NO: 3. The amino acid substitution is due to a C to T mutation at nucleotide 743 of SEQ ID NO: 1, counting A in the ATG of the START CODON as nucleotide position 1. The mutant cDNA is depicted in SEQ ID NO: 10.

Still another exemplary mutant acs4 allele (mutant 4222, or Nun 4222) conferring reduced ethylene production and/or delayed ripening and/or extended shelf-life, identified according to the present invention, comprises a mutation resulting in a truncated protein of 203 amino acid residues during translation, whereas the wild type protein has 476 amino acid residues. The truncated protein sequence of mutant 4222 is depicted in SEQ ID NO: 4. The truncation is due to a change from A to T at nucleotide 610 of SEQ ID NO: 1 counting A in the ATG of the START CODON as nucleotide position 1. This A610T mutation in mutant 4222 results in a change from a codon for lysine (AAA) to a STOP-codon (TAA). The mutant cDNA is depicted in SEQ ID NO: 11.

Another exemplary mutant acs4 allele (mutant 4303 or Nun 4303) conferring reduced ethylene production and/or delayed ripening and/or extended shelf-life, identified according to the present invention, comprises a mutation resulting in a change from leucine (Leu or L) to phenylalanine (Phe or F) at amino acid 321 in the encoded protein. The L321F mutation is within the second small-domain of the ACS4 protein. The protein sequence of mutant 4303 is depicted in SEQ ID NO: 5. The amino acid substitution is due to a change from G to T at nucleotide 963 of SEQ ID NO: 1 counting A in the ATG of the START CODON as nucleotide position 1. The mutant cDNA is depicted in SEQ ID NO: 12.

Yet another exemplary mutant acs4 allele (mutant 4691, or Nun 4691) conferring reduced ethylene production and/or delayed ripening and/or extended shelf-life, identified according to the present invention, comprises a mutation resulting in a change from valine (Val or V) to glutamic acid (Glu or E) at amino acid 250 in the encoded protein. The V250E mutation is within the large-domain of the ACS4 protein. The protein sequence of mutant 4691 is depicted in SEQ ID NO: 6. The amino acid substitution is due to a change from T to A at nucleotide 749 of as shown in SEQ ID NO: 1 counting A in the ATG of the START CODON as nucleotide position 1. The mutant cDNA is depicted in SEQ ID NO: 13.

Another exemplary mutant acs4 allele (mutant 5251, or Nun 5251) conferring reduced ethylene production and/or delayed ripening and/or extended shelf-life, identified according to the present invention, comprises a mutation resulting in a change from threonine (Thr or T) to isoleucine (Ile or I) at amino acid 316 in the encoded protein. The T316I mutation is within the second small-domain of the ACS4 protein. The protein sequence of mutant 5251 is depicted in SEQ ID NO: 7. The amino acid substitution is due to a change from C to T at nucleotide 947 of SEQ ID NO: 1 counting A in the ATG of the START CODON as nucleotide position 1. The mutant cDNA is depicted in SEQ ID NO: 14.

"Mutant allele" refers herein to an allele comprising one or more mutations in the coding sequence (mRNA, cDNA or genomic sequence) compared to the wild type allele. Such mutation(s) (e.g. insertion, inversion, deletion and/or replacement of one or more nucleotide(s)) may lead to the encoded protein having reduced in vitro and/or in vivo functionality (reduced function) or no in vitro and/or in vivo functionality (loss-of-function), e.g. due to the protein e.g. being truncated or having an amino acid sequence wherein one or more amino acids are deleted, inserted or replaced. Such changes may lead to the protein having a different 3D conformation, being targeted to a different sub-cellular compartment, having a modified catalytic domain, having a modified binding activity to nucleic acids or proteins, etc.

"Wild type plant" and "wild type fruits" or "normal ripening" plants/fruits refers herein to a tomato plant comprising two copies of a wild type (WT) Acs4 allele (Acs4/Acs4) encoding a fully functional Acs4 protein (e.g. in contrast to "mutant plants", comprising a mutant acs4 allele). Such plants are for example suitable controls in phenotypic assays. Preferably wild type and/or mutant plants are "cultivated tomato plants". For example the cultivar Moneymaker is a wild type plant, as is cultivar Ailsa Craig, cultivar Tapa and many others.

"Tomato plants" or "cultivated tomato plants" are plants of the *Solanum lycopersicum*, i.e. varieties, breeding lines or cultivars of the species *Solanum lycopersicum*, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of a species. The so-called heirloom varieties or cultivars, i.e. open pollinated varieties or cultivars commonly grown during earlier periods in human history and often adapted to specific geographic regions, are in one aspect of the invention encompassed herein as cultivated tomato plants.

Wild relatives of tomato include *S. arcanum, S. chmielewskii, S. neorickii (=L. parviflorum), S. cheesmaniae, S. galapagense, S. pimpinellifolium, S. chilense, S. corneliomulleri, S. habrochaites (=L. hirsutum), S. huaylasense, S. sisymbriifolium, S. peruvianum, S. hirsutum* or *S. pennellii*.

"Average" refers herein to the arithmetic mean.

BRIEF DESCRIPTION OF THE SEQUENCE LISTING

SEQ ID NO: 1 shows the *Solanum lycopersicum* wild type, fully functional, ACS4 protein sequence as derived from the mRNA based on Genbank Accession number AAA34131.1 (encoded by the cDNA of GenBank Accession number M63490.1).

SEQ ID NO: 2 shows the *Solanum lycopersicum* mutant 2477 acs4 protein sequence.

SEQ ID NO: 3 shows the *Solanum lycopersicum* mutant 4043 acs4 protein sequence.

SEQ ID NO: 4 shows the *Solanum lycopersicum* mutant 4222 acs4 protein sequence.

SEQ ID NO: 5 shows the *Solanum lycopersicum* mutant 4303 acs4 protein sequence.

SEQ ID NO: 6 shows the *Solanum lycopersicum* mutant 4691 acs4 protein sequence.

SEQ ID NO: 7 shows the *Solanum lycopersicum* mutant 5251 acs4 protein sequence.

SEQ ID NO: 8 shows the *Solanum lycopersicum* wild type Acs4 cDNA based on Genbank Accession number M63490.1.

SEQ ID NO: 9 shows the *Solanum lycopersicum* mutant 2477 acs4 cDNA.

SEQ ID NO: 10 shows the *Solanum lycopersicum* mutant 4043 acs4 cDNA.

SEQ ID NO: 11 shows the *Solanum lycopersicum* mutant 4222 acs4 cDNA.

SEQ ID NO: 12 shows the *Solanum lycopersicum* mutant 4303 acs4 cDNA.

SEQ ID NO: 13 shows the *Solanum lycopersicum* mutant 4691 acs4 cDNA.

SEQ ID NO: 14 shows the *Solanum lycopersicum* mutant 5251 acs4 cDNA.

SEQ ID NO: 15 shows the *Solanum lycopersicum* wild type Acs4 genomic DNA.

BRIEF DESCRIPTION OF THE FIGURES

FIG. 4: Alignment of SEQ ID NO: 1-7. The Acs4 domains are also depicted (light gray), as are the mutations (in bold and underlined).

DETAILED DESCRIPTION OF THE INVENTION

Figure 1:
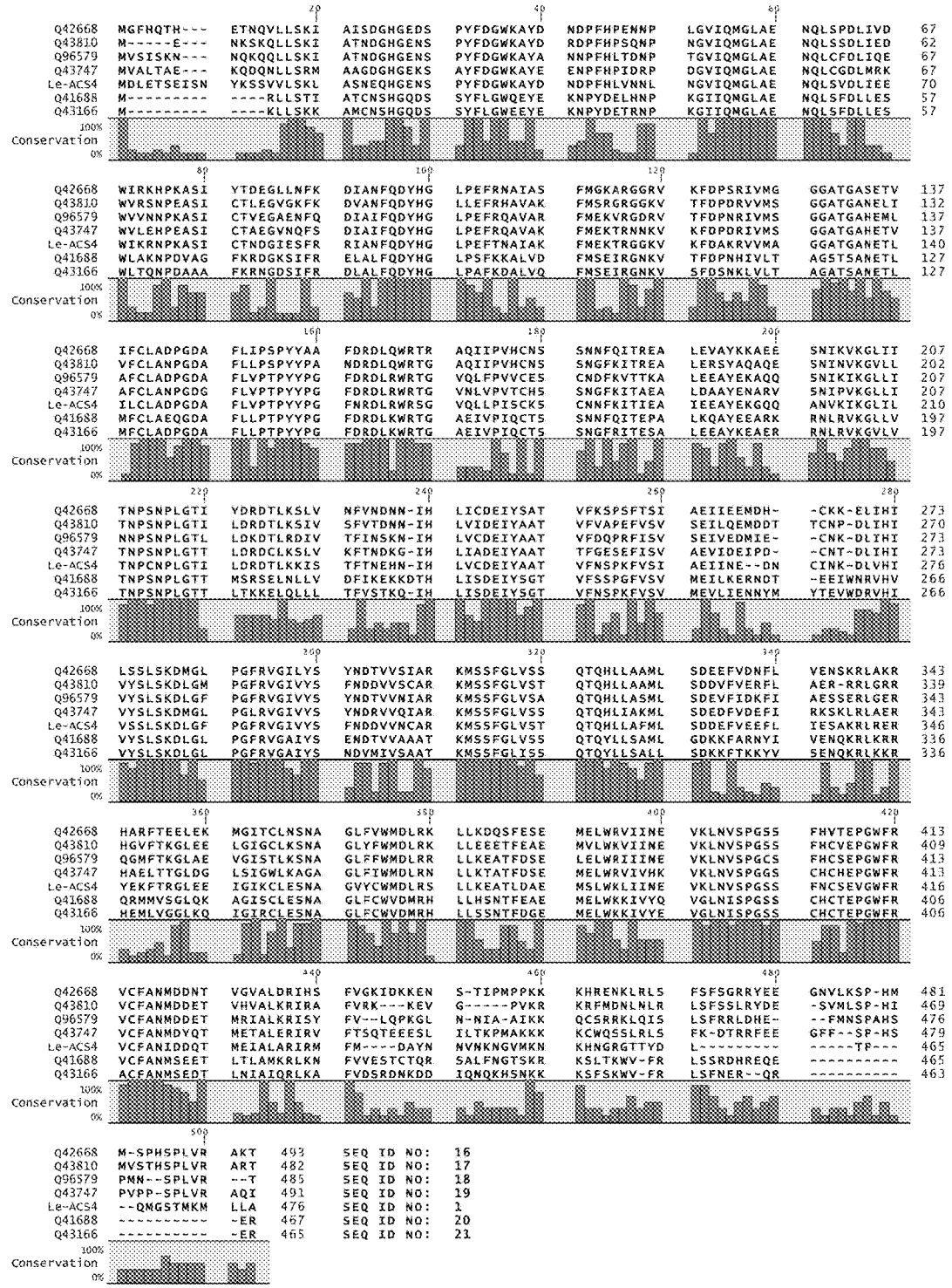
FIG. 1: In this graph an alignment of the amino acid sequence of 5 of the sequences given in FIG. 1 of Capitani et al. (Journal of Molecular Biology, 1999, vol 194, pp 745-756) (*Cucumis melo, Pelargonium hortorum, Brassica oleracea, Phaseolus aureus*, and *Solanum tuberosum*) with the wild type *Solanum lycopersicum* ACS4 amino acid sequence as given in SEQ ID NO 1 is shown.

The present invention discloses a cultivated plant of the species *Solanum lycopersicum* comprising an acs4 allele having one or more mutations, said mutations resulting in production of a mutant acs4 protein having loss-of-function and/or reduced function compared to wild type Acs4 protein.

The Acs4 protein sequence contains 3 domains: a "large domain" referring to amino acid residues 65 to 327 as indicated in FIG. 4 of this application and two small domains referring to amino acid residues 33 to 62 and 339 to 438, respectively as indicated in FIG. 4 of this application. The Acs4 catalytic centre is believed to be in the "large domain".

In one aspect the invention relates to a cultivated plant of the species *Solanum lycopersicum*, and/or parts thereof (e.g. fruits), comprising an acs4 allele having one or more mutations, said mutations resulting in production of a mutant acs4 protein having loss-of-function or reduced function compared to wild type Acs4 protein wherein said mutation or mutations result in reduced ethylene production and/or delayed fruit ripening and/or a longer shelf life compared to *Solanum lycopersicum* plants which are homozygous for the wild type fully functional Acs4 allele (Acs4/Acs4) (encoding a functional Acs4 protein of SEQ ID NO: 1 or a functional variant).

A *S. lycopersicum* plant encoding the protein of SEQ ID NO: 1 is for example cultivar UC82B, or others.

In one aspect, a functional variant of SEQ ID NO: 1 is the Acs4 allele encoding the protein of GenBank accession CAH56694, CAH56504, or CAH56693. A *S. lycopersicum* plant encoding a functional variant of SEQ ID NO: 1 is for example cultivar San Marzano Vesuvio, San Marzano Nano or Tondino.

In one aspect the invention relates to a cultivated plant of the species *Solanum lycopersicum*, and/or parts thereof (e.g. fruits), comprising an acs4 allele having one or more mutations, said mutations resulting in production of a mutant acs4 protein having loss-of-function acs4 protein or reduced function compared to wild type Acs4 protein wherein said mutation or mutations result in reduced ethylene production and/or delayed fruit ripening and/or a longer shelf life compared to *Solanum lycopersicum* plants which are homozygous for the wild type fully functional Acs4 allele (Acs4/Acs4) (encoding a functional Acs4 protein of SEQ ID NO: 1 or a functional variant), wherein the tomato plant does not comprise the Acs4 allele encoding the protein of Gen-Bank accession CAH56694, CAH56504, or CAH56693. In another aspect, the mutation or mutations in the plant of the invention result in reduced ethylene production compared to *Solanum lycopersicum* being homozygous for the wild type Acs4 allele.

In another aspect, the mutation or mutations in the plant of the invention result in delayed fruit ripening and/or a longer shelf life compared to *Solanum lycopersicum* being homozygous for the wild type Acs4 allele.

In yet another aspect, the invention relates to a cultivated plant of the species *Solanum lycopersicum* comprising an acs4 allele having one or more mutations resulting in a loss-of-function acs4 protein or reduced-function acs4 protein, wherein said mutation(s) are occurring in the "large domain", i.e. in the encoding part of amino acid region 65 to 327 of the wild type, functional Acs4 protein encoding, Acs4 allele, and said mutations resulting in production of a mutant acs4 protein having loss-of-function acs4 protein or reduced function compared to wild type Acs4 protein wherein said mutation or mutations result in reduced ethylene production and/or delayed fruit ripening and/or a longer shelf life compared to *Solanum lycopersicum* being homozygous for the wild type Acs4 allele. In a preferred aspect, the one or more mutations are one or more amino acid substitutions, deletions and/or insertions in the region of amino acid 241 to 251 of SEQ ID NO: 1 and/or in the region of amino acids 304 to 327; in another aspect the one or more mutations result in part or all of the large domain downstream of amino acid 200, 201, or 203 being absent or the mutations result in a truncated acs4 protein which lacks at least the second small domain and/or part of the large domain, e.g. a stop codon being present anywhere after nucleotide 600 of SEQ ID NO: 8.

In yet a further aspect, the invention relates to a *Solanum lycopersicum* plant comprising an acs4 allele encoding a loss-of-function acs4 protein or reduced-function acs4 protein, which protein comprises a functional "large-domain", i.e. the mutation leading to the reduced ethylene production and/or the delayed ripening and/or longer shelf life, lies outside the "large-domain". Thus, in one embodiment the mutant acs4 allele comprises one or more mutations in one or both of the small domains from amino acid 33 to 62 and/or 339 to 438 of SEQ ID NO:1, or of a variant of SEQ ID NO:1 which comprises a functional "large-domain", and further comprises (a nucleotide sequence encoding) at least one amino acid insertion, deletion or replacement in amino acids 33 to 62 and/or 339 to 438 of SEQ ID NO: 1, said at least one insertion, deletion or replacement leading to a reduced ethylene production and/or a delay in ripening and/or longer shelf life of the fruit of the tomato plant.

In one embodiment the mutation(s) causing the loss-of-function acs4 protein or reduced-function of the acs4 protein is/are in the "large-domain" of the wild type Acs4 protein i.e. which protein comprises functional "small-domains", thus in one embodiment one or more amino acids are inserted, deleted or replaced in amino acids 65 to 327 of SEQ ID NO: 1 or a variant of SEQ ID NO: 1. In another embodiment the mutation(s) causing the loss-of-function acs4 protein or reduced-function of the acs4 protein is/are in the C-terminus of the wild type Acs4 protein, thus in one embodiment one or more amino acids are inserted, deleted or replaced in amino acids 444 to 476 of SEQ ID NO: 1 (or a variant of SEQ ID NO: 1).

Thus, in one embodiment of the invention, the tomato plants according to the invention comprise an endogenous (non-transgenic) mutant acs4 allele, which encodes a loss-of-function acs4 protein or reduced-function mutant acs4 protein whereby the fruits of the plant do ripen to the red stage (preferably slower than plants homozygous for the wild type allele, encoding a fully functional Acs4 protein). In another embodiment of the invention, the tomato plants according to the invention comprise a human-induced non-transgenic mutant acs4 allele, which encodes a reduced-function mutant acs4 protein and/or a loss-of-function acs4 protein. In still another embodiment such mutant acs4 allele is derived from and/or generated in a cultivated tomato (e.g. a breeding line, variety or heirloom variety) or a wild relative of tomato. Such a human-induced mutation may for example be induced using targeted mutagenesis as described in EP1963505. Mutant acs4 alleles generated in wild relatives of tomato are then easily transferred into cultivated tomato by breeding.

In still another aspect, the invention relates to a plant according to the invention having an endogenous acs4 allele encoding a loss-of-function acs4 protein or reduced-function acs4 protein having substantial sequence identity to SEQ. ID NO: 1, or to a variant of SEQ ID NO: 1, wherein said protein comprising one or more amino acid replacements, deletions and/or insertions.

In yet another aspect, the invention relates to a plant of the invention comprising reduced ethylene production and/or delayed ripening and/or longer shelf-life than wild type (Acs4/Acs4) plants, due to said plants comprising an endogenous acs4 allele encoding a loss-of-function acs4 protein or reduced-function acs4 protein having substantial sequence identity to SEQ. ID NO: 2 or to SEQ. ID NO: 3, or to SEQ. ID NO: 4, or to SEQ. ID NO: 5 or to SEQ. ID NO: 6, or to SEQ. ID NO: 7. In a specific aspect, the invention relates to cultivated tomato plants comprising a acs4 allele as found in seed deposited under accession number NCIMB 42034, NCIMB 42037, NCIMB 42038, NCIMB 42039, or NCIMB 42041 in one or two copies, i.e. in homozygous or heterozygous form. In heterozygous form, the other allele may be a wild type Acs4 allele or another mutant acs4 allele, such as from any one of the other mutants provided herein, or any other mutant acs4 allele encoding for a loss-of-function acs4 protein or reduced-function acs4 protein as described herein. In heterozygous form, the other allele may thus be a reduced function acs4 allele.

In still another aspect, the invention relates to a an endogenous acs4 allele or to a loss-of-function acs4 protein or a reduced-function acs4 protein encoded by it having substantial sequence identity to SEQ. ID NO: 2 or to SEQ. ID NO: 3, or to SEQ. ID NO: 4, or to SEQ. ID NO: 5 or to SEQ. ID NO: 6, or to SEQ. ID NO: 7 as found in (and as derivable from) seed deposited under accession number NCIMB 42034, NCIMB 42037, NCIMB 42038, NCIMB 42039, or NCIMB 42041.

In yet another aspect, the invention relates to a tomato plant of the invention comprising an endogenous acs4 allele encoding a loss-of-function acs4 protein or reduced-function acs4 protein having 100% sequence identity to SEQ. ID NO: 2, or to SEQ. ID NO: 3, or to SEQ. ID NO: 4, or to SEQ. ID NO: 5, or to SEQ. ID NO: 6, or to SEQ. ID NO: 7.

In yet a further aspect, the invention relates to a plant of the invention comprising an endogenous acs4 allele encoding a loss-of-function acs4 protein or reduced-function acs4 protein having at least one amino acid deletion, insertion or replacement in the "large-domain". Preferably the acs4 protein comprises functional small domains, such as the small domains of SEQ ID NO: 1 (acid residues 33 to 62 and/or 339 to 438) or the small domains of a (functional) variant of SEQ ID NO: 1. In one embodiment it also comprises the C-terminal of SEQ ID NO: 1 (amino acids 444 to 476) or the C-terminal of a (functional) variant of SEQ ID NO: 1.

In one aspect, the acs4 protein is not longer than 203 amino acids preferably the first 203 amino acids. Thus, in one embodiment the tomato plant encodes a truncated acs4 protein, comprising amino acids 1-450, 1-400, 1-350, 1-300, 1-250, or 1-203 of SEQ ID NO: 1 or a variant thereof.

The invention further relates to tomato seeds, plants and plant parts comprising an endogenous acs4 gene encoding a cDNA (mRNA) having substantial sequence identity to SEQ. ID NO: 8 and having at least one non-transgenic mutation within said endogenous acs4 gene, wherein said at least one non-transgenic mutation results in the production of a mutant acs4 protein having loss-of-function acs4 protein or reduced activity compared to wild type Acs4 protein. Preferably, said mutation results in reduced ethylene production and/or slower fruit ripening and/or a longer shelf life compared to *Solanum lycopersicum* being homozygous for the functional wild type Acs4 allele, encoding the protein of SEQ ID NO: 1 or a functional variant thereof. The mutation described anywhere herein may be human-induced or it may be a natural mutation. The plant is preferably a cultivated tomato plant. In one embodiment the mutation results in either a stop-codon or in an amino acid substitution. In one embodiment the amino acid selected from the group consisting of Ala248, Val250, Ser279, Thr316 and Leu321 of the wild type Acs4 protein is substituted for a different amino acid, e.g. Ala248Val, Val250Glu, Ser279Asn, Thr316Ile and Leu321Phe. In another embodiment, said mutation is selected from the group consisting of G836A, C743T, A610T, G963T, T749A, and C947T of SEQ ID NO: 8.

In another aspect the invention relates to tomato seeds, plants and plant parts comprising an endogenous mutant acs4 gene wherein said non-transgenic mutation creates an amino acid change in the acs4 protein encoded by and produced by transcription and translation of the acs4 gene, wherein said amino acid change is selected from the group consisting of S279N, A248V, L321F, V250E, T316I, and the complete deletion of amino acids 204 to 476 of SEQ ID NO: 1.

In yet another aspect the invention relates to acs4 protein having substantial sequence identity to SEQ ID NO: 2. In still another aspect the invention relates to acs4 protein having substantial sequence identity to SEQ ID NO: 3. In a further aspect the invention relates to acs4 protein having substantial sequence identity to SEQ ID NO: 4. In yet another aspect the invention relates to acs4 protein having substantial sequence identity to SEQ ID NO: 5. In still another aspect the invention relates to acs4 protein having substantial sequence identity to SEQ ID NO: 6. In a further aspect the invention relates to acs4 protein having substantial sequence identity to SEQ ID NO: 7. The invention also relates to tomato seeds, plants and plant parts comprising a nucleotide sequence encoding these proteins.

In still another aspect, the invention relates to tomato fruit, seeds, pollen, plant parts, and/or progeny of a plant of the invention. Preferably, the invention relates to fruit or seeds of the plant of the invention. More preferably, the invention relates to tomato fruit having delayed ripening and/or an increased post-harvest shelf life caused by a non-transgenic mutation in at least one acs4 allele, as described elsewhere herein.

In one aspect the tomato plants according to the invention have a delay of breaker stage, meaning that the mutants according to the invention require significantly more clays e.g. 1, 2, 3, 4, 5, 6, 7, 8, 9, or 10 or more days than wild type Acs4/Acs4 controls for the first fruits and/or for all fruits to have entered breaker stage.

In another aspect fruits of the tomato plants of the invention require more days to go from breaker stage to red stage, e.g. fruits of the plants of the invention require 1, 2, 3, 4, 5, 6, 7, 8, 9, 10, 11, 12, 13 or 14 or more days than wild type Acs4/Acs4 controls to go from breaker stage to red stage.

In another aspect the invention relates to a fruit of a plant of the invention having a the shelf life that is at least 2 days longer than the shelf life of a tomato fruit being homozygous for the wild type Acs4 allele. In still another aspect the invention relates to a fruit according to a plant of the invention having a reduced ethylene production that is at least 15% reduced, or at least 20% reduced compared to *Solanum lycopersicum* being homozygous for the wild type Acs4 allele.

In a particular aspect the tomato plants according to the invention have a shelf life that is significantly longer than the shelf life of wild type plants, for example the number of days from the first fruit being in breaker stage (or turning stage, pink stage, red stage or from harvest) up to the first fruit starting to become 'bad' and unsuitable for sale or consumption is significantly longer, e.g. at least 1, 2, 3, 4, 5, 6, 7, 8, 9, 10, or more, days longer than fruits of control plants (such as wild type Acs4/Acs4 plants), when plants are grown under the same conditions and fruits are treated the same way and kept under the same conditions.

Figure 2:
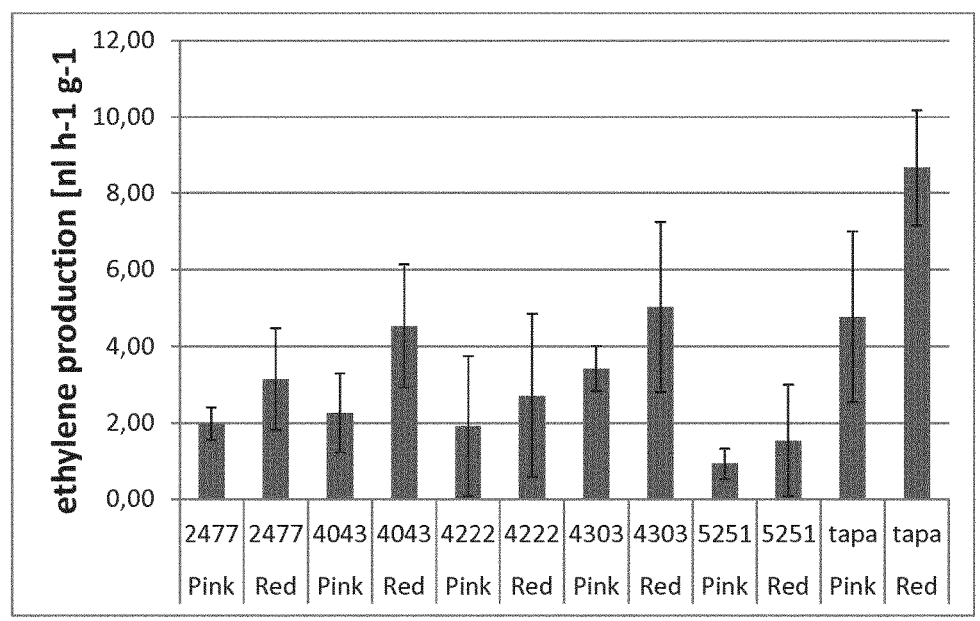
FIG. 2: Ethylene-release measured in nl/(h·g), also written as nl·h$^{-1}$·g$^{-1}$, from tomato fruits at Pink stage and Red stage. Tapa is a commercial wild type cultivar (Acs4/Acs4).

A delayed ripening and/or extended shelf-life can have the advantage that more time is available for transport of picked fruits e.g. to retailers and supermarkets and/or that the consumer can keep the fruits longer. Tomatoes can be harvested at mature green stage or at breaker stage, or thereafter. When harvested before breaker stage, ethylene exposure is needed, while harvest around breaker stage or thereafter does not require ethylene exposure, as the fruits produce ethylene themselves. As seen in FIG. 2, delayed-ripening mutants according to the invention produce less ethylene at pink stage and red stage than wild type fruits, but sufficient ethylene to ripen to the red stage. In one aspect of the invention tomato plants are provided comprising a mutant acs4 allele encoding a loss-of-function acs4 protein or reduced function acs4 protein, wherein the fruits of said plants produce significantly less ethylene than wild type (Acs4/Acs4) plants. "Significantly less ethylene" refers to the fruit producing equal to or less than 75%, equal to or less than 70%, equal to or less than 65%, equal to or less than 60%, equal to or less than 55%, equal to or less than 50%, equal to or less than 45%, equal to or less than 40%, equal to or less than 35%, equal to or less than 30%, equal to or less than 25% equal to or less than 20%, or equal to or less than 15% of the ethylene produced by homozygous Acs4/Acs4 fruits at the pink or red stage. Thus, the ethylene produced at the pink stage is in one aspect below about 3.5 nl/(h·g), such as equal to or below about 3 nl/(h·g) or equal to or below about 2.5 nl/(h·g) or equal to or below about 2.0 nl/(h·g) or equal to or below about 1.5 nl/(h·g) or equal to or below about 1.0 nl/(h·g) or equal to or below about 0.5 nl/(h·g). The ethylene produced at the red stage is in one aspect below about 6 nl/(h·g), such as equal to or below about 5.5 nl/(h·g) or equal to or below about 5.0 nl/(h·g), or equal to or below 4.5 nl/(h·g), or equal to or below about 3.5 nl/(h·g), or equal to or below about 3 nl/(h·g) or equal to or below about 2.5 nl/(h·g) or equal to or below about 2.0 nl/(h·g) or equal to or below about 1.5 nl/(h·g) or equal to or below about 1.0 nl/(h·g) or equal to or below about 0.5 nl/(h·g).

In another aspect, the invention relates to tomato fruit of a plant of the invention having a longer ripening period and/or an increased post-harvest shelf life caused by a non-transgenic mutation in at least one acs4 allele wherein the longer ripening period and/or the longer post-harvest shelf life is at least 110% of the ripening period and/or of the post-harvest shelf life of a tomato fruit being homozygous for the wild type Acs4 allele. Preferably, the ripening period and/or post-harvest shelf life is at least 115%, more preferably at least 120%, even more preferably at least 125% of the ripening period and/or post-harvest shelf life of a tomato fruit being homozygous for the wild type Acs4 allele. In another aspect, the ripening period and/or post-harvest shelf life is at least 135%, more preferably at least 150%, even more preferably at least 165% of the ripening period and/or post-harvest shelf life of a tomato fruit being homozygous for the wild type Acs4 allele. In yet another aspect, the ripening period and/or post-harvest shelf life is at least 180%, more preferably at least 200% even more preferably at least 250% of the ripening period and/or post-harvest shelf life of a tomato fruit being homozygous for the wild type Acs4 allele.

In still another aspect of the invention tomato plants are provided that have the same or similar delayed ripening and/or increased shelf life as tomato plants of the invention, of which representative seeds were deposited by Nunhems B. V. and accepted for deposit on 21 Aug. 2012 at the NCIMB Ltd. (Ferguson Building, Craibstone Estate, Bucksburn Aberdeen, Scotland AB21 9YA, UK) according to the Budapest Treaty, under the Expert Solution (EPC 2000, Rule 32(1)). Seeds were given the following deposit numbers: NCIMB 42034 (mutant 2477), NCIMB 42037 (mutant 4043), NCIMB 42038 (mutant 4222), NCIMB 42039 (mutant 4691), NCIMB 42041 (mutant 5251).

According to a further aspect the invention provides a cell culture or tissue culture of the tomato plant of the invention. The cell culture or tissue culture comprises regenerable cells. Such cells can be derived from leaves, pollen, embryos, cotyledon, hypocotyls, meristematic cells, roots, root tips, anthers, flowers, seeds and stems.

Seeds from which plants according to the invention can be grown are also provided, as well as packages containing such seeds. Also a vegetative propagation of plants according to the invention are an aspect encompassed herein. Likewise harvested fruits and fruit parts, either for fresh consumption or for processing or in processed form are encompassed. Fruits may be graded, sized and/or packaged. Fruits may be sliced or diced or further processed.

In another aspect the invention relates to one or more cells of a plant of the invention.

The invention also relates to food and/or food products incorporating the fruit or part of a fruit of a tomato plant of the invention. As used herein, food refers to nutrients consumed by human or animal species. Examples are sandwiches, salads, sauces, ketchup and the like.

In another aspect the invention relates to a method of producing a tomato plant of the invention comprising the steps of:
a. obtaining plant material from a tomato plant;
b. treating said plant material with a mutagen to create mutagenized plant material;
c. analyzing said mutagenized plant material to identify a plant having at least one mutation in at least one acs4 allele having substantial sequence identity to SEQ ID NO: 1 or variants thereof.

The method may further comprise analyzing the ripening period and/or shelf life of tomato fruits of the selected plant or progeny of the plant and selecting a plant of which the fruit have delayed ripening and/or extended shelf-life.

In one aspect the mutation may be selected from a mutation in the large domain of the acs4 protein and/or in the second small domain of the acs4 protein (amino acids 339-438). In one aspect the mutation is selected from a mutation resulting in an amino acid substitution selected from the group consisting of S279N, A248V, L321F, V250E, T316I, or from a stop-codon mutation causing the deletion of amino acids 204 to 476 of SEQ ID NO: 1 or of a part thereof. In a further aspect, the mutation is selected from a mutation causing a change in the cDNA selected from the group G836A, C743T, A610T, G963T, T749A, and C947T of SEQ ID NO: 8. In this method, the plant material of step a) is preferably selected from the group consisting of seeds, pollen, plant cells, or plant tissue of a tomato plant line or cultivar. Plant seeds being more preferred. In another aspect, the mutagen used in this method is ethyl methanesulfonate. In step b) and step c) the mutagenized plant material is preferably a mutant population, such as a tomato TILLING population.

Thus, in one aspect a method for producing a tomato plant comprising delayed fruit ripening and/or longer fruit shelf-life is provided comprising the steps of:
a) providing a tomato TILLING population,
b) screening said TILLING population for mutants in the acs4 gene, especially in the large-domain encoding nucleotide sequence, and
c) selecting from the mutant plants of b) those plants (or progeny of those plants) of which the fruits have a reduced ethylene production and/or a delayed ripening and/or longer shelf life than wild type (Acs4/Acs4) fruits.

Mutant plants (M1) are preferably selfed one or more times to generate for example M2 populations or preferably M3 or M4 populations for phenotyping. In M2 populations the mutant allele is present in a ratio of 1 (homozygous for mutant allele):2 (heterozygous for mutant allele):1 (homozygous for wild type allele).

In yet a further aspect the invention relates to a method for producing a hybrid *Solanum lycopersicum* plant, said method comprising:
(a) obtaining a first *Solanum lycopersicum* plant of the current invention and
(b) crossing said first *Solanum lycopersicum* plant with a second *Solanum lycopersicum* plant;
wherein said hybrid *Solanum lycopersicum* plant comprises an acs4 allele having one or more mutations wherein said mutations result in production of a mutant acs4 protein having loss-of-function acs4 protein or reduced activity compared to wild type Acs4 protein.

Plants and plant parts (e.g. fruits, cells, etc.) of the invention can homozygous or heterozygous for the mutant acs4 allele.

Preferably the plants according to the invention, which comprise one or more mutant acs4 alleles (or variants), and which produce a mutant acs4 protein having loss-of-function acs4 protein or reduced activity compared to wild type Acs4 protein, do not produce fewer fruits than the wild type plants. Thus, fruit number per plant is preferably not reduced.

Other putative ACS4 genes/proteins can be identified in silico, e.g. by identifying nucleic acid or protein sequences in existing nucleic acid or protein database (e.g. GENBANK, SWISSPROT, TrEMBL) and using standard sequence analysis software, such as sequence similarity search tools (BLASTN, BLASTP, BLASTX, TBLAST, FASTA, etc.).

In one embodiment loss-of-function acs4 protein or reduced-function mutant acs4 proteins (including variants or orthologs, such as acs4 proteins of wild tomato relatives) are provided and plants and plant parts comprising one or more acs4 alleles in their genome, which encode loss-of-function acs4 protein or reduced-function mutants, whereby the reduced-function confers reduced ethylene production and/or slower fruit ripening and/or a longer shelf life compared to *Solanum lycopersicum* being homozygous for the wild type Acs4 allele.

Any type of mutation may lead to a reduction in function of the encoded Acs4 protein, e.g. insertion, deletion and/or replacement of one or more nucleotides in the genomic DNA which comprises the cDNA (SEQ ID NO: 8, or variants thereof). In a preferred embodiment is provided an acs4 nucleic acid sequence capable of reduced ethylene production and/or conferring slower fruit ripening and/or a longer shelf life compared to *Solanum lycopersicum* being homozygous for the wild type Acs4 allele, whereby the nucleic acid sequence encodes a loss-of-function acs4 protein or reduced-function Acs4 protein due to one or more mutations in the large domain.

The in vivo loss-of-function acs4 protein or reduced-function of such proteins can be tested as described herein, by determining the effect this mutant allele has on ethylene production and/or ripening period and/or shelf life period. Plants comprising a nucleic acid sequence encoding such mutant loss-of-function acs4 protein or reduced-function proteins and having a reduced ethylene production and/or slower fruit ripening and/or a longer shelf life compared to *Solanum lycopersicum* being homozygous for the wild type Acs4 allele can for example be generated using e.g. mutagenesis and identified by TILLING or identified using EcoTILLING, as known in the art. Also transgenic methods can be used to test in vivo functionality of a mutant acs4 allele encoding a mutant acs4 protein. A mutant allele can be operably linked to a plant promoter and the chimeric gene can be introduced into a tomato plant by transformation. Regenerated plants (or progeny, e.g. obtained by selfing), can be tested for ethylene production and/or fruit ripening period and/or shelf life. For example a tomato plant comprising a non-functional acs4 allele can be transformed to test the functionality of the transgenic acs4 allele.

TILLING (Targeting Induced Local Lesions IN Genomes) is a general reverse genetic technique that uses traditional chemical mutagenesis methods to create libraries of mutagenized individuals that are later subjected to high throughput screens for the discovery of mutations. TILLING combines chemical mutagenesis with mutation screens of pooled PCR products, resulting in the isolation of missense and non-sense mutant alleles of the targeted genes. Thus, TILLING uses traditional chemical mutagenesis (e.g. EMS or MNU mutagenesis) or other mutagenesis methods (e.g. radiation such as UV) followed by high-throughput screening for mutations in specific target genes, such as Acs4 according to the invention. S1 nucleases, such as CEL1 or ENDO1, are used to cleave heteroduplexes of mutant and wildtype target DNA and detection of cleavage products using e.g. electrophoresis such as a LI-COR gel analyzer system, see e.g. Henikoff et al. Plant Physiology 2004, 135: 630-636. TILLING has been applied in many plant species, such as tomato. (see http://tilling.ucdavis.edu/index.php/Tomato_Tilling), rice (Till et al. 2007, BMC Plant Biol 7: 19), *Arabidopsis* (Till et al. 2006, Methods Mol Biol 323: 127-35), *Brassica*, maize (Till et al. 2004, BMC Plant Biol 4: 12), etc. Also EcoTILLING, whereby mutants in natural populations are detected, has been widely used, see Till et al. 2006 (Nat Protoc 1: 2465-77) and Comai et al. 2004 (Plant J 37: 778-86).

In one embodiment of the invention (cDNA or genomic) nucleic acid sequences encoding such mutant acs4 proteins comprise one or more non-sense and/or missense mutations, e.g. transitions (replacement of purine with another purine (A↔G) or pyrimidine with another pyrimidine (C↔T)) or transversions (replacement of purine with pyrimidine, or vice versa (C/T↔A/G). In one embodiment the non-sense and/or missense mutation(s) is/are in the nucleotide sequence encoding any of the Acs4 exons, more preferably in the ACS4 large domain or an essentially similar domain of a variant Acs4 protein, i.e. in a domain comprising at least 80%, 90%, 95%, 98%, 99% amino acid identity to amino acids 65-327 of SEQ ID NO: 1 or variants thereof.

In one embodiment an acs4 nucleotide sequence comprising one or more non-sense and/or missense mutations in one of the exon-encoding sequence are provided, as well as a plant comprising such a mutant allele resulting in reduced ethylene production and/or delayed fruit ripening and/or a longer shelf life compared to *Solanum lycopersicum* being homozygous for the wild type Acs4 allele.

In a specific embodiment of the invention tomato plants and plant parts (fruits, seeds, etc.) comprising a mutant loss-of-function or reduced-function acs4 allele are provided.

In one embodiment, the loss-of-function acs4 protein or reduced-function acs4 protein is a truncated protein, i.e. a protein fragment of any one of the Acs4 proteins defined further above (including variants thereof). In general EMS (Ethyl methanesulfonate) induces substitutions of guanine/cytosine to adenin/thymine. In case of a glutamine (Gln or Q, encoded by the nucleotides CAA or CAG) or arginine (Arg or R, encoded by the nucleotides CGA) codon, a substitution of the cytosine for thymine can lead to the introduction of a stop codon in the reading frame (for example CAA/CAG/CGA to TAA/TAG/TGA) resulting in a truncated protein.

Also provided are nucleic acid sequences (genomic DNA, cDNA, RNA) encoding loss-of-function acs4 protein or reduced-function acs4 proteins, such as for example acs4 depicted in SEQ ID NO: 2, 3, 4, 5, 6, or 7; or variants thereof as defined above (including any chimeric or hybrid proteins or mutated proteins or truncated proteins). Due to the degeneracy of the genetic code various nucleic acid sequences may encode the same amino acid sequence. The nucleic acid sequences provided include naturally occurring, artificial or synthetic nucleic acid sequences. A nucleic acid sequence encoding Acs4 is provided for in SEQ ID NO: 8 (wild type cDNA), Genbank Accession Number M63490.1.

It is understood that when sequences are depicted as DNA sequences while RNA is referred to, the actual base sequence of the RNA molecule is identical with the difference that thymine (T) is replace by uracil (U). When referring herein to nucleotide sequences (e.g DNA or RNA) italics are used, e.g. acs4 allele, while when referring to proteins, no italics are used, e.g. acs4 protein. Mutants are in small letters (e.g acs4 allele or acs4 protein), while wild type/functional forms start with a capital letter (Acs4 allele or Acs4 protein).

Also provided are nucleic acid sequences (genomic DNA, cDNA, RNA) encoding mutant acs4 proteins, i.e. loss-of-function acs4 protein or reduced function acs4 proteins, as described above, and plants and plant parts comprising such mutant sequences. For example, acs4 nucleic acid sequences comprising one or more non-sense and/or missense mutations in the wild type Acs4 coding sequence, rendering the encoded protein having a loss-of-function or reduced function in vivo. Also sequences with other mutations are provided, such as splice-site mutants, i.e. mutations in the genomic acs4 sequence leading to aberrant splicing of the pre-mRNA, and/or frame-shift mutations, and/or insertions (e.g. transposon insertions) and/or deletions of one or more nucleic acids.

It is clear that many methods can be used to identify, synthesise or isolate variants or fragments of acs4 nucleic acid sequences, such as nucleic acid hybridization, PCR technology, in silico analysis and nucleic acid synthesis, and the like. Variants of SEQ ID NO: 8, may either encode wild type, functional Acs4 proteins, or they may encode loss-of-function acs4 protein or reduced-function mutant alleles of any of these, as for example generated e.g. by mutagenesis and/or identified by methods such as TILLING or EcoTILLING, or other methods.

A plant of the invention can be used in a conventional plant breeding scheme to produce more plants with the same characteristics or to introduce the mutated acs4 allele into other plant lines or varieties of the same or related plant species.

Also transgenic plants can be made using the mutant acs4 nucleotide sequences of the invention using known plant transformation and regeneration techniques in the art. An "elite event" can be selected, which is a transformation event having the chimeric gene (comprising a promoter operably linked to a nucleotide sequence encoding a loss-of-function acs4 protein or reduced-function acs4 protein) inserted in a particular location in the genome, which results in good expression of the desired phenotype.

The plants of the invention as described above are homozygous for the mutant acs4 allele, or heterozygous. To generate plants comprising the mutant allele in homozygous form, selfing can be used. The mutant acs4 alleles according to the invention can be transferred to any other tomato plant by traditional breeding techniques, such as crossing, selfing, backcrossing, etc. Thus any type of tomato having delayed ripening and/or longer shelf life due to the presence of at least one mutant acs4 allele according to the invention can be generated. Any *S. lycopersicum* may be generated and/or identified having at least one mutant acs4 allele in its genome and producing a acs4 protein having loss-of-function acs4 protein or reduced activity compared to wild type Acs4 protein. The tomato plant may, thus, be any cultivated tomato, any commercial variety, any breeding line or other, it may be determinate or indeterminate, open pollinated or hybrid, producing fruits of any colour, shape and size. The mutant allele generated and/or identified in a particular tomato plant, or in a sexually compatible relative of tomato, may be easily transferred into any other tomato plant by breeding (crossing with a plant comprising the mutant allele and then selecting progeny comprising the mutant allele).

The presence or absence of a mutant acs4 allele according to the invention in any tomato plant or plant part and/or the inheritance of the allele to progeny plants can be determined phenotypically and/or using molecular tools (e.g. detecting the presence or absence of the acs4 nucleotide or acs4 protein using direct or indirect methods).

The mutant allele is in one embodiment generated or identified in a cultivated plant, but may also be generated and/or identified in a wild plant or non-cultivated plant and then transferred into an cultivated plant using e.g. crossing and selection (optionally using interspecific crosses with e.g. embryo rescue to transfer the mutant allele). Thus, a mutant acs4 allele may be generated (human induced mutation using mutagenesis techniques to mutagenize the target acs4 gene or variant thereof) and/or identified (spontaneous or natural allelic variation) in *Solanum lycopersicum* or in other *Solanum* species include for example wild relatives of tomato, such as *S. cheesmanii, S. chilense, S. habrochaites* (*L. hirsutum*), *S. chmielewskii, S. lycopersicum×S. peruvianum, S. glandulosum, S. hirsutum, S. minutum, S. parviflorum, S. pennellii, S. peruvianum, S. peruvianum* var. *humifusum* and *S. pimpinellifolium*, and then transferred into a cultivated *Solanum* plant, e.g. *Solanum lycopersicum* by traditional breeding techniques. The term "traditional breeding techniques" encompasses herein crossing, selfing, selection, double haploid production, embryo rescue, protoplast fusion, transfer via bridge species, etc. as known to the breeder, i.e. methods other than genetic modification by which alleles can be transferred.

In another embodiment, the plant comprising the mutant acs4 allele (e.g. tomato) is crossed with another plant of the same species or of a closely related species, to generate a hybrid plant (hybrid seed) comprising the mutant acs4 allele. Such a hybrid plant is also an embodiment of the invention.

In one embodiment F1 hybrid tomato seeds (i.e. seeds from which F1 hybrid tomato plants can be grown) are provided, comprising at least one acs4 allele according to the invention. F1 hybrid seeds are seeds harvested from a cross between two inbred tomato parent plants. Such an F1 hybrid may comprise one or two mutant acs4 alleles according to the invention. Thus, in one embodiment a plant according to the invention is used as a parent plant to produce an F1 hybrid, the fruit of which have reduced ethylene production and/or delayed ripening and/or longer shelf-life than wild type Acs4/Acs4 plants.

Also a method for transferring a mutant acs4 allele to another plant is provided, comprising providing a plant comprising a mutant acs4 allele in its genome, whereby the mutant allele produce fruits that show reduced ethylene production and/or slower fruit ripening and/or a longer shelf life compared to *Solanum lycopersicum* being homozygous for the wild type Acs4 allele (as described above), crossing said plant with another plant and obtaining the seeds of said cross. Optionally plants obtained from these seeds may be further selfed and/or crossed and progeny selected comprising the mutant allele and producing fruits with delayed ripening and/or longer shelf-life and/or reduced ethylene production due to the presence of the mutant allele compared to plants comprising the wild type Acs4 allele.

As mentioned, it is understood that other mutagenesis and/or selection methods may equally be used to generate mutant plants according to the invention. Seeds may for example be radiated or chemically treated to generate mutant populations. Also direct gene sequencing of acs4 may be used to screen mutagenized plant populations for mutant alleles. For example KeyPoint screening is a sequence based method which can be used to identify plants comprising mutant acs4 alleles (Rigola et al. PloS One, March 2009, Vol 4(3):e4761).

Thus, non-transgenic mutant tomato plants which produce lower levels of wild type Acs4 protein in fruits are provided, or which completely lack wild type Acs4 protein in fruits, and which produce loss-of-function acs4 protein or reduced-function acs4 protein in fruits due to one or more mutations in one or more endogenous acs4 alleles, are provided. These mutants may be generated by mutagenesis methods, such as TILLING or variants thereof, or they may be identified by EcoTILLING or by any other method. Acs4 alleles encoding loss-of-function acs4 protein or reduced-functional acs4 protein may be isolated and sequenced or may be transferred to other plants by traditional breeding methods.

Any part of the plant, or of the progeny thereof, is provided, including harvested fruit, harvested tissues or organs, seeds, pollen, flowers, ovaries, etc. comprising a mutant acs4 allele according to the invention in the genome. Also plant cell cultures or plant tissue cultures comprising in their genome a mutant acs4 allele are provided. Preferably, the plant cell cultures or plant tissue cultures can be regenerated into whole plants comprising a mutant acs4 allele in its genome. Also double haploid plants (and seeds from which double haploid plants can be grown), generated by chromosome doubling of haploid cells comprising an acs4 mutant allele, and hybrid plants (and seeds from which hybrid plants can be grown) comprising a mutant acs4 allele in their genome are encompassed herein, whereby the double haploid plants and hybrid plants produce delayed ripening and/or longer shelf life fruits according to the invention.

Preferably, the mutant plants also have good other agronomic characteristics, i.e. they do not have reduced fruit numbers and/or reduced fruit quality compared to wild type plants. In a preferred embodiment the plant is a tomato plant and the fruit is a tomato fruit, such as a processing tomato, fresh market tomato of any shape or size or colour. Thus, also harvested products of plants or plant parts comprising one or two mutant acs4 alleles are provided. This includes downstream processed products, such as tomato paste, ketchup, tomato juice, cut tomato fruit, canned fruit, dried fruit, peeled fruit, etc. The products can be identified by comprising the mutant allele in their genomic DNA.

Seed Deposits

A representative sample of seeds of five tomato TILLING mutants according to Example 1, were deposited by Nunhems B. V. and accepted for deposit on 21 Aug. 2012 at the NCIMB Ltd. (Ferguson Building, Craibstone Estate, Bucksburn Aberdeen, Scotland AB21 9YA, UK) according to the Budapest Treaty, under the Expert Solution (EPC 2000, Rule 32(1)). Seeds were given the following deposit numbers: NCIMB 42034 (mutant 2477), NCIMB 42037 (mutant 4043), NCIMB 42038 (mutant 4222), NCIMB 42039 (mutant 4691), NCIMB 42041 (mutant 5251).

The Applicant requests that samples of the biological material and any material derived therefrom be only released to a designated Expert in accordance with Rule 32(1) EPC or related legislation of countries or treaties having similar rules and regulation, until the mention of the grant of the patent, or for 20 years from the date of filing if the application is refused, withdrawn or deemed to be withdrawn.

Access to the deposit will be available during the pendency of this application to persons determined by the Director of the U.S. Patent Office to be entitled thereto upon request. Subject to 37 C.F.R. §1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

EXAMPLES

General Methods

PCR amplification products were directly sequenced by a service company (BaseClear, The Netherlands, world wide web at baseclear.com/) using the same primers as were used for the amplification. The obtained sequences were aligned using a computer program (CLC Bio Main Work Bench, Denmark, world wide web at cicbio.com) to identify the nucleotide changes.

Materials

Water used for analyses and mutagenis is tap water filtered in an Milli-Q water Integral system, Milli-Q type Reference A+ supplied with a Q-gard T2 Cartridge and a Quantum TEX Cartridge. Water resistance is >=18 MOhm.

Ethyl Methanesulfonate (EMS) (pure) was obtained from Sigma, product number M0880.

Measurement of Tomato Ripening and/or Shelf-Life Time or Periods

Tomato ripening and/or shelf life time or periods can be measured by various methods known in the art like for example making periodically visual assessments of fruits and/or measurement of fruit firmness or softening, measurement of lycopene contents in the tomato fruits, ethylene production by the fruits, colour of the fruits or any alternative method or combination of methods. Fruit firmness can for example be measured by evaluating resistance to deformation in units of for example 0.1 mm as measured with a penetrometer fitted with a suitable probe (e.g. a probe of 3 mm) (Mutschler et al, 1992, Horscience 27 pp 352-355) (Marinez et al 1995 Acta Horticulturae 412 pp 463-469). Alternative methods exist in the art, such as use of a texturometer (Bui et al. 2010; International Journal of Food Properties, Volume 13, Issue 4).

Fruit colour can be classified by the U.S. standards for grades of fresh tomato (U.S. Dept of Agriculture, 1973, US standards for grades of fresh tomatoes, U.S. Dept Agr. Agr. Mktg. Serv., Washington D.C.), measuring the colour with a chromometer (Mutschler et al, 1992, Horscience 27 pp 352-355) or by comparing the colour to a colour chart like the Royal Horticultural Society (RHS) Color Chart (world wide web at rhs.org.uk).

Lycopene content can be determined according to the reduced volumes of organic solvents method of Fish et al. A quantitative assay for lycopene that utilizes reduced volumes of organic solvents. *J. Food Compos. Anal.* 2002, 15, 309-317. This method can be used to determine lycopene content measured directly on intact tomato fruit while simultaneously estimating the basic physicochemical characteristics: color, firmness, soluble solids, acidity, and pH (Clement et al, *J. Agric. Food Chem.* 2008, 56, 9813-9818).

Ethylene release can be measured by placing the fruit in a closed space, e.g. in a 0.5 l glass holder. One ml of holder atmosphere can be extracted after one hour and amount of ethylene gas produced can be quantified using a gas chromatograph (e.g. a Hewlett-Packard 5890) equipped with a suitable detection unit, e.g. a flame ionisation detector, and a suitable column (e.g. a 3 m stainless steel column with an inner diameter of 3.5 mm containing activated alumina of 80/100 mesh). Ethylene production can be expressed as the amount in nl of ethylene given off per gram of fruit per hour (nl g-1 h-1) (Marinez et al 1995 Acta Horticulturae 412 pp 463-469).

Alternatively, ethylene production can be measured as described further below, using real-time measurements with a laser-based ethylene detector (ETD-300, Sensor Sense B.V., Nijmegen, the Netherlands) in combination with a gas handling system (Cristecu et al., 2008).

Example 1

Mutagenesis

A highly homozygous inbred line used in commercial processing tomato breeding was used for mutagenesis treatment with the following protocol. After seed germination on damp Whatman® paper for 24 h, -20,000 seeds, divided in 8 batches of 2500 respectively, were soaked in 100 ml of ultrapure water and ethyl methanesulfonate (EMS) at a concentration of 1% in conical flasks. The flasks were gently shaken for 16 h at room temperature. Finally, EMS was rinsed out under flowing water. Following EMS treatment, seeds were directly sown in the greenhouse. Out of the 60% of the seeds that germinated, 10600 plantlets were transplanted in the field. From these 10600 plantlets, 1790 were either sterile or died before producing fruit. For each remaining M1 mutant plant one fruits was harvested and its seeds isolated. The obtained population, named M2 population, is composed of 8810 seeds lots each representing one M2 family. Of these, 585 families were excluded from the population due to low seed set.

DNA was extracted from a pool of 10 seeds originating from each M2 seed lot. Per mutant line, 10 seeds were pooled in a Micronic® deepwell tube; world wide web at micronic.com from a 96 deep-well plate, 2 stainless balls were added to each tube. The tubes and seeds were frozen in liquid nitrogen for 1 minute and seeds were immediately ground to a fine powder in a Deepwell shaker (Vaskon 96 grinder, Belgium; world wide web at vaskon.com) for 2 minutes at 16.8 Hz (80% of the maximum speed). 300 µl Agowa® Lysis buffer P from the AGOWA0 Plant DNA Isolation Kit world wide web at agowa.de was added to the sample plate and the powder was suspended in solution by shaking 1 minute at 16.8 Hz in the Deepwell shaker. Plates were centrifuged for 10 minutes at 4000 rpm. 75 µl of the supernatant was pipetted out to a 96 Kingfisher plate using a Janus MDT® (Perkin Elmer, USA; world wide web at perkinelmer.com) platform (96 head). The following steps were performed using a Perkin Elmer Janus® liquid handler robot and a 96 Kingfisher® (Thermo labsystems, Finland; world wide web at thermo.com). The supernatant containing the DNA was diluted with binding buffer (150 µl) and magnetic beads (20 pl). Once DNA was bound to the beads, two successive washing steps were carried out (Wash buffer 1: Agowa wash buffer 1⅓, ethanol ⅓, isopropanol ⅓; Wash buffer 2: 70% ethanol, 30% Agowa wash buffer 2) and finally eluted in elution buffer (100 pl MQ, 0.025 µl Tween).

Grinding ten *S. lycopersicum* seeds produced enough DNA to saturate the magnetic beads, thus highly homogenous and comparable DNA concentrations of all samples were obtained. Comparing with lambda DNA references, a concentration of 30 ng/µl for each sample was estimated. Two times diluted DNA was 4 fold flat pooled. 2 µl pooled DNA was used in multiplex PCRs for mutation detection analysis.

Primers used to amplify gene fragments for HRM were designed using a computer program (Primer3, world wide web at primer3.sourceforge.net/). The length of the amplification product was limited between 200 and 400 base pairs. Quality of the primers was determined by a test PCR reaction that should yield a single product.

Polymerase Chain Reaction (PCR) to amplify gene fragments. 10 ng of genomic DNA was mixed with 4 µl reaction buffer (5× Reaction Buffer), 2 µl 10×LC dye ((LCGreen+ dye, Idaho Technology Inc., UT, USA), 5 pmole of forward and reverse primers each, 4 nmole dNTPs (Life Technologies, NY, USA) and 1 unit DNA polymerase (Hot Start II DNA Polymerase) in a total volume of 100. Reaction conditions were: 30 s 98° C., then 40 cycles of 10 s. 98° C., 15 s 60° C., 25 s of 72° C. and finally 60 s at 72° C.

High Resolution Melt curve analysis (HRM) has been proven to be sensitive and high-throughput methods in human and plant genetics. HRM is a non-enzymatic screening technique. During the PCR amplification dye (LCGreen+dye, Idaho Technology Inc., UT, USA) molecules intercalate between each annealed base pair of the double stranded DNA molecule. When captured in the molecule, the dye emits fluorescence at 510 nm after excitation at 470 nm. A camera in a fluorescence detector (LightScanner, Idaho Technology Inc., UT, USA) records the fluorescence intensity while the DNA sample is progressively heated. At a temperature dependent on the sequence specific stability of the DNA helices, the double stranded PCR product starts to melt, releasing the dye. The release of dye results in decreased fluorescence that is recorded as a melting curve by the fluorescence detector. Pools containing a mutation form hetero duplexes in the post-PCR fragment mix. These are identified as differential melting temperature curves in comparison to homo duplexes.

Mutants showing a delayed ripening were selected and the type of mutation in the acs4 gene was determined.

The presence of the particular mutation in individual plants was confirmed repeating the HRM analysis on DNA from the individual M2 seed lots of the identified corresponding DNA pool. When the presence of the mutation, based on the HRM profile, was confirmed in one of the four individual M2 family DNA samples, the PCR fragments were sequenced to identify the mutation in the gene.

Once the mutation was known the effect of such an mutation was predicted using a computer program CODDLe (for Choosing codons to Optimize Discovery of Deleterious Lesions, world wide web at proweb.org/coddle/) that identifies the region(s) of a user-selected gene and of its coding sequence where the anticipated point mutations are most likely to result in deleterious effects on the gene's function.

Seeds from M2 families that contain mutations with predicted effect on protein activity were sown for phenotypic analysis of the plants.

Homozygous mutants were selected or obtained after setting and subsequent selection. The effect of the mutation on the corresponding protein and phenotype of the plant was determined.

Seeds containing the different identified mutations were germinated and plants were grown in pots with soil the greenhouse with 16/8 light dark regime and 18° C. night and 22-25° C. day temperature. For each genotype 5 plants were raised. The second, third and fourth inflorescence were used for the analysis. The inflorescences were pruned leaving six flowers per inflorescence that were allowed to set fruit by self-pollination. The dates of fruit set of the first and sixth flower was recorded as was the date of breaker and red stage of the first and sixth fruit. At breaker of the sixth fruit the truss was harvested and stored in an open box in the greenhouse. Fruit condition of the fruits was recorded during the whole ripening period.

At later stages fruit condition was determined based on visual assessment of the fruits and the date when the oldest fruit became 'bad' was recorded and further fruit deterioration was recorded (indicated by further fruit softness assessed by pinching the fruits, and visual assessment of dehydration/water loss, breaking of the skin and fungal growth).

The following mutants were identified: mutant 2477, mutant 4043, mutant 4222, mutant 4691, and mutant 5251, and seeds were deposited at the NCIMB under the Accession numbers given above.

In SEQ ID NO 8 the cDNA of wild type Acs4 is shown, which corresponds to the protein sequence depicted in SEQ ID NO 1.

Mutant 2477 (NCIMB 42034)

In mutant 2477 nucleotide 836 is changed from a G to A as shown in SEQ ID NO: 9, counting A in the ATG of the START CODON as nucleotide position 1. This mutation results in a change from serine to asparagine at amino acid 279 in the expressed protein. The S279N mutation is within the large-domain of the ACS4 protein. The protein sequence of mutant 2477 is depicted in SEQ ID NO: 2.

Mutant 4043 (NCIMB 42037)

In mutant 4043 nucleotide 743 is changed from C to T as shown in SEQ ID NO: 10 counting A in the ATG of the START CODON as nucleotide position 1. This mutation results in a change from alanine to valine at amino acid 248 in the expressed protein. The A248V mutation is within the large-domain of the ACS4 protein. The protein sequence of mutant 4043 is depicted in SEQ ID NO: 3.

Mutant 4222 (NCIMB 42038)

In mutant 4222 nucleotide 610 is changed from A to T as shown in SEQ ID NO: 11 counting A in the ATG of the START CODON as nucleotide position 1. The A610T mutation results in a change from a codon for lysine (AAA) to a STOP-codon (TAA) which results in a truncated protein of 203 amino acid residues during translation, whereas the native protein has 476 amino acid residues. The truncated protein sequence of mutant 4222 is depicted in SEQ ID NO: 4.

Mutant 4303

In mutant 4303 nucleotide 963 is changed from G to T as shown in SEQ ID NO: 12 counting A in the ATG of the START CODON as nucleotide position 1. This mutation results in a change from leucine to phenylalanine at amino acid 321 in the expressed protein. The L321F mutation is within the second small-domain of the ACS4 protein. The protein sequence of mutant 4303 is depicted in SEQ ID NO: 5.

Mutant 4691 (NCIMB 42039)

In mutant 4691 nucleotide 749 is changed from T to A as shown in SEQ ID NO: 13 counting A in the ATG of the START CODON as nucleotide position 1. This mutation results in a change from valine to glutamic acid at amino acid 250 in the expressed protein. The V250E mutation is within the large-domain of the ACS4 protein. The protein sequence of mutant 4691 is depicted in SEQ ID NO: 6.

Mutant 5251 (NCIMB 42041)

In mutant 5251 nucleotide 947 is changed from C to T as shown in SEQ ID NO: 14 counting A in the ATG of the START CODON as nucleotide position 1. This mutation results in a change from threonine to isoleucine at amino acid 316 in the expressed protein. The T316I mutation is within the second small-domain of the ACS4 protein. The protein sequence of mutant 5251 is depicted in SEQ ID NO: 7.

Plants comprising mutations in the target sequence, such as the above mutant plants or plants derived therefrom (e.g. by selfing or crossing) and comprising the mutant acs4 allele, show a normal vegetative growth of all plant parts when compared to wild-type plants except for the ripening of the tomato fruits. The plants comprising mutations in the target sequence were screened phenotypically for their fruit ripening, ethylene production and shelf live.

Example 2

Ripening Behaviour of the Acs4 Mutants

Seeds containing the different mutations were germinated and plants were grown in pots with soil the greenhouse with 16/8 light dark regime and 18° C. night and 22-25° C. day temperature. For each genotype 5 plants were raised. The second, third and fourth inflorescence were used for the analysis. The inflorescences were pruned, leaving six flowers per inflorescence that were allowed to set fruit by self-pollination. The dates of fruit set of the first and sixth flower was recorded as was the date of breaker and red stage of the first and sixth fruit. At red stage of the 4$^{th}$ fruit the truss was harvested and stored in an open box in the greenhouse. Fruit condition of the fruits was recorded during the whole ripening period by making pictures from each truss. After harvest pictures were made per box containing all trusses from one genotype.

At later stages fruit condition was determined based on visual assessment of the fruits and the date when the oldest fruit became 'bad' was recorded and further fruit deterioration was recorded (indicated by further fruit softness assessed by pinching the fruits, and visual assessment of dehydration/water loss, breaking of the skin and fungal growth).

Figure 3:
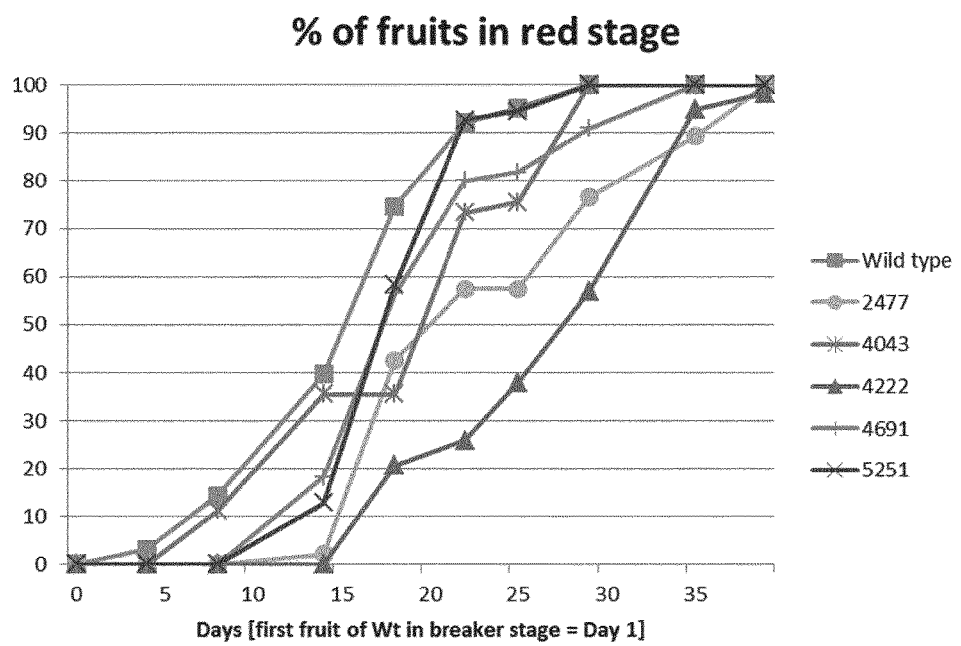
FIG. 3: In this graph the percentage of fruits in red stage is shown, determined at various days after the wild type control fruits started entering breaker stage [at day 1, the first fruit of Wild type was in breaker stage]. All fruits of mutant plants of the invention require more days to ripen compared to wild type (wt), 'Ho' means fruits of a mutant plant (indicated by the preceding number) being homozygous for a specific acs4 mutation (acs4/acs4); He means fruits of a mutant (indicated by the preceding number) being heterozygous for a specific acs4 mutation (Acs4/acs4).

The ripening behaviour of the fruits is shown in FIG. 3. The day on which the first fruit of the wild type plant came into breaker stage was taken as day 1. The days thereafter were numbered as consecutive days. Mutants show a delay in ripening, i.e. fruits of the mutants require more days to become red. Especially mutant 2477 and 4222 show a significant delay of several days. Mutant 4222 shows that it takes more time to go from first fruit in breaker stage to 100% fruit in red stage.

A characteristic of fruits of the plants of the invention is that breaker stage starts later (e.g. mutant 2477, 4222, 4691, 5251). Post-harvest characteristics are shown below.

| | First fruit in Breaker on day no. | All fruits in breaker stage on day no. | First fruit in red stage on day no. | 100% fruit in red stage on day no. |
|---|---|---|---|---|
| Wt | 1 | 25 | 2 | 27 |
| 2477 Ho | 11 | 35 | 14 | 39 |
| 4043 Ho | 1 | 24 | 6 | 29 |
| 4222 Ho | 11 | 39 | 16 | 46 |
| 4691 Ho | 8 | 32 | 10 | 35 |
| 5251 Ho | 8 | 24 | 41 | 28 |

As can be seen, mutant fruits enter breaker stage later (except mutant 4043) and the date when all fruits are in breaker stage is also later (except mutant 4043). Equally, mutant fruits come into the red stage later and the date when all fruits of a mutant line are in red stage is also significantly later than for the wild type.

Example 3

Ethylene Release

Ethylene released by tomato fruits was measured in real-time with a laser-based ethylene detector (ETD-300, Sensor Sense B. V., Nijmegen, the Netherlands) in combination with a gas handling system (Cristecu et al., Laser-based systems for trace gas detection in life sciences. Appl Phys B 2008; 92 pp 343-9). Six glass cuvettes (100 mL volume) were used per experiment, one as a reference without plant material. Air was sampled from the lab and passed through a platinum based catalyzer (Sensor Sense B. V., Nijmegen, the Netherlands) to remove traces of ethylene or other hydrocarbons. Between the sample and the detector scrubbers with KOH and CaCl2 were placed to reduce the $CO_2$ concentration (to less than 1 ppm) and decrease the water content in the gas flow, respectively.

Comparison of the ethylene released from fruits of mutant 2477, 4043, 4222, and 5251 with wild type (commercial variety tapa) at Pink stage and red stage revealed that at both stages the ethylene production of all mutants had reduced compared to wild type (commercial variety tapa). Mutant 4303 produced at pink stage 28% less ethylene than wild type, mutants 2477, 4043, and 4222 produced between 50 and 60% less ethylene than wild type. Mutant 5251 produced more than 80% less ethylene at pink stage compared to wild-type: <1.0 nl/(h·g) versus 4.8 nl/(h·g) for the wild type. The difference at red stage is even more significant: Mutant 4303 produced at red stage 42% less ethylene than wild type, mutants 2477, 4043, and 4222 produced between 48 and 74% less ethylene than wild type. Mutant 5251 produced more than 82% less ethylene at red stage compared to wild type. Wherein nl/(h·g) means nano liter per hour per gram of fruit.

The invention claimed is:

1. A cultivated plant or seeds of the species *Solanum lycopersicum* comprising an acs4 allele having one or more mutations, said one or more mutations resulting in production of a mutant acs4 protein having loss-of-function or reduced function compared to wild type Acs4 protein; wherein said mutant acs4 protein comprises one or more amino acid changes at Ala248, Ser279, Leu321, Val250, or Thr316; or wherein said mutant acs4 protein has a deletion of amino acids 204 to 476 of SEQ ID NO: 1.

2. The cultivated plant or seeds according to claim 1, wherein said one or more mutations result in reduced ethylene production and/or delayed fruit ripening and/or a longer shelf life compared to *Solanum lycopersicum* being homozygous for the wild type Acs4 allele.

3. The cultivated plant or seeds according to claim 1, wherein said one or more mutations result in the tomato fruits requiring at least 2 days longer for 10% of fruits to reach the red stage compared to *Solanum lycopersicum* being homozygous for the wild type Acs4 allele.

4. The cultivated plant or seeds according to claim 1, wherein said one or more mutations result in the tomato fruits of said plant having at least a 20% reduced ethylene production compared to *Solanum lycopersicum* being homozygous for the wild type Acs4 allele.

5. The cultivated plant or seeds according to claim 1, wherein said mutant acs4 protein has functional small domains.

6. The cultivated plant or seeds according to claim 1, wherein said mutant acs4 protein comprises one or more of the following amino acid substitutions: A248V, S279N, L321F, V250E, or T316I, or wherein in said mutant acs4 protein has a deletion of amino acids 204 to 476 of SEQ ID NO: 1.

7. The cultivated plant or seeds according to claim 1, wherein the plant is an F1 hybrid plant.

8. Seeds from which a plant according to claim 1, can be grown.

9. A method for producing a hybrid *Solanum lycopersicum* plant, said method comprising:
crossing a *Solanum lycopersicum* plant obtained from seeds according to claim 8 with a second *Solanum lycopersicum* plant to obtain hybrid seeds;
wherein said hybrid *Solanum lycopersicum* plant grown from said hybrid seeds comprises an ACS4 allele having one or more mutations wherein said mutations result in production of a mutant acs4 protein having loss-of-function or reduced function compared to wild type Acs4 protein, wherein said mutant acs4 protein comprises one or more amino acid changes at Ala248, Ser279, Leu321, Val250, or Thr316; or wherein said mutant acs4 protein has a deletion of amino acids 204 to 476 of SEQ ID NO: 1.

10. A method for producing a hybrid *Solanum lycopersicum* plant, said method comprising:
crossing the *Solanum lycopersicum* plant of claim 1 with a second *Solanum lycopersicum* plant to obtain hybrid seeds;
wherein said hybrid *Solanum lycopersicum* plant grown from said hybrid seeds comprises an acs4 allele having one or more mutations wherein said one or more mutations result in production of a mutant acs4 protein having loss-of-function or reduced function compared to wild type Acs4 protein, wherein said mutant acs4 protein comprises one or more amino acid changes at Ala248, Ser279, Leu321, Val250, or Thr316; or wherein said mutant acs4 protein has a deletion of amino acids 204 to 476 of SEQ ID NO: 1.

11. A method of producing an F1 hybrid *Solanum lycopersicum* plant, comprising growing hybrid seeds obtained from crossing the *Solanum lycopersicum* plant of claim 1 with a second *Solanum lycopersicum* plant to produce an F1 hybrid plant, wherein said F1 hybrid plant comprises an acs4 allele having one or more mutations wherein said one or more mutations result in production of a mutant acs4 protein having loss-of-function or reduced function compared to wild type Acs4 protein, wherein said mutant acs4 protein comprises one or more amino acid changes at Ala248, Ser279, Leu321, Val250, or Thr316; or wherein said mutant acs4 protein has a deletion of amino acids 204 to 476 of SEQ ID NO: 1.

12. The cultivated plant or seeds according to claim 1, wherein the acs4 allele having one or more mutations is the allele as found in seed deposited under accession number NCIMB 42034, NCIMB 42037, NCIMB 42038, NCIMB 42039, or NCIMB 42041.

13. The cultivated plant or seeds according to claim 1, wherein the acs4 allele having one or more mutations is homozygous.

14. The cultivated plant according to claim 1, wherein said mutant acs4 protein comprises the amino acid substitution A248V.

15. The cultivated plant according to claim 1, wherein said mutant acs4 protein comprises the amino acid substitution S279N.

16. The cultivated plant according to claim 1, wherein said mutant acs4 protein comprises the amino acid substitution L321F.

17. The cultivated plant according to claim 1, wherein said mutant acs4 protein comprises the amino acid substitution V250E.

18. The cultivated plant according to claim 1, wherein said mutant acs4 protein comprises the amino acid substitution T316I.

19. The cultivated plant according to claim 1, wherein said mutant acs4 protein has a deletion of amino acids 204 to 476 of SEQ ID NO: 1.

20. The cultivated plant according to claim 1, wherein the acs4 allele having one or more mutations comprises one or more of the following nucleotide substitution G836A, C743T, A610T, G963T, T749A, and C947T of SEQ ID NO: 8.

21. Tomato fruit, seeds, pollen, plant parts, or progeny of a cultivated plant of the species *Solanum lycopersicum* comprising an acs4 allele having one or more mutations, said one or more mutations resulting in the production of a mutant acs4 protein having loss-of-function or reduced function compared to wild type Acs4 protein, wherein said mutant acs4 protein comprises one or more amino acid changes at Ala248, Ser279, Leu321, Val250, or Thr316; or wherein said mutant acs4 protein has a deletion of amino acids 204 to 476 of SEQ ID NO: 1.

22. The tomato fruit of claim 21, wherein the tomato fruit has reduced ethylene production and/or delayed ripening and/or an increased shelf life compared to fruits from *Solanum lycopersicum* plants being homozygous for the wild type Acs4 allele.

23. The tomato fruit according to claim 22, wherein the shelf life is at least 2 days longer than the shelf life of a tomato fruit being homozygous for the wild type Acs4 allele.

24. The tomato fruit according to claim 22, wherein the reduced ethylene production is at least 15% reduced compared to *Solanum lycopersicum* being homozygous for the wild type Acs4 allele.

25. Food or food products comprising fruits according to claim 21 or fruit parts of said fruit.

* * * * *

SEQUENCE LISTING

<160> NUMBER OF SEQ ID NOS: 21

<210> SEQ ID NO 1
<211> LENGTH: 476
<212> TYPE: PRT

-continued

<213> ORGANISM: Lycopersicon esculentum

<400> SEQUENCE: 1

```
Met Asp Leu Glu Thr Ser Glu Ile Ser Asn Tyr Lys Ser Ser Val Val
1               5                   10                  15
Leu Ser Lys Leu Ala Ser Asn Glu Gln His Gly Glu Asn Ser Pro Tyr
            20                  25                  30
Phe Asp Gly Trp Lys Ala Tyr Asp Asn Asp Pro Phe His Leu Val Asn
        35                  40                  45
Asn Leu Asn Gly Val Ile Gln Met Gly Leu Ala Glu Asn Gln Leu Ser
    50                  55                  60
Val Asp Leu Ile Glu Glu Trp Ile Lys Arg Asn Pro Lys Ala Ser Ile
65                  70                  75                  80
Cys Thr Asn Asp Gly Ile Glu Ser Phe Arg Arg Ile Ala Asn Phe Gln
                85                  90                  95
Asp Tyr His Gly Leu Pro Glu Phe Thr Asn Ala Ile Ala Lys Phe Met
            100                 105                 110
Glu Lys Thr Arg Gly Gly Lys Val Lys Phe Asp Ala Lys Arg Val Val
        115                 120                 125
Met Ala Gly Gly Ala Thr Gly Ala Asn Glu Thr Leu Ile Leu Cys Leu
    130                 135                 140
Ala Asp Pro Gly Asp Ala Phe Leu Val Pro Thr Pro Tyr Tyr Pro Gly
145                 150                 155                 160
Phe Asn Arg Asp Leu Arg Trp Arg Ser Gly Val Gln Leu Leu Pro Ile
                165                 170                 175
Ser Cys Lys Ser Cys Asn Asn Phe Lys Ile Thr Ile Glu Ala Ile Glu
            180                 185                 190
Glu Ala Tyr Glu Lys Gly Gln Gln Ala Asn Val Lys Ile Lys Gly Leu
        195                 200                 205
Ile Leu Thr Asn Pro Cys Asn Pro Leu Gly Thr Ile Leu Asp Arg Asp
    210                 215                 220
Thr Leu Lys Lys Ile Ser Thr Phe Thr Asn Glu His Asn Ile His Leu
225                 230                 235                 240
Val Cys Asp Glu Ile Tyr Ala Ala Thr Val Phe Asn Ser Pro Lys Phe
                245                 250                 255
Val Ser Ile Ala Glu Ile Ile Asn Glu Asp Asn Cys Ile Asn Lys Asp
            260                 265                 270
Leu Val His Ile Val Ser Ser Leu Ser Lys Asp Leu Gly Phe Pro Gly
        275                 280                 285
Phe Arg Val Gly Ile Val Tyr Ser Phe Asn Asp Asp Val Val Asn Cys
    290                 295                 300
Ala Arg Lys Met Ser Ser Phe Gly Leu Val Ser Thr Gln Thr Gln His
305                 310                 315                 320
Leu Leu Ala Phe Met Leu Ser Asp Asp Glu Phe Val Glu Glu Phe Leu
                325                 330                 335
Ile Glu Ser Ala Lys Arg Leu Arg Glu Arg Tyr Glu Lys Phe Thr Arg
            340                 345                 350
Gly Leu Glu Glu Ile Gly Ile Lys Cys Leu Glu Ser Asn Ala Gly Val
        355                 360                 365
Tyr Cys Trp Met Asp Leu Arg Ser Leu Leu Lys Glu Ala Thr Leu Asp
    370                 375                 380
Ala Glu Met Ser Leu Trp Lys Leu Ile Ile Asn Glu Val Lys Leu Asn
385                 390                 395                 400
```

Val Ser Pro Gly Ser Ser Phe Asn Cys Ser Glu Val Gly Trp Phe Arg
            405                 410                 415

Val Cys Phe Ala Asn Ile Asp Asp Gln Thr Met Glu Ile Ala Leu Ala
        420                 425                 430

Arg Ile Arg Met Phe Met Asp Ala Tyr Asn Asn Val Asn Lys Asn Gly
            435                 440                 445

Val Met Lys Asn Lys His Asn Gly Arg Gly Thr Thr Tyr Asp Leu Thr
450                 455                 460

Pro Gln Met Gly Ser Thr Met Lys Met Leu Leu Ala
465                 470                 475

<210> SEQ ID NO 2
<211> LENGTH: 476
<212> TYPE: PRT
<213> ORGANISM: Lycopersicon esculentum

<400> SEQUENCE: 2

Met Asp Leu Glu Thr Ser Glu Ile Ser Asn Tyr Lys Ser Ser Val Val
1               5                   10                  15

Leu Ser Lys Leu Ala Ser Asn Glu Gln His Gly Glu Asn Ser Pro Tyr
            20                  25                  30

Phe Asp Gly Trp Lys Ala Tyr Asp Asn Asp Pro His Phe Leu Val Asn
        35                  40                  45

Asn Leu Asn Gly Val Ile Gln Met Gly Leu Ala Glu Asn Gln Leu Ser
    50                  55                  60

Val Asp Leu Ile Glu Glu Trp Ile Lys Arg Asn Pro Lys Ala Ser Ile
65                  70                  75                  80

Cys Thr Asn Asp Gly Ile Glu Ser Phe Arg Arg Ile Ala Asn Phe Gln
                85                  90                  95

Asp Tyr His Gly Leu Pro Glu Phe Thr Asn Ala Ile Ala Lys Phe Met
            100                 105                 110

Glu Lys Thr Arg Gly Gly Lys Val Lys Phe Asp Ala Lys Arg Val Val
        115                 120                 125

Met Ala Gly Gly Ala Thr Gly Ala Asn Glu Thr Leu Ile Leu Cys Leu
    130                 135                 140

Ala Asp Pro Gly Asp Ala Phe Leu Val Pro Thr Pro Tyr Tyr Pro Gly
145                 150                 155                 160

Phe Asn Arg Asp Leu Arg Trp Arg Ser Gly Val Gln Leu Leu Pro Ile
                165                 170                 175

Ser Cys Lys Ser Cys Asn Asn Phe Lys Ile Thr Ile Glu Ala Ile Glu
            180                 185                 190

Glu Ala Tyr Glu Lys Gly Gln Gln Ala Asn Val Lys Ile Lys Gly Leu
        195                 200                 205

Ile Leu Thr Asn Pro Cys Asn Pro Leu Gly Thr Ile Leu Asp Arg Asp
    210                 215                 220

Thr Leu Lys Lys Ile Ser Thr Phe Thr Asn Glu His Asn Ile His Leu
225                 230                 235                 240

Val Cys Asp Glu Ile Tyr Ala Ala Thr Val Phe Asn Ser Pro Lys Phe
                245                 250                 255

Val Ser Ile Ala Glu Ile Ile Asn Glu Asp Asn Cys Ile Asn Lys Asp
            260                 265                 270

Leu Val His Ile Val Ser Asn Leu Ser Lys Asp Leu Gly Phe Pro Gly
        275                 280                 285

Phe Arg Val Gly Ile Val Tyr Ser Phe Asn Asp Asp Val Val Asn Cys
    290                 295                 300

```
Ala Arg Lys Met Ser Ser Phe Gly Leu Val Ser Thr Gln Thr Gln His
305                 310                 315                 320

Leu Leu Ala Phe Met Leu Ser Asp Asp Glu Phe Val Glu Glu Phe Leu
                325                 330                 335

Ile Glu Ser Ala Lys Arg Leu Arg Glu Arg Tyr Glu Lys Phe Thr Arg
            340                 345                 350

Gly Leu Glu Glu Ile Gly Ile Lys Cys Leu Glu Ser Asn Ala Gly Val
        355                 360                 365

Tyr Cys Trp Met Asp Leu Arg Ser Leu Leu Lys Glu Ala Thr Leu Asp
    370                 375                 380

Ala Glu Met Ser Leu Trp Lys Leu Ile Ile Asn Glu Val Lys Leu Asn
385                 390                 395                 400

Val Ser Pro Gly Ser Ser Phe Asn Cys Ser Glu Val Gly Trp Phe Arg
                405                 410                 415

Val Cys Phe Ala Asn Ile Asp Asp Gln Thr Met Glu Ile Ala Leu Ala
            420                 425                 430

Arg Ile Arg Met Phe Met Asp Ala Tyr Asn Asn Val Asn Lys Asn Gly
        435                 440                 445

Val Met Lys Asn Lys His Asn Gly Arg Gly Thr Thr Tyr Asp Leu Thr
    450                 455                 460

Pro Gln Met Gly Ser Thr Met Lys Met Leu Leu Ala
465                 470                 475

<210> SEQ ID NO 3
<211> LENGTH: 476
<212> TYPE: PRT
<213> ORGANISM: Lycopersicon esculentum

<400> SEQUENCE: 3

Met Asp Leu Glu Thr Ser Glu Ile Ser Asn Tyr Lys Ser Ser Val Val
1               5                   10                  15

Leu Ser Lys Leu Ala Ser Asn Glu Gln His Gly Glu Asn Ser Pro Tyr
            20                  25                  30

Phe Asp Gly Trp Lys Ala Tyr Asp Asn Asp Pro Phe His Leu Val Asn
        35                  40                  45

Asn Leu Asn Gly Val Ile Gln Met Gly Leu Ala Glu Asn Gln Leu Ser
    50                  55                  60

Val Asp Leu Ile Glu Glu Trp Ile Lys Arg Asn Pro Lys Ala Ser Ile
65                  70                  75                  80

Cys Thr Asn Asp Gly Ile Glu Ser Phe Arg Arg Ile Ala Asn Phe Gln
                85                  90                  95

Asp Tyr His Gly Leu Pro Glu Phe Thr Asn Ala Ile Ala Lys Phe Met
            100                 105                 110

Glu Lys Thr Arg Gly Gly Lys Val Lys Phe Asp Ala Lys Arg Val Val
        115                 120                 125

Met Ala Gly Gly Ala Thr Gly Ala Asn Glu Thr Leu Ile Leu Cys Leu
    130                 135                 140

Ala Asp Pro Gly Asp Ala Phe Leu Val Pro Thr Pro Tyr Tyr Pro Gly
145                 150                 155                 160

Phe Asn Arg Asp Leu Arg Trp Arg Ser Gly Val Gln Leu Leu Pro Ile
                165                 170                 175

Ser Cys Lys Ser Cys Asn Asn Phe Lys Ile Thr Ile Glu Ala Ile Glu
            180                 185                 190

Glu Ala Tyr Glu Lys Gly Gln Gln Ala Asn Val Lys Ile Lys Gly Leu
```

```
            195                 200                 205
Ile Leu Thr Asn Pro Cys Asn Pro Leu Gly Thr Ile Leu Asp Arg Asp
    210                 215                 220

Thr Leu Lys Lys Ile Ser Thr Phe Thr Asn Glu His Asn Ile His Leu
225                 230                 235                 240

Val Cys Asp Glu Ile Tyr Ala Val Thr Val Phe Asn Ser Pro Lys Phe
                245                 250                 255

Val Ser Ile Ala Glu Ile Ile Asn Glu Asp Asn Cys Ile Asn Lys Asp
                260                 265                 270

Leu Val His Ile Val Ser Ser Leu Ser Lys Asp Leu Gly Phe Pro Gly
            275                 280                 285

Phe Arg Val Gly Ile Val Tyr Ser Phe Asn Asp Asp Val Val Asn Cys
290                 295                 300

Ala Arg Lys Met Ser Ser Phe Gly Leu Val Ser Thr Gln Thr Gln His
305                 310                 315                 320

Leu Leu Ala Phe Met Leu Ser Asp Asp Glu Phe Val Glu Glu Phe Leu
                325                 330                 335

Ile Glu Ser Ala Lys Arg Leu Arg Glu Arg Tyr Glu Lys Phe Thr Arg
                340                 345                 350

Gly Leu Glu Glu Ile Gly Ile Lys Cys Leu Glu Ser Asn Ala Gly Val
            355                 360                 365

Tyr Cys Trp Met Asp Leu Arg Ser Leu Leu Lys Glu Ala Thr Leu Asp
    370                 375                 380

Ala Glu Met Ser Leu Trp Lys Leu Ile Ile Asn Glu Val Lys Leu Asn
385                 390                 395                 400

Val Ser Pro Gly Ser Ser Phe Asn Cys Ser Glu Val Gly Trp Phe Arg
                405                 410                 415

Val Cys Phe Ala Asn Ile Asp Asp Gln Thr Met Glu Ile Ala Leu Ala
                420                 425                 430

Arg Ile Arg Met Phe Met Asp Ala Tyr Asn Asn Val Asn Lys Asn Gly
            435                 440                 445

Val Met Lys Asn Lys His Asn Gly Arg Gly Thr Thr Tyr Asp Leu Thr
    450                 455                 460

Pro Gln Met Gly Ser Thr Met Lys Met Leu Leu Ala
465                 470                 475

<210> SEQ ID NO 4
<211> LENGTH: 203
<212> TYPE: PRT
<213> ORGANISM: Lycopersicon esculentum

<400> SEQUENCE: 4

Met Asp Leu Glu Thr Ser Glu Ile Ser Asn Tyr Lys Ser Ser Val Val
1               5                   10                  15

Leu Ser Lys Leu Ala Ser Asn Glu Gln His Gly Glu Asn Ser Pro Tyr
            20                  25                  30

Phe Asp Gly Trp Lys Ala Tyr Asp Asn Asp Pro Phe His Leu Val Asn
        35                  40                  45

Asn Leu Asn Gly Val Ile Gln Met Gly Leu Ala Glu Asn Gln Leu Ser
    50                  55                  60

Val Asp Leu Ile Glu Glu Trp Ile Lys Arg Asn Pro Lys Ala Ser Ile
65                  70                  75                  80

Cys Thr Asn Asp Gly Ile Glu Ser Phe Arg Arg Ile Ala Asn Phe Gln
                85                  90                  95
```

```
Asp Tyr His Gly Leu Pro Glu Phe Thr Asn Ala Ile Ala Lys Phe Met
            100                 105                 110

Glu Lys Thr Arg Gly Gly Lys Val Lys Phe Asp Ala Lys Arg Val Val
            115                 120                 125

Met Ala Gly Gly Ala Thr Gly Ala Asn Glu Thr Leu Ile Leu Cys Leu
        130                 135                 140

Ala Asp Pro Gly Asp Ala Phe Leu Val Pro Thr Pro Tyr Tyr Pro Gly
145                 150                 155                 160

Phe Asn Arg Asp Leu Arg Trp Arg Ser Gly Val Gln Leu Leu Pro Ile
            165                 170                 175

Ser Cys Lys Ser Cys Asn Asn Phe Lys Ile Thr Ile Glu Ala Ile Glu
            180                 185                 190

Glu Ala Tyr Glu Lys Gly Gln Gln Ala Asn Val
            195                 200

<210> SEQ ID NO 5
<211> LENGTH: 476
<212> TYPE: PRT
<213> ORGANISM: Lycopersicon esculentum

<400> SEQUENCE: 5

Met Asp Leu Glu Thr Ser Glu Ile Ser Asn Tyr Lys Ser Ser Val Val
1               5                   10                  15

Leu Ser Lys Leu Ala Ser Asn Glu Gln His Gly Glu Asn Ser Pro Tyr
            20                  25                  30

Phe Asp Gly Trp Lys Ala Tyr Asp Asn Asp Pro Phe His Leu Val Asn
        35                  40                  45

Asn Leu Asn Gly Val Ile Gln Met Gly Leu Ala Glu Asn Gln Leu Ser
    50                  55                  60

Val Asp Leu Ile Glu Glu Trp Ile Lys Arg Asn Pro Lys Ala Ser Ile
65                  70                  75                  80

Cys Thr Asn Asp Gly Ile Glu Ser Phe Arg Arg Ile Ala Asn Phe Gln
            85                  90                  95

Asp Tyr His Gly Leu Pro Glu Phe Thr Asn Ala Ile Ala Lys Phe Met
            100                 105                 110

Glu Lys Thr Arg Gly Gly Lys Val Lys Phe Asp Ala Lys Arg Val Val
            115                 120                 125

Met Ala Gly Gly Ala Thr Gly Ala Asn Glu Thr Leu Ile Leu Cys Leu
        130                 135                 140

Ala Asp Pro Gly Asp Ala Phe Leu Val Pro Thr Pro Tyr Tyr Pro Gly
145                 150                 155                 160

Phe Asn Arg Asp Leu Arg Trp Arg Ser Gly Val Gln Leu Leu Pro Ile
            165                 170                 175

Ser Cys Lys Ser Cys Asn Asn Phe Lys Ile Thr Ile Glu Ala Ile Glu
            180                 185                 190

Glu Ala Tyr Glu Lys Gly Gln Gln Ala Asn Val Lys Ile Lys Gly Leu
            195                 200                 205

Ile Leu Thr Asn Pro Cys Asn Pro Leu Gly Thr Ile Leu Asp Arg Asp
        210                 215                 220

Thr Leu Lys Lys Ile Ser Thr Phe Thr Asn Glu His Asn Ile His Leu
225                 230                 235                 240

Val Cys Asp Glu Ile Tyr Ala Ala Thr Val Phe Asn Ser Pro Lys Phe
            245                 250                 255

Val Ser Ile Ala Glu Ile Ile Asn Glu Asp Asn Cys Ile Asn Lys Asp
            260                 265                 270
```

```
Leu Val His Ile Val Ser Ser Leu Ser Lys Asp Leu Gly Phe Pro Gly
            275                 280                 285

Phe Arg Val Gly Ile Val Tyr Ser Phe Asn Asp Asp Val Val Asn Cys
        290                 295                 300

Ala Arg Lys Met Ser Ser Phe Gly Leu Val Ser Thr Gln Thr Gln His
305                 310                 315                 320

Phe Leu Ala Phe Met Leu Ser Asp Asp Glu Phe Val Glu Glu Phe Leu
                325                 330                 335

Ile Glu Ser Ala Lys Arg Leu Arg Glu Arg Tyr Glu Lys Phe Thr Arg
                340                 345                 350

Gly Leu Glu Glu Ile Gly Ile Lys Cys Leu Glu Ser Asn Ala Gly Val
                355                 360                 365

Tyr Cys Trp Met Asp Leu Arg Ser Leu Leu Lys Glu Ala Thr Leu Asp
        370                 375                 380

Ala Glu Met Ser Leu Trp Lys Leu Ile Ile Asn Glu Val Lys Leu Asn
385                 390                 395                 400

Val Ser Pro Gly Ser Ser Phe Asn Cys Ser Glu Val Gly Trp Phe Arg
                405                 410                 415

Val Cys Phe Ala Asn Ile Asp Asp Gln Thr Met Glu Ile Ala Leu Ala
                420                 425                 430

Arg Ile Arg Met Phe Met Asp Ala Tyr Asn Asn Val Asn Lys Asn Gly
                435                 440                 445

Val Met Lys Asn Lys His Asn Gly Arg Gly Thr Thr Tyr Asp Leu Thr
450                 455                 460

Pro Gln Met Gly Ser Thr Met Lys Met Leu Leu Ala
465                 470                 475

<210> SEQ ID NO 6
<211> LENGTH: 476
<212> TYPE: PRT
<213> ORGANISM: Lycopersicon esculentum

<400> SEQUENCE: 6

Met Asp Leu Glu Thr Ser Glu Ile Ser Asn Tyr Lys Ser Ser Val Val
1               5                   10                  15

Leu Ser Lys Leu Ala Ser Asn Glu Gln His Gly Glu Asn Ser Pro Tyr
                20                  25                  30

Phe Asp Gly Trp Lys Ala Tyr Asp Asn Asp Pro Phe His Leu Val Asn
            35                  40                  45

Asn Leu Asn Gly Val Ile Gln Met Gly Leu Ala Glu Asn Gln Leu Ser
        50                  55                  60

Val Asp Leu Ile Glu Glu Trp Ile Lys Arg Asn Pro Lys Ala Ser Ile
65                  70                  75                  80

Cys Thr Asn Asp Gly Ile Glu Ser Phe Arg Arg Ile Ala Asn Phe Gln
                85                  90                  95

Asp Tyr His Gly Leu Pro Glu Phe Thr Asn Ala Ile Ala Lys Phe Met
                100                 105                 110

Glu Lys Thr Arg Gly Gly Lys Val Lys Phe Asp Ala Lys Arg Val Val
            115                 120                 125

Met Ala Gly Gly Ala Thr Gly Ala Asn Glu Thr Leu Ile Leu Cys Leu
        130                 135                 140

Ala Asp Pro Gly Asp Ala Phe Leu Val Pro Thr Pro Tyr Tyr Pro Gly
145                 150                 155                 160

Phe Asn Arg Asp Leu Arg Trp Arg Ser Gly Val Gln Leu Leu Pro Ile
```

-continued

```
                165                 170                 175
Ser Cys Lys Ser Cys Asn Asn Phe Lys Ile Thr Ile Glu Ala Ile Glu
            180                 185                 190

Glu Ala Tyr Glu Lys Gly Gln Gln Ala Asn Val Lys Ile Lys Gly Leu
        195                 200                 205

Ile Leu Thr Asn Pro Cys Asn Pro Leu Gly Thr Ile Leu Asp Arg Asp
    210                 215                 220

Thr Leu Lys Lys Ile Ser Thr Phe Thr Asn Glu His Asn Ile His Leu
225                 230                 235                 240

Val Cys Asp Glu Ile Tyr Ala Ala Thr Glu Phe Asn Ser Pro Lys Phe
                245                 250                 255

Val Ser Ile Ala Glu Ile Ile Asn Glu Asp Asn Cys Ile Asn Lys Asp
            260                 265                 270

Leu Val His Ile Val Ser Ser Leu Ser Lys Asp Leu Gly Phe Pro Gly
        275                 280                 285

Phe Arg Val Gly Ile Val Tyr Ser Phe Asn Asp Val Val Asn Cys
    290                 295                 300

Ala Arg Lys Met Ser Ser Phe Gly Leu Val Ser Thr Gln Thr Gln His
305                 310                 315                 320

Leu Leu Ala Phe Met Leu Ser Asp Asp Glu Phe Val Glu Glu Phe Leu
                325                 330                 335

Ile Glu Ser Ala Lys Arg Leu Arg Glu Arg Tyr Glu Lys Phe Thr Arg
            340                 345                 350

Gly Leu Glu Glu Ile Gly Ile Lys Cys Leu Glu Ser Asn Ala Gly Val
        355                 360                 365

Tyr Cys Trp Met Asp Leu Arg Ser Leu Leu Lys Glu Ala Thr Leu Asp
    370                 375                 380

Ala Glu Met Ser Leu Trp Lys Leu Ile Ile Asn Glu Val Lys Leu Asn
385                 390                 395                 400

Val Ser Pro Gly Ser Ser Phe Asn Cys Ser Glu Val Gly Trp Phe Arg
                405                 410                 415

Val Cys Phe Ala Asn Ile Asp Asp Gln Thr Met Glu Ile Ala Leu Ala
            420                 425                 430

Arg Ile Arg Met Phe Met Asp Ala Tyr Asn Asn Val Asn Lys Asn Gly
        435                 440                 445

Val Met Lys Asn Lys His Asn Gly Arg Gly Thr Thr Tyr Asp Leu Thr
    450                 455                 460

Pro Gln Met Gly Ser Thr Met Lys Met Leu Leu Ala
465                 470                 475
```

<210> SEQ ID NO 7
<211> LENGTH: 476
<212> TYPE: PRT
<213> ORGANISM: Lycopersicon esculentum

<400> SEQUENCE: 7

```
Met Asp Leu Glu Thr Ser Glu Ile Ser Asn Tyr Lys Ser Ser Val Val
1               5                   10                  15

Leu Ser Lys Leu Ala Ser Asn Glu Gln His Gly Glu Asn Ser Pro Tyr
            20                  25                  30

Phe Asp Gly Trp Lys Ala Tyr Asp Asn Asp Pro Phe His Leu Val Asn
        35                  40                  45

Asn Leu Asn Gly Val Ile Gln Met Gly Leu Ala Glu Asn Gln Leu Ser
    50                  55                  60
```

-continued

| | | | | | | | | | | | | | | | |
|---|---|---|---|---|---|---|---|---|---|---|---|---|---|---|---|
|Val|Asp|Leu|Ile|Glu|Glu|Trp|Ile|Lys|Arg|Asn|Pro|Lys|Ala|Ser|Ile|
|65| | | | |70| | | |75| | | |80| | |

Cys Thr Asn Asp Gly Ile Glu Ser Phe Arg Arg Ile Ala Asn Phe Gln
              85                  90                 95

Asp Tyr His Gly Leu Pro Glu Phe Thr Asn Ala Ile Ala Lys Phe Met
         100                 105                110

Glu Lys Thr Arg Gly Gly Lys Val Lys Phe Asp Ala Lys Arg Val Val
         115                 120                125

Met Ala Gly Gly Ala Thr Gly Ala Asn Glu Thr Leu Ile Leu Cys Leu
130              135                 140

Ala Asp Pro Gly Asp Ala Phe Leu Val Pro Thr Pro Tyr Tyr Pro Gly
145              150                 155                160

Phe Asn Arg Asp Leu Arg Trp Arg Ser Gly Val Gln Leu Leu Pro Ile
             165                 170                 175

Ser Cys Lys Ser Cys Asn Asn Phe Lys Ile Thr Ile Glu Ala Ile Glu
             180                 185                 190

Glu Ala Tyr Glu Lys Gly Gln Gln Ala Asn Val Lys Ile Lys Gly Leu
             195                 200                 205

Ile Leu Thr Asn Pro Cys Asn Pro Leu Gly Thr Ile Leu Asp Arg Asp
210              215                 220

Thr Leu Lys Lys Ile Ser Thr Phe Thr Asn Glu His Asn Ile His Leu
225              230                 235                 240

Val Cys Asp Glu Ile Tyr Ala Ala Thr Val Phe Asn Ser Pro Lys Phe
             245                 250                 255

Val Ser Ile Ala Glu Ile Asn Glu Asp Asn Cys Ile Asn Lys Asp
             260                 265                 270

Leu Val His Ile Val Ser Ser Leu Ser Lys Asp Leu Gly Phe Pro Gly
             275                 280                 285

Phe Arg Val Gly Ile Val Tyr Ser Phe Asn Asp Asp Val Val Asn Cys
             290                 295                 300

Ala Arg Lys Met Ser Ser Phe Gly Leu Val Ser Ile Gln Thr Gln His
305              310                 315                 320

Leu Leu Ala Phe Met Leu Ser Asp Asp Glu Phe Val Glu Glu Phe Leu
             325                 330                 335

Ile Glu Ser Ala Lys Arg Leu Arg Glu Arg Tyr Glu Lys Phe Thr Arg
             340                 345                 350

Gly Leu Glu Glu Ile Gly Ile Lys Cys Leu Glu Ser Asn Ala Gly Val
             355                 360                 365

Tyr Cys Trp Met Asp Leu Arg Ser Leu Leu Lys Glu Ala Thr Leu Asp
370              375                 380

Ala Glu Met Ser Leu Trp Lys Leu Ile Ile Asn Glu Val Lys Leu Asn
385              390                 395                 400

Val Ser Pro Gly Ser Ser Phe Asn Cys Ser Glu Val Gly Trp Phe Arg
             405                 410                 415

Val Cys Phe Ala Asn Ile Asp Asp Gln Thr Met Glu Ile Ala Leu Ala
             420                 425                 430

Arg Ile Arg Met Phe Met Asp Ala Tyr Asn Asn Val Asn Lys Asn Gly
             435                 440                 445

Val Met Lys Asn Lys His Asn Gly Arg Gly Thr Thr Tyr Asp Leu Thr
             450                 455                 460

Pro Gln Met Gly Ser Thr Met Lys Met Leu Leu Ala
465              470                 475

<210> SEQ ID NO 8
<211> LENGTH: 1431
<212> TYPE: DNA
<213> ORGANISM: Lycopersicon esculentum

<400> SEQUENCE: 8

| | | | | | |
|---|---|---|---|---|---|
| atggatttgg | agacgagtga | gatttcaaat | tacaagtcat | cagtagtttt | gtctaagttg | 60 |
| gctagtaacg | aacaacatgg | tgaaaactca | ccatattttg | atgggtggaa | agcatacgat | 120 |
| aacgatcctt | tccacttggt | gaataatttg | aatggggtta | ttcagatggg | tctcgcggaa | 180 |
| aatcagcttt | cagttgactt | gattgaagaa | tggattaaga | gaaatccaaa | agcttccatt | 240 |
| tgtacaaatg | atggaattga | atctttcagg | agaattgcca | actttcaaga | ttatcatgga | 300 |
| ttgcctgaat | tcacaaatgc | gattgcaaaa | tttatggaga | aaacaagagg | tggtaaggtt | 360 |
| aagtttgatg | ctaaacgtgt | agtaatggct | ggtggagcta | ctggagctaa | tgagactctc | 420 |
| atactttgtt | tggctgatcc | tggtgatgct | tttttagtcc | ccacacccta | ttacccagga | 480 |
| tttaataggg | acctaaggtg | gagaagtggt | gtacaacttt | taccaatttc | atgcaagagt | 540 |
| tgcaataatt | tcaaaattac | aatagaagct | atcgaagagg | cctatgaaaa | aggtcaacaa | 600 |
| gcaaatgtca | aaatcaaagg | cttgattttg | accaacccct | gtaatccatt | aggtaccatt | 660 |
| ttagataggg | acacacttaa | aaaaatctcc | accttcacta | acgaacataa | tatccatctt | 720 |
| gtttgcgacg | aaatatatgc | tgctaccgtg | ttcaattctc | caaaattcgt | tagcatcgct | 780 |
| gaaattatca | acgaagataa | ttgtatcaat | aaagatttag | tacacattgt | gtctagtctt | 840 |
| tccaaggact | taggttttcc | aggatttcga | gtgggaattg | tgtactcatt | caacgatgat | 900 |
| gttgttaact | gtgctagaaa | aatgtcgagt | tttggtcttg | tttcgactca | gacacaacat | 960 |
| ttgctagctt | tcatgttgtc | tgacgatgaa | tttgtggaag | aatttcttat | tgaaagcgcg | 1020 |
| aaaaggttga | gagaaggta | cgagaaattc | actagaggac | ttgaagaaat | aggaatcaag | 1080 |
| tgcttagaaa | gcaatgcagg | ggtttattgt | tggatggatt | tgcggtcatt | gttgaaagaa | 1140 |
| gcaacactag | atgctgagat | gtcactttgg | aaactcatca | taaacgaagt | taagctcaac | 1200 |
| gtctcccctg | gatcttcgtt | caattgctcg | gaggtaggat | ggtttcgagt | ttgttttgca | 1260 |
| aatatcgatg | atcaaacaat | ggagatcgca | cttgcaagga | ttcggatgtt | tatggatgct | 1320 |
| tacaacaatg | ttaataaaaa | tggagtcatg | aagaacaagc | acaatggaag | aggaacaacc | 1380 |
| tacgacttaa | ctcctcaaat | ggggagtacg | atgaaaatgt | tattagctta | a | 1431 |

<210> SEQ ID NO 9
<211> LENGTH: 1431
<212> TYPE: DNA
<213> ORGANISM: Lycopersicon esculentum

<400> SEQUENCE: 9

| | | | | | |
|---|---|---|---|---|---|
| atggatttgg | agacgagtga | gatttcaaat | tacaagtcat | cagtagtttt | gtctaagttg | 60 |
| gctagtaacg | aacaacatgg | tgaaaactca | ccatattttg | atgggtggaa | agcatacgat | 120 |
| aacgatcctt | tccacttggt | gaataatttg | aatggggtta | ttcagatggg | tctcgcggaa | 180 |
| aatcagcttt | cagttgactt | gattgaagaa | tggattaaga | gaaatccaaa | agcttccatt | 240 |
| tgtacaaatg | atggaattga | atctttcagg | agaattgcca | actttcaaga | ttatcatgga | 300 |
| ttgcctgaat | tcacaaatgc | gattgcaaaa | tttatggaga | aaacaagagg | tggtaaggtt | 360 |
| aagtttgatg | ctaaacgtgt | agtaatggct | ggtggagcta | ctggagctaa | tgagactctc | 420 |
| atactttgtt | tggctgatcc | tggtgatgct | tttttagtcc | ccacacccta | ttacccagga | 480 |

```
tttaataggg acctaaggtg gagaagtggt gtacaacttt taccaatttc atgcaagagt    540
tgcaataatt tcaaaattac aatagaagct atcgaagagg cctatgaaaa aggtcaacaa    600
gcaaatgtca aaatcaaagg cttgattttg accaacccct gtaatccatt aggtaccatt    660
ttagataggg acacacttaa aaaaatctcc accttcacta acgaacataa tatccatctt    720
gtttgcgacg aaatatatgc tgctaccgtg ttcaattctc caaaattcgt tagcatcgct    780
gaaattatca acgaagataa ttgtatcaat aaagatttag tacacattgt gtctaatctt    840
tccaaggact taggttttcc aggatttcga gtgggaattg tgtactcatt caacgatgat    900
gttgttaact gtgctagaaa aatgtcgagt tttggtcttg tttcgactca gacacaacat    960
ttgctagctt tcatgttgtc tgacgatgaa tttgtggaag aatttcttat tgaaagcgcg   1020
aaaaggttga gagaaggta  cgagaaattc actagaggac ttgaagaaat aggaatcaag   1080
tgcttagaaa gcaatgcagg ggtttattgt tggatggatt tgcggtcatt gttgaaagaa   1140
gcaacactag atgctgagat gtcactttgg aaactcatca taaacgaagt taagctcaac   1200
gtctcccctg gatcttcgtt caattgctcg gaggtaggat ggtttcgagt ttgttttgca   1260
aatatcgatg atcaaacaat ggagatcgca cttgcaagga ttcggatgtt tatggatgct   1320
tacaacaatg ttaataaaaa tggagtcatg aagaacaagc acaatggaag aggaacaacc   1380
tacgacttaa ctcctcaaat ggggagtacg atgaaaatgt tattagctta a            1431

<210> SEQ ID NO 10
<211> LENGTH: 1431
<212> TYPE: DNA
<213> ORGANISM: Lycopersicon esculentum

<400> SEQUENCE: 10
atggatttgg agacgagtga gatttcaaat tacaagtcat cagtagttt  gtctaagttg     60
gctagtaacg aacaacatgg tgaaaactca ccatattttg atgggtggaa agcatacgat    120
aacgatcctt tccacttggt gaataatttg aatggggtta ttcagatggg tctcgcggaa    180
aatcagcttt cagttgactt gattgaagaa tggattaaga gaaatccaaa agcttccatt    240
tgtacaaatg atggaattga atctttcagg agaattgcca actttcaaga ttatcatgga    300
ttgcctgaat tcacaaatgc gattgcaaaa tttatggaga aaacaagagg tggtaaggtt    360
aagtttgatg ctaaacgtgt agtaatggct ggtggagcta ctggagctaa tgagactctc    420
atactttgtt tggctgatcc tggtgatgct tttttagtcc ccacacccta ttacccagga    480
tttaataggg acctaaggtg gagaagtggt gtacaacttt taccaatttc atgcaagagt    540
tgcaataatt tcaaaattac aatagaagct atcgaagagg cctatgaaaa aggtcaacaa    600
gcaaatgtca aaatcaaagg cttgattttg accaacccct gtaatccatt aggtaccatt    660
ttagataggg acacacttaa aaaaatctcc accttcacta acgaacataa tatccatctt    720
gtttgcgacg aaatatatgc tgttaccgtg ttcaattctc caaaattcgt tagcatcgct    780
gaaattatca acgaagataa ttgtatcaat aaagatttag tacacattgt gtctagtctt    840
tccaaggact taggttttcc aggatttcga gtgggaattg tgtactcatt caacgatgat    900
gttgttaact gtgctagaaa aatgtcgagt tttggtcttg tttcgactca gacacaacat    960
ttgctagctt tcatgttgtc tgacgatgaa tttgtggaag aatttcttat tgaaagcgcg   1020
aaaaggttga gagaaggta  cgagaaattc actagaggac ttgaagaaat aggaatcaag   1080
tgcttagaaa gcaatgcagg ggtttattgt tggatggatt tgcggtcatt gttgaaagaa   1140
gcaacactag atgctgagat gtcactttgg aaactcatca taaacgaagt taagctcaac   1200
```

```
gtctcccctg gatcttcgtt caattgctcg gaggtaggat ggtttcgagt ttgttttgca   1260
aatatcgatg atcaaacaat ggagatcgca cttgcaagga ttcggatgtt tatggatgct   1320
tacaacaatg ttaataaaaa tggagtcatg aagaacaagc acaatggaag aggaacaacc   1380
tacgacttaa ctcctcaaat ggggagtacg atgaaaatgt tattagctta a            1431

<210> SEQ ID NO 11
<211> LENGTH: 1431
<212> TYPE: DNA
<213> ORGANISM: Lycopersicon esculentum

<400> SEQUENCE: 11
atggatttgg agacgagtga gatttcaaat tacaagtcat cagtagtttt gtctaagttg     60
gctagtaacg aacaacatgg tgaaaactca ccatattttg atgggtggaa agcatacgat    120
aacgatcctt tccacttggt gaataatttg aatggggtta ttcagatggg tctcgcggaa    180
aatcagcttt cagttgactt gattgaagaa tggattaaga gaaatccaaa agcttccatt    240
tgtacaaatg atggaattga atctttcagg agaattgcca actttcaaga ttatcatgga    300
ttgcctgaat tcacaaatgc gattgcaaaa tttatggaga aaacaagagg tggtaaggtt    360
aagtttgatg ctaaacgtgt agtaatggct ggtggagcta ctggagctaa tgagactctc    420
atactttgtt tggctgatcc tggtgatgct ttttttagtcc ccacacccta ttacccagga    480 tttaatagggg acctaaggtg gagaagtggt gtacaactttc taccaatttc atgcaagagt    540
tgcaataatt tcaaaattac aatagaagct atcgaagagg cctatgaaaa aggtcaacaa    600
gcaaatgtct aaatcaaagg cttgattttg accaacccctt gtaatccatt aggtaccatt    660
ttagataggg acacacttaa aaaaatctcc accttcacta acgaacataa tatccatctt    720
gtttgcgacg aaatatatgc tgctaccgtg ttcaattctc caaaattcgt tagcatcgct    780
gaaattatca cgaagataa ttgtatcaat aaagatttag tacacattgt gtctagtctt    840
tccaaggact taggttttcc aggatttcga gtgggaattg tgtactcatt caacgatgat    900
gttgttaact gtgctagaaa aatgtcgagt tttggtcttg tttcgactca gacacaacat    960
ttgctagctt tcatgttgtc tgacgatgaa tttgtggaag aatttcttat tgaaagcgcg   1020
aaaaggttga gagaaggta cgagaaattc actagaggac ttgaagaaat aggaatcaag   1080
tgcttagaaa gcaatgcagg ggtttattgt tggatggatt tgcggtcatt gttgaaagaa   1140
gcaacactag atgctgagat gtcactttgg aaactcatca taaacgaagt taagctcaac   1200
gtctcccctg gatcttcgtt caattgctcg gaggtaggat ggtttcgagt ttgttttgca   1260
aatatcgatg atcaaacaat ggagatcgca cttgcaagga ttcggatgtt tatggatgct   1320
tacaacaatg ttaataaaaa tggagtcatg aagaacaagc acaatggaag aggaacaacc   1380
tacgacttaa ctcctcaaat ggggagtacg atgaaaatgt tattagctta a            1431

<210> SEQ ID NO 12
<211> LENGTH: 1431
<212> TYPE: DNA
<213> ORGANISM: Lycopersicon esculentum

<400> SEQUENCE: 12
atggatttgg agacgagtga gatttcaaat tacaagtcat cagtagtttt gtctaagttg     60
gctagtaacg aacaacatgg tgaaaactca ccatattttg atgggtggaa agcatacgat    120
aacgatcctt tccacttggt gaataatttg aatggggtta ttcagatggg tctcgcggaa    180
```

```
aatcagcttt cagttgactt gattgaagaa tggattaaga gaaatccaaa agcttccatt      240
tgtacaaatg atggaattga atctttcagg agaattgcca actttcaaga ttatcatgga      300
ttgcctgaat tcacaaatgc gattgcaaaa tttatggaga aaacaagagg tggtaaggtt      360
aagtttgatg ctaaacgtgt agtaatggct ggtggagcta ctggagctaa tgagactctc      420
atactttgtt tggctgatcc tggtgatgct ttttagtcc ccacaccta ttacccagga       480 tttaataggg acctaaggtg gagaagtggt gtacaacttt taccaatttc atgcaagagt      540
tgcaataatt tcaaaattac aatagaagct atcgaagagg cctatgaaaa aggtcaacaa      600
gcaaatgtca aaatcaaagg cttgattttg accaacccctt gtaatccatt aggtaccatt     660
ttagataggg acacacttaa aaaaatctcc accttcacta acgaacataa tatccatctt      720
gtttgcgacg aaatatatgc tgctaccgtg ttcaattctc caaaattcgt tagcatcgct      780
gaaattatca acgaagataa ttgtatcaat aaagatttag tacacattgt gtctagtctt      840
tccaaggact taggttttcc aggatttcga gtgggaattg tgtactcatt caacgatgat      900
gttgttaact gtgctagaaa aatgtcgagt tttggtcttg tttcgactca gacacaacat      960
tttctagctt tcatgttgtc tgacgatgaa tttgtggaag aatttcttat tgaaagcgcg     1020
aaaaggttga gagaaggta cgagaaattc actagaggac ttgaagaaat aggaatcaag      1080
tgcttagaaa gcaatgcagg ggtttattgt tggatggatt tgcggtcatt gttgaaagaa     1140
gcaacactag atgctgagat gtcactttgg aaactcatca taaacgaagt taagctcaac     1200
gtctcccctg gatcttcgtt caattgctcg gaggtaggat ggtttcgagt ttgttttgca     1260
aatatcgatg atcaaacaat ggagatcgca cttgcaagga ttcggatgtt tatggatgct     1320
tacaacaatg ttaataaaaa tggagtcatg aagaacaagc acaatggaag aggaacaacc     1380
tacgacttaa ctcctcaaat ggggagtacg atgaaaatgt tattagctta a              1431

<210> SEQ ID NO 13
<211> LENGTH: 1431
<212> TYPE: DNA
<213> ORGANISM: Lycopersicon esculentum

<400> SEQUENCE: 13
atggatttgg agacgagtga gatttcaaat tacaagtcat cagtagtttt gtctaagttg       60
gctagtaacg aacaacatgg tgaaaactca ccatattttg atgggtggaa agcatacgat      120
aacgatcctt tccacttggt gaataatttg aatgggggtta ttcagatggg tctcgcggaa     180
aatcagcttt cagttgactt gattgaagaa tggattaaga gaaatccaaa agcttccatt      240
tgtacaaatg atggaattga atctttcagg agaattgcca actttcaaga ttatcatgga      300
ttgcctgaat tcacaaatgc gattgcaaaa tttatggaga aaacaagagg tggtaaggtt      360
aagtttgatg ctaaacgtgt agtaatggct ggtggagcta ctggagctaa tgagactctc      420
atactttgtt tggctgatcc tggtgatgct ttttagtcc ccacaccta ttacccagga       480 tttaataggg acctaaggtg gagaagtggt gtacaacttt taccaatttc atgcaagagt      540
tgcaataatt tcaaaattac aatagaagct atcgaagagg cctatgaaaa aggtcaacaa      600
gcaaatgtca aaatcaaagg cttgattttg accaacccctt gtaatccatt aggtaccatt     660
ttagataggg acacacttaa aaaaatctcc accttcacta acgaacataa tatccatctt      720
gtttgcgacg aaatatatgc tgctaccgag ttcaattctc caaaattcgt tagcatcgct      780
gaaattatca acgaagataa ttgtatcaat aaagatttag tacacattgt gtctagtctt      840
tccaaggact taggttttcc aggatttcga gtgggaattg tgtactcatt caacgatgat      900
```

```
gttgttaact gtgctagaaa aatgtcgagt tttggtcttg tttcgactca gacacaacat    960
ttgctagctt tcatgttgtc tgacgatgaa tttgtggaag aatttcttat tgaaagcgcg   1020
aaaaggttga gagaaaggta cgagaaattc actagaggac ttgaagaaat aggaatcaag   1080
tgcttagaaa gcaatgcagg ggtttattgt tggatggatt tgcggtcatt gttgaaagaa   1140
gcaacactag atgctgagat gtcactttgg aaactcatca taaacgaagt taagctcaac   1200
gtctcccctg gatcttcgtt caattgctcg gaggtaggat ggtttcgagt ttgttttgca   1260
aatatcgatg atcaaacaat ggagatcgca cttgcaagga ttcggatgtt tatggatgct   1320
tacaacaatg ttaataaaaa tggagtcatg aagaacaagc acaatggaag aggaacaacc   1380
tacgacttaa ctcctcaaat ggggagtacg atgaaaatgt tattagctta a           1431

<210> SEQ ID NO 14
<211> LENGTH: 1431
<212> TYPE: DNA
<213> ORGANISM: Lycopersicon esculentum

<400> SEQUENCE: 14
atggatttgg agacgagtga gatttcaaat tacaagtcat cagtagtttt gtctaagttg     60
gctagtaacg aacaacatgg tgaaaactca ccatattttg atgggtggaa agcatacgat    120
aacgatcctt tccacttggt gaataatttg aatggggtta ttcagatggg tctcgcggaa    180
aatcagcttt cagttgactt gattgaagaa tggattaaga gaaatccaaa agcttccatt    240
tgtacaaatg atggaattga atctttcagg agaattgcca actttcaaga ttatcatgga    300
ttgcctgaat tcacaaatgc gattgcaaaa tttatggaga aaacaagagg tggtaaggtt    360
aagtttgatg ctaaacgtgt agtaatggct ggtggagcta ctggagctaa tgagactctc    420
atactttgtt tggctgatcc tggtgatgct ttttagtcc ccacacccta ttacccagga    480
tttaataggg acctaaggtg gagaagtggt gtacaacttt taccaatttc atgcaagagt    540
tgcaataatt tcaaaattac aatagaagct atcgaagagg cctatgaaaa aggtcaacaa    600
gcaaatgtca aaatcaaagg cttgattttg accaacccct tgtaatccatt aggtaccatt    660 ttagataggg acacacttaa aaaaatctcc accttcacta cgaacataa tatccatctt    720 gtttgcgacg aaatatatgc tgctaccgtg ttcaattctc caaaattcgt tagcatcgct    780
gaaattatca cgaagataa ttgtatcaat aaagatttag tacacattgt gtctagtctt    840
tccaaggact aggttttcc aggatttcga gtgggaattg tgtactcatt caacgatgat    900
gttgttaact gtgctagaaa aatgtcgagt tttggtcttg tttcgattca gacacaacat    960
ttgctagctt tcatgttgtc tgacgatgaa tttgtggaag aatttcttat tgaaagcgcg   1020
aaaaggttga gagaaaggta cgagaaattc actagaggac ttgaagaaat aggaatcaag   1080
tgcttagaaa gcaatgcagg ggtttattgt tggatggatt tgcggtcatt gttgaaagaa   1140
gcaacactag atgctgagat gtcactttgg aaactcatca taaacgaagt taagctcaac   1200
gtctcccctg gatcttcgtt caattgctcg gaggtaggat ggtttcgagt ttgttttgca   1260
aatatcgatg atcaaacaat ggagatcgca cttgcaagga ttcggatgtt tatggatgct   1320
tacaacaatg ttaataaaaa tggagtcatg aagaacaagc acaatggaag aggaacaacc   1380
tacgacttaa ctcctcaaat ggggagtacg atgaaaatgt tattagctta a            1431

<210> SEQ ID NO 15
<211> LENGTH: 2641
<212> TYPE: DNA
```

```
<213> ORGANISM: Lycopersicon esculentum
<220> FEATURE:
<221> NAME/KEY: exon
<222> LOCATION: (1)..(318)
<223> OTHER INFORMATION: exon1
<220> FEATURE:
<221> NAME/KEY: exon
<222> LOCATION: (796)..(955)
<223> OTHER INFORMATION: exon2
<220> FEATURE:
<221> NAME/KEY: exon
<222> LOCATION: (1689)..(2641)
<223> OTHER INFORMATION: exon2

<400> SEQUENCE: 15
```

| | | | | | | | | | | | | | | | | |
|---|---|---|---|---|---|---|---|---|---|---|---|---|---|---|---|---|
| atg | gat | ttg | gag | acg | agt | gag | att | tca | aat | tac | aag | tca | tca | gta | gtt | 48 |
| Met | Asp | Leu | Glu | Thr | Ser | Glu | Ile | Ser | Asn | Tyr | Lys | Ser | Ser | Val | Val | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ttg | tct | aag | ttg | gct | agt | aac | gaa | caa | cat | ggt | gaa | aac | tca | cca | tat | 96 |
| Leu | Ser | Lys | Leu | Ala | Ser | Asn | Glu | Gln | His | Gly | Glu | Asn | Ser | Pro | Tyr | |
| | | | 20 | | | | | 25 | | | | | 30 | | | |

| | | | | | | | | | | | | | | | | |
|---|---|---|---|---|---|---|---|---|---|---|---|---|---|---|---|---|
| ttt | gat | ggg | tgg | aaa | gca | tac | gat | aac | gat | cct | ttc | cac | ttg | gtg | aat | 144 |
| Phe | Asp | Gly | Trp | Lys | Ala | Tyr | Asp | Asn | Asp | Pro | Phe | His | Leu | Val | Asn | |
| | | 35 | | | | | 40 | | | | | 45 | | | | |

| | | | | | | | | | | | | | | | | |
|---|---|---|---|---|---|---|---|---|---|---|---|---|---|---|---|---|
| aat | ttg | aat | ggg | gtt | att | cag | atg | ggt | ctc | gcg | gaa | aat | cag | ctt | tca | 192 |
| Asn | Leu | Asn | Gly | Val | Ile | Gln | Met | Gly | Leu | Ala | Glu | Asn | Gln | Leu | Ser | |
| | 50 | | | | | 55 | | | | | 60 | | | | | |

| | | | | | | | | | | | | | | | | |
|---|---|---|---|---|---|---|---|---|---|---|---|---|---|---|---|---|
| gtt | gac | ttg | att | gaa | gaa | tgg | att | aag | aga | aat | cca | aaa | gct | tcc | att | 240 |
| Val | Asp | Leu | Ile | Glu | Glu | Trp | Ile | Lys | Arg | Asn | Pro | Lys | Ala | Ser | Ile | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| tgt | aca | aat | gat | gga | att | gaa | tct | ttc | agg | aga | att | gcc | aac | ttt | caa | 288 |
| Cys | Thr | Asn | Asp | Gly | Ile | Glu | Ser | Phe | Arg | Arg | Ile | Ala | Asn | Phe | Gln | |
| | | | | 85 | | | | | 90 | | | | | 95 | | |

| | | | | | | | | | | |
|---|---|---|---|---|---|---|---|---|---|---|
| gat | tat | cat | gga | ttg | cct | gaa | ttc | aca | aat | gtaagttttg ttatttctct | 338 |
| Asp | Tyr | His | Gly | Leu | Pro | Glu | Phe | Thr | Asn | |
| | | | 100 | | | | | 105 | | |

| | |
|---|---|
| cctttcaaaa acaaaatgtc acattaaaaa ttagtatatt tttttagtta tcctccgttc | 398 |
| aattcttaag aaatatctaa taaataaaag gattattttt cttaataggc gtgaaataaa | 458 |
| ttaaacttag acttctttta agatgaatat gaaatactta ctactattat atatgaattg | 518 |
| tagcggtgaa agtcattata aatttgtaca aaaaaaaaa agaaagttaa tgatcaattt | 578 |
| tattactata attttacatt tacttggaat aaagaactaa gattacattt agttgaaata | 638 |
| gatatatttc ttgacttcta tctcatacat atatttcatt ttatctgaca ctattttac | 698 |
| ttgtttattg aaaatttaaa aaattacata cgttattaaa ataaatatat ttttatccaa | 758 |

| | | | | | | |
|---|---|---|---|---|---|---|
| ttttttcgta taaaaaaata tttttttttt tgtgtag gcg | att | gca | aaa | ttt | atg | 813 |
| | Ala | Ile | Ala | Lys | Phe | Met | |
| | | | | | 110 | | |

| | | | | | | | | | | | | | | | | |
|---|---|---|---|---|---|---|---|---|---|---|---|---|---|---|---|---|
| gag | aaa | aca | aga | ggt | ggt | aag | gtt | aag | ttt | gat | gct | aaa | cgt | gta | gta | 861 |
| Glu | Lys | Thr | Arg | Gly | Gly | Lys | Val | Lys | Phe | Asp | Ala | Lys | Arg | Val | Val | |
| | | | 115 | | | | | 120 | | | | | 125 | | | |

| | | | | | | | | | | | | | | | | |
|---|---|---|---|---|---|---|---|---|---|---|---|---|---|---|---|---|
| atg | gct | ggt | gga | gct | act | gga | gct | aat | gag | act | ctc | ata | ctt | tgt | ttg | 909 |
| Met | Ala | Gly | Gly | Ala | Thr | Gly | Ala | Asn | Glu | Thr | Leu | Ile | Leu | Cys | Leu | |
| | | | 130 | | | | | 135 | | | | | 140 | | | |

| | | | | | | | | | | | | | | | |
|---|---|---|---|---|---|---|---|---|---|---|---|---|---|---|---|
| gct | gat | cct | ggt | gat | gct | ttt | tta | gtc | ccc | aca | ccc | tat | tac | cca | g | 955 |
| Ala | Asp | Pro | Gly | Asp | Ala | Phe | Leu | Val | Pro | Thr | Pro | Tyr | Tyr | Pro | | |
| 145 | | | | | 150 | | | | | 155 | | | | | | |

| | |
|---|---|
| ggtatgtata catatttcta aattgaattc aacttatatt atatcgatcg tgaaaaaaat | 1015 |
| agatgttct taattaaata ttaaattcct tcttgcctat ttaaaatgcg aattatatta | 1075 |
| tatcactcag ttgaccttta aaatcgatat tatataatat aatttgtatt tttcaaatta | 1135 |

-continued

```
aataagtgaa aatagtcatt taatttattt agtagataag taaaaatgga cggacgaagt    1195
atataaatac catttcaggt aattgattga ggggagattt tttttttaatg aaataacact   1255 ttagtaattt aagagagact atccgtattg gtcaaatctt tagaactaat attaatgggg   1315 gcaactttc ctacttgtga tttgtcaaaa aagttgaaaa ctaacaaaca aatgatattt    1375
ttggttctct gtctttttat tttgattaaa aaaaatgaaa ttttctcatt ttttaaaaaa   1435
aataatggat agtataaaaa ttataattac tttctttatc ctgatttatg taacatagtt   1495
tgaatttcta gacgtttcaa gtttaatttt gaatttgtat catataaaaa gtatttattt   1555 atttaaaat cgttatgatt aataattcaa atgaaaaaat tgattgactc tcgaaatttg   1615
tgattataca atgataaaat tatttaatgg cttacattgg catgtattta agtcttcatt   1675
tgtattaaat gca ga  ttt aat agg gac cta agg tgg aga agt ggt gta      1723
              Gly Phe Asn Arg Asp Leu Arg Trp Arg Ser Gly Val
                      160                 165                 170 caa ctt tta cca att tca tgc aag agt tgc aat aat ttc aaa att aca     1771
Gln Leu Leu Pro Ile Ser Cys Lys Ser Cys Asn Asn Phe Lys Ile Thr
            175                 180                 185 ata gaa gct atc gaa gag gcc tat gaa aaa ggt caa caa gca aat gtc     1819
Ile Glu Ala Ile Glu Glu Ala Tyr Glu Lys Gly Gln Gln Ala Asn Val
        190                 195                 200 aaa atc aaa ggc ttg att ttg acc aac cct tgt aat cca tta ggt acc     1867
Lys Ile Lys Gly Leu Ile Leu Thr Asn Pro Cys Asn Pro Leu Gly Thr
    205                 210                 215 att tta gat agg gac aca ctt aaa aaa atc tcc acc ttc act aac gaa     1915
Ile Leu Asp Arg Asp Thr Leu Lys Lys Ile Ser Thr Phe Thr Asn Glu
220                 225                 230                 235 cat aat atc cat ctt gtt tgc gac gaa ata tat gct gct acc gtg ttc     1963
His Asn Ile His Leu Val Cys Asp Glu Ile Tyr Ala Ala Thr Val Phe
            240                 245                 250 aat tct cca aaa ttc gtt agc atc gct gaa att atc aac gaa gat aat     2011
Asn Ser Pro Lys Phe Val Ser Ile Ala Glu Ile Ile Asn Glu Asp Asn
        255                 260                 265 tgt atc aat aaa gat tta gta cac att gtg tct agt ctt tcc aag gac     2059
Cys Ile Asn Lys Asp Leu Val His Ile Val Ser Ser Leu Ser Lys Asp
    270                 275                 280 tta ggt ttt cca gga ttt cga gtg gga att gtg tac tca ttc aac gat     2107
Leu Gly Phe Pro Gly Phe Arg Val Gly Ile Val Tyr Ser Phe Asn Asp
285                 290                 295 gat gtt gtt aac tgt gct aga aaa atg tcg agt ttt ggt ctt gtt tcg     2155
Asp Val Val Asn Cys Ala Arg Lys Met Ser Ser Phe Gly Leu Val Ser
300                 305                 310                 315 act cag aca caa cat ttg cta gct ttc atg ttg tct gac gat gaa ttt     2203
Thr Gln Thr Gln His Leu Leu Ala Phe Met Leu Ser Asp Asp Glu Phe
            320                 325                 330 gtg gaa gaa ttt ctt att gaa agc gcg aaa agg ttg aga gaa agg tac     2251
Val Glu Glu Phe Leu Ile Glu Ser Ala Lys Arg Leu Arg Glu Arg Tyr
        335                 340                 345 gag aaa ttc act aga gga ctt gaa gaa ata gga atc aag tgc tta gaa     2299
Glu Lys Phe Thr Arg Gly Leu Glu Glu Ile Gly Ile Lys Cys Leu Glu
    350                 355                 360 agc aat gca ggg gtt tat tgt tgg atg gat ttg cgg tca ttg ttg aaa     2347
Ser Asn Ala Gly Val Tyr Cys Trp Met Asp Leu Arg Ser Leu Leu Lys
365                 370                 375 gaa gca aca cta gat gct gag atg tca ctt tgg aaa ctc atc ata aac     2395
Glu Ala Thr Leu Asp Ala Glu Met Ser Leu Trp Lys Leu Ile Ile Asn
380                 385                 390                 395
```

-continued

```
gaa gtt aag ctc aac gtc tcc cct gga tct tcg ttc aat tgc tcg gag    2443
Glu Val Lys Leu Asn Val Ser Pro Gly Ser Ser Phe Asn Cys Ser Glu
            400                 405                 410 gta gga tgg ttt cga gtt tgt ttt gca aat atc gat gat caa aca atg    2491
Val Gly Trp Phe Arg Val Cys Phe Ala Asn Ile Asp Asp Gln Thr Met
        415                 420                 425 gag atc gca ctt gca agg att cgg atg ttt atg gat gct tac aac aat    2539
Glu Ile Ala Leu Ala Arg Ile Arg Met Phe Met Asp Ala Tyr Asn Asn
    430                 435                 440 gtt aat aaa aat gga gtc atg aag aac aag cac aat gga aga gga aca    2587
Val Asn Lys Asn Gly Val Met Lys Asn Lys His Asn Gly Arg Gly Thr
445                 450                 455 acc tac gac tta act cct caa atg ggg agt acg atg aaa atg tta tta    2635
Thr Tyr Asp Leu Thr Pro Gln Met Gly Ser Thr Met Lys Met Leu Leu
460                 465                 470                 475 gct taa                                                            2641
Ala
```

<210> SEQ ID NO 16
<211> LENGTH: 493
<212> TYPE: PRT
<213> ORGANISM: Cucumis melo
<300> PUBLICATION INFORMATION:
<301> AUTHORS: Capitani, et al.
<303> JOURNAL: Journal of Molecular Biology
<304> VOLUME: 194
<306> PAGES: 745-756
<307> DATE: 1999

<400> SEQUENCE: 16

```
Met Gly Phe His Gln Thr His Glu Thr Asn Gln Val Leu Leu Ser Lys
1               5                   10                  15

Ile Ala Ile Ser Asp Gly His Gly Glu Asp Ser Pro Tyr Phe Asp Gly
            20                  25                  30

Trp Lys Ala Tyr Asp Asn Asp Pro Phe His Pro Glu Asn Asn Pro Leu
        35                  40                  45

Gly Val Ile Gln Met Gly Leu Ala Glu Asn Gln Leu Ser Pro Asp Leu
    50                  55                  60

Ile Val Asp Trp Ile Arg Lys His Pro Lys Ala Ser Ile Tyr Thr Asp
65                  70                  75                  80

Glu Gly Leu Leu Asn Phe Lys Asp Ile Ala Asn Phe Gln Asp Tyr His
                85                  90                  95

Gly Leu Pro Glu Phe Arg Asn Ala Ile Ala Ser Phe Met Gly Lys Ala
            100                 105                 110

Arg Gly Gly Arg Val Lys Phe Asp Pro Ser Arg Ile Val Met Gly Gly
        115                 120                 125

Gly Ala Thr Gly Ala Ser Glu Thr Val Ile Phe Cys Leu Ala Asp Pro
    130                 135                 140

Gly Asp Ala Phe Leu Ile Pro Ser Pro Tyr Tyr Ala Ala Phe Asp Arg
145                 150                 155                 160

Asp Leu Gln Trp Arg Thr Arg Ala Gln Ile Ile Pro Val His Cys Asn
                165                 170                 175

Ser Ser Asn Asn Phe Gln Ile Thr Arg Glu Ala Leu Glu Val Ala Tyr
            180                 185                 190

Lys Lys Ala Glu Glu Ser Asn Ile Lys Val Lys Gly Leu Ile Ile Thr
        195                 200                 205

Asn Pro Ser Asn Pro Leu Gly Thr Ile Tyr Asp Arg Asp Thr Leu Lys
    210                 215                 220
```

```
Ser Leu Val Asn Phe Val Asn Asp Asn Asn Ile His Leu Ile Cys Asp
225                 230                 235                 240

Glu Ile Tyr Ser Ala Thr Val Phe Lys Ser Pro Ser Phe Thr Ser Ile
            245                 250                 255

Ala Glu Ile Ile Glu Glu Met Asp His Cys Lys Lys Glu Leu Ile His
        260                 265                 270

Ile Leu Ser Ser Leu Ser Lys Asp Met Gly Leu Pro Gly Phe Arg Val
    275                 280                 285

Gly Ile Leu Tyr Ser Tyr Asn Asp Thr Val Val Ser Ile Ala Arg Lys
290                 295                 300

Met Ser Ser Phe Gly Leu Val Ser Ser Gln Thr Gln His Leu Leu Ala
305                 310                 315                 320

Ala Met Leu Ser Asp Glu Glu Phe Val Asp Asn Phe Leu Val Glu Asn
            325                 330                 335

Ser Lys Arg Leu Ala Lys Arg His Ala Arg Phe Thr Glu Glu Leu Glu
        340                 345                 350

Lys Met Gly Ile Thr Cys Leu Asn Ser Asn Ala Gly Leu Phe Val Trp
    355                 360                 365

Met Asp Leu Arg Lys Leu Leu Lys Asp Gln Ser Phe Glu Ser Glu Met
370                 375                 380

Glu Leu Trp Arg Val Ile Ile Asn Glu Val Lys Leu Asn Val Ser Pro
385                 390                 395                 400

Gly Ser Ser Phe His Val Thr Glu Pro Gly Trp Phe Arg Val Cys Phe
            405                 410                 415

Ala Asn Met Asp Asp Asn Thr Val Gly Val Ala Leu Asp Arg Ile His
        420                 425                 430

Ser Phe Val Gly Lys Ile Asp Lys Lys Glu Asn Ser Thr Ile Pro Met
    435                 440                 445

Pro Pro Lys Lys Lys His Arg Glu Asn Lys Leu Arg Leu Ser Phe Ser
450                 455                 460

Phe Ser Gly Arg Arg Tyr Glu Glu Gly Asn Val Leu Lys Ser Pro His
465                 470                 475                 480

Met Met Ser Pro His Ser Pro Leu Val Arg Ala Lys Thr
            485                 490

<210> SEQ ID NO 17
<211> LENGTH: 482
<212> TYPE: PRT
<213> ORGANISM: Pelargonium hortorum
<300> PUBLICATION INFORMATION:
<301> AUTHORS: Capitani, et al.
<303> JOURNAL: Journal of Molecular Biology
<304> VOLUME: 194
<306> PAGES: 745-756
<307> DATE: 1999

<400> SEQUENCE: 17

Met Glu Asn Lys Ser Lys Gln Leu Leu Ser Lys Ile Ala Thr Asn Asp
1               5                   10                  15

Gly His Gly Glu Asn Ser Pro Tyr Phe Asp Gly Trp Lys Ala Tyr Asp
            20                  25                  30

Arg Asp Pro Phe His Pro Ser Gln Asn Pro Asn Gly Val Ile Gln Met
        35                  40                  45

Gly Leu Ala Glu Asn Gln Leu Ser Ser Asp Leu Ile Glu Asp Trp Val
    50                  55                  60

Arg Ser Asn Pro Glu Ala Ser Ile Cys Thr Leu Glu Gly Val Gly Lys
65                  70                  75                  80
```

-continued

```
Phe Lys Asp Val Ala Asn Phe Gln Asp Tyr His Gly Leu Leu Glu Phe
                85                  90                  95
Arg His Ala Val Ala Lys Phe Met Ser Arg Gly Arg Gly Gly Lys Val
            100                 105                 110
Thr Phe Asp Pro Asp Arg Val Val Met Ser Gly Gly Ala Thr Gly Ala
        115                 120                 125
Asn Glu Leu Ile Val Phe Cys Leu Ala Asn Pro Gly Asp Ala Phe Leu
130                 135                 140
Leu Pro Ser Pro Tyr Tyr Pro Ala Asn Asp Arg Asp Leu Gln Trp Arg
145                 150                 155                 160
Thr Gly Ala Gln Ile Ile Pro Val His Cys Asn Ser Ser Asn Gly Phe
                165                 170                 175
Lys Ile Thr Arg Glu Ala Leu Glu Arg Ser Tyr Ala Gln Ala Gln Glu
            180                 185                 190
Ser Asn Ile Asn Val Lys Gly Val Leu Leu Thr Asn Pro Ser Asn Pro
        195                 200                 205
Leu Gly Thr Ile Leu Asp Arg Asp Thr Leu Lys Ser Ile Val Ser Phe
210                 215                 220
Val Thr Asp Asn Asn Ile His Leu Val Ile Asp Glu Ile Tyr Ala Ala
225                 230                 235                 240
Thr Val Phe Val Ala Pro Glu Phe Val Ser Val Ser Glu Ile Leu Gln
                245                 250                 255
Glu Met Asp Asp Thr Thr Cys Asn Pro Asp Leu Ile His Ile Val Tyr
            260                 265                 270
Ser Leu Ser Lys Asp Leu Gly Met Pro Gly Phe Arg Val Gly Ile Val
        275                 280                 285
Tyr Ser Phe Asn Asp Asp Val Val Ser Cys Ala Arg Lys Met Ser Ser
290                 295                 300
Phe Gly Leu Val Ser Thr Gln Thr Gln His Leu Leu Ala Ala Met Leu
305                 310                 315                 320
Ser Asp Asp Val Phe Val Glu Arg Phe Leu Ala Glu Arg Arg Arg Leu
                325                 330                 335
Gly Arg Arg His Gly Val Phe Thr Lys Gly Leu Glu Glu Leu Gly Ile
            340                 345                 350
Gly Cys Leu Lys Ser Asn Ala Gly Leu Tyr Phe Trp Met Asp Leu Arg
        355                 360                 365
Lys Leu Leu Glu Glu Glu Thr Phe Glu Ala Glu Met Val Leu Trp Lys
370                 375                 380
Val Ile Ile Asn Glu Val Lys Leu Asn Val Ser Pro Gly Ser Ser Phe
385                 390                 395                 400
His Cys Val Glu Pro Gly Trp Phe Arg Val Cys Phe Ala Asn Met Asp
                405                 410                 415
Asp Glu Thr Val His Val Ala Leu Lys Arg Ile Arg Ala Phe Val Arg
            420                 425                 430
Lys Lys Glu Val Gly Pro Val Lys Arg Lys Phe Met Asp Asn Leu
        435                 440                 445
Asn Leu Arg Leu Ser Phe Ser Ser Leu Arg Tyr Asp Glu Ser Val Met
450                 455                 460
Leu Ser Pro His Ile Met Val Ser Thr His Ser Pro Leu Val Arg Ala
465                 470                 475                 480
Arg Thr
```

```
<210> SEQ ID NO 18
<211> LENGTH: 485
<212> TYPE: PRT
<213> ORGANISM: Lycopersicum eculentum
<300> PUBLICATION INFORMATION:
<301> AUTHORS: Capitani, et al.
<303> JOURNAL: Journal of Molecular Biology
<304> VOLUME: 194
<306> PAGES: 745-756
<307> DATE: 1999

<400> SEQUENCE: 18

Met Val Ser Ile Ser Lys Asn Asn Gln Lys Gln Gln Leu Leu Ser Lys
1               5                   10                  15

Ile Ala Thr Asn Asp Gly His Gly Glu Asn Ser Pro Tyr Phe Asp Gly
            20                  25                  30

Trp Lys Ala Tyr Ala Asn Asn Pro Phe His Leu Thr Asp Asn Pro Thr
        35                  40                  45

Gly Val Ile Gln Met Gly Leu Ala Glu Asn Gln Leu Cys Phe Asp Leu
    50                  55                  60

Ile Gln Glu Trp Val Val Asn Pro Lys Ala Ser Ile Cys Thr Val
65                  70                  75                  80

Glu Gly Ala Glu Asn Phe Gln Asp Ile Ala Ile Phe Gln Asp Tyr His
                85                  90                  95

Gly Leu Pro Glu Phe Arg Gln Ala Val Ala Arg Phe Met Glu Lys Val
            100                 105                 110

Arg Gly Asp Arg Val Thr Phe Asp Pro Asn Arg Ile Val Met Ser Gly
        115                 120                 125

Gly Ala Thr Gly Ala His Glu Met Leu Ala Phe Cys Leu Ala Asp Pro
    130                 135                 140

Gly Asp Ala Phe Leu Val Pro Thr Pro Tyr Tyr Pro Gly Phe Asp Arg
145                 150                 155                 160

Asp Leu Arg Trp Arg Thr Gly Val Gln Leu Phe Pro Val Val Cys Glu
                165                 170                 175

Ser Cys Asn Asp Phe Lys Val Thr Thr Lys Ala Leu Glu Glu Ala Tyr
            180                 185                 190

Glu Lys Ala Gln Gln Ser Asn Ile Lys Ile Lys Gly Leu Leu Ile Asn
        195                 200                 205

Asn Pro Ser Asn Pro Leu Gly Thr Leu Leu Asp Lys Asp Thr Leu Arg
    210                 215                 220

Asp Ile Val Thr Phe Ile Asn Ser Lys Asn Ile His Leu Val Cys Asp
225                 230                 235                 240

Glu Ile Tyr Ala Ala Thr Val Phe Asp Gln Pro Arg Phe Ile Ser Val
                245                 250                 255

Ser Glu Ile Val Glu Asp Met Ile Glu Cys Asn Lys Asp Leu Ile His
            260                 265                 270

Ile Val Tyr Ser Leu Ser Lys Asp Leu Gly Phe Pro Gly Phe Arg Val
        275                 280                 285

Gly Ile Val Tyr Ser Tyr Asn Asp Thr Val Val Asn Ile Ala Arg Lys
    290                 295                 300

Met Ser Ser Phe Gly Leu Val Ser Ala Gln Thr Gln His Leu Leu Ala
305                 310                 315                 320

Ser Met Leu Ser Asp Glu Val Phe Ile Asp Lys Phe Ile Ala Glu Ser
                325                 330                 335

Ser Glu Arg Leu Gly Glu Arg Gln Gly Met Phe Thr Lys Gly Leu Ala
            340                 345                 350
```

Glu Val Gly Ile Ser Thr Leu Lys Ser Asn Ala Gly Leu Phe Phe Trp
            355                 360                 365

Met Asp Leu Arg Arg Leu Leu Lys Glu Ala Thr Phe Asp Ser Glu Leu
    370                 375                 380

Glu Leu Trp Arg Ile Ile Ile Asn Glu Val Lys Leu Asn Val Ser Pro
385                 390                 395                 400

Gly Cys Ser Phe His Cys Ser Glu Pro Gly Trp Phe Arg Val Cys Phe
                405                 410                 415

Ala Asn Met Asp Asp Glu Thr Met Arg Ile Ala Leu Lys Arg Ile Ser
            420                 425                 430

Tyr Phe Val Leu Gln Pro Lys Gly Leu Asn Asn Ile Ala Ala Ile Lys
        435                 440                 445

Lys Gln Cys Ser Arg Arg Lys Leu Gln Ile Ser Leu Ser Phe Arg Arg
    450                 455                 460

Leu Asp His Glu Phe Met Asn Ser Pro Ala His Ser Pro Met Asn Ser
465                 470                 475                 480

Pro Leu Val Arg Thr
            485

<210> SEQ ID NO 19
<211> LENGTH: 491
<212> TYPE: PRT
<213> ORGANISM: Brassica oleracea
<300> PUBLICATION INFORMATION:
<301> AUTHORS: Capitani, et al.
<303> JOURNAL: Journal of Molecular Biology
<304> VOLUME: 194
<306> PAGES: 745-756
<307> DATE: 1999

<400> SEQUENCE: 19

Met Val Ala Leu Thr Ala Glu Lys Gln Asp Gln Asn Leu Leu Ser Arg
1               5                   10                  15

Met Ala Ala Gly Asp Gly His Gly Glu Lys Ser Ala Tyr Phe Asp Gly
            20                  25                  30

Trp Lys Ala Tyr Glu Glu Asn Pro Phe His Pro Ile Asp Arg Pro Asp
        35                  40                  45

Gly Val Ile Gln Met Gly Leu Ala Glu Asn Gln Leu Cys Gly Asp Leu
    50                  55                  60

Met Arg Lys Trp Val Leu Glu His Pro Glu Ala Ser Ile Cys Thr Ala
65                  70                  75                  80

Glu Gly Val Asn Gln Phe Ser Asp Ile Ala Ile Phe Gln Asp Tyr His
            85                  90                  95

Gly Leu Pro Glu Phe Arg Gln Ala Val Ala Lys Phe Met Glu Lys Thr
            100                 105                 110

Arg Asn Asn Lys Val Lys Phe Asp Pro Asp Arg Ile Val Met Ser Gly
        115                 120                 125

Gly Ala Thr Gly Ala His Glu Thr Val Ala Phe Cys Leu Ala Asn Pro
    130                 135                 140

Gly Asp Gly Phe Leu Val Pro Thr Pro Tyr Tyr Pro Gly Phe Asp Arg
145                 150                 155                 160

Asp Leu Arg Trp Arg Thr Gly Val Asn Leu Val Pro Val Thr Cys His
            165                 170                 175

Ser Ser Asn Gly Phe Lys Ile Thr Ala Glu Ala Leu Asp Ala Ala Tyr
            180                 185                 190

Glu Asn Ala Arg Val Ser Asn Ile Pro Val Lys Gly Leu Leu Ile Thr
        195                 200                 205

-continued

Asn Pro Ser Asn Pro Leu Gly Thr Thr Leu Asp Arg Asp Cys Leu Lys
                210                 215                 220

Ser Leu Val Lys Phe Thr Asn Asp Lys Gly Ile His Leu Ile Ala Asp
225                 230                 235                 240

Glu Ile Tyr Ala Ala Thr Thr Phe Gly Glu Ser Glu Phe Ile Ser Val
                245                 250                 255

Ala Glu Val Ile Asp Glu Ile Pro Asp Cys Asn Thr Asp Leu Ile His
                260                 265                 270

Ile Val Tyr Ser Leu Ser Lys Asp Met Gly Leu Pro Gly Leu Arg Val
            275                 280                 285

Gly Ile Val Tyr Ser Tyr Asn Asp Arg Val Val Gln Ile Ala Arg Lys
            290                 295                 300

Met Ser Ser Phe Gly Leu Val Ser Ser Gln Thr Gln His Leu Ile Ala
305                 310                 315                 320

Lys Met Leu Ser Asp Glu Asp Phe Val Asp Glu Phe Ile Arg Lys Ser
                325                 330                 335

Lys Leu Arg Leu Ala Glu Arg His Ala Glu Leu Thr Thr Gly Leu Asp
                340                 345                 350

Gly Leu Ser Ile Gly Trp Leu Lys Ala Gly Ala Gly Leu Phe Ile Trp
            355                 360                 365

Met Asp Leu Arg Asn Leu Leu Lys Thr Ala Thr Phe Asp Ser Glu Met
370                 375                 380

Glu Leu Trp Arg Val Ile Val His Lys Val Lys Leu Asn Val Ser Pro
385                 390                 395                 400

Gly Gly Ser Cys His Cys His Glu Pro Gly Trp Phe Arg Val Cys Phe
                405                 410                 415

Ala Asn Met Asp Tyr Gln Thr Met Glu Thr Ala Leu Glu Arg Ile Arg
                420                 425                 430

Val Phe Thr Ser Gln Thr Glu Glu Ser Leu Ile Leu Thr Lys Pro
                435                 440                 445

Met Ala Lys Lys Lys Cys Trp Gln Ser Ser Leu Arg Leu Ser Phe
450                 455                 460

Lys Asp Thr Arg Arg Phe Glu Glu Gly Phe Phe Ser Pro His Ser Pro
465                 470                 475                 480

Val Pro Pro Ser Pro Leu Val Arg Ala Gln Ile
                485                 490

```
<210> SEQ ID NO 20
<211> LENGTH: 467
<212> TYPE: PRT
<213> ORGANISM: Phaseolus aureus
<300> PUBLICATION INFORMATION:
<301> AUTHORS: Capitani, et al.
<303> JOURNAL: Journal of Molecular Biology
<304> VOLUME: 194
<306> PAGES: 745-756
<307> DATE: 1999

<400> SEQUENCE: 20
```

Met Arg Leu Leu Ser Thr Ile Ala Thr Cys Asn Ser His Gly Gln Asp
1               5                   10                  15

Ser Ser Tyr Phe Leu Gly Trp Gln Glu Tyr Glu Lys Asn Pro Tyr Asp
                20                  25                  30

Glu Leu His Asn Pro Lys Gly Ile Ile Gln Met Gly Leu Ala Glu Asn
            35                  40                  45

Gln Leu Ser Phe Asp Leu Leu Glu Ser Trp Leu Ala Lys Asn Pro Asp

-continued

```
                50                  55                  60
Val Ala Gly Phe Lys Arg Asp Gly Lys Ser Ile Phe Arg Glu Leu Ala
 65                  70                  75                  80

Leu Phe Gln Asp Tyr His Gly Leu Pro Ser Phe Lys Lys Ala Leu Val
                 85                  90                  95

Asp Phe Met Ser Glu Ile Arg Gly Asn Lys Val Thr Phe Asp Pro Asn
                100                 105                 110

His Ile Val Leu Thr Ala Gly Ser Thr Ser Ala Asn Glu Thr Leu Met
                115                 120                 125

Phe Cys Leu Ala Glu Gln Gly Asp Ala Phe Leu Leu Pro Thr Pro Tyr
            130                 135                 140

Tyr Pro Gly Phe Asp Arg Asp Leu Lys Trp Arg Thr Gly Ala Glu Ile
145                 150                 155                 160

Val Pro Ile Gln Cys Thr Ser Ser Asn Phe Gln Ile Thr Glu Pro
                165                 170                 175

Ala Leu Lys Gln Ala Tyr Glu Glu Ala Arg Lys Arg Asn Leu Arg Val
            180                 185                 190

Lys Gly Leu Leu Val Thr Asn Pro Ser Asn Pro Leu Gly Thr Thr Met
            195                 200                 205

Ser Arg Ser Glu Leu Asn Leu Leu Val Asp Phe Ile Lys Glu Lys Lys
210                 215                 220

Asp Thr His Leu Ile Ser Asp Glu Ile Tyr Ser Gly Thr Val Phe Ser
225                 230                 235                 240

Ser Pro Gly Phe Val Ser Val Met Glu Ile Leu Lys Glu Arg Asn Asp
                245                 250                 255

Thr Glu Glu Ile Trp Asn Arg Val His Val Val Tyr Ser Leu Ser Lys
                260                 265                 270

Asp Leu Gly Leu Pro Gly Phe Arg Val Gly Ala Ile Tyr Ser Glu Asn
            275                 280                 285

Asp Thr Val Val Ala Ala Thr Lys Met Ser Ser Phe Gly Leu Val
            290                 295                 300

Ser Ser Gln Thr Gln Tyr Leu Leu Ser Ala Met Leu Gly Asp Lys Lys
305                 310                 315                 320

Phe Ala Arg Asn Tyr Ile Val Glu Asn Gln Lys Arg Leu Lys Arg Arg
                325                 330                 335

Gln Arg Met Met Val Ser Gly Leu Gln Lys Ala Gly Ile Ser Cys Leu
                340                 345                 350

Glu Ser Asn Ala Gly Leu Phe Cys Trp Val Asp Met Arg His Leu Leu
            355                 360                 365

His Ser Asn Thr Phe Glu Ala Glu Met Glu Leu Trp Lys Lys Ile Val
            370                 375                 380

Tyr Gln Val Gly Leu Asn Ile Ser Pro Gly Ser Ser Cys His Cys Thr
385                 390                 395                 400

Glu Pro Gly Trp Phe Arg Val Cys Phe Ala Asn Met Ser Glu Thr
                405                 410                 415

Leu Thr Leu Ala Met Lys Arg Leu Lys Asn Phe Val Val Glu Ser Thr
            420                 425                 430

Cys Thr Gln Arg Ser Ala Leu Phe Asn Gly Thr Ser Lys Arg Lys Ser
            435                 440                 445

Leu Thr Lys Trp Val Phe Arg Leu Ser Ser Arg Asp His Arg Glu Gln
    450                 455                 460

Glu Glu Arg
465
```

```
<210> SEQ ID NO 21
<211> LENGTH: 465
<212> TYPE: PRT
<213> ORGANISM: Solanum tuberosum
<300> PUBLICATION INFORMATION:
<301> AUTHORS: Capitani, et al.
<303> JOURNAL: Journal of Molecular Biology
<304> VOLUME: 194
<306> PAGES: 745-756
<307> DATE: 1999

<400> SEQUENCE: 21
```

Met Lys Leu Leu Ser Lys Lys Ala Met Cys Asn Ser His Gly Gln Asp
1               5                   10                  15

Ser Ser Tyr Phe Leu Gly Trp Glu Glu Tyr Glu Lys Asn Pro Tyr Asp
            20                  25                  30

Glu Thr Arg Asn Pro Lys Gly Ile Ile Gln Met Gly Leu Ala Glu Asn
        35                  40                  45

Gln Leu Ser Phe Asp Leu Leu Glu Ser Trp Leu Thr Gln Asn Pro Asp
50                  55                  60

Ala Ala Ala Phe Lys Arg Asn Gly Asp Ser Ile Phe Arg Asp Leu Ala
65                  70                  75                  80

Leu Phe Gln Asp Tyr His Gly Leu Pro Ala Phe Lys Asp Ala Leu Val
                85                  90                  95

Gln Phe Met Ser Glu Ile Arg Gly Asn Lys Val Ser Phe Asp Ser Asn
            100                 105                 110

Lys Leu Val Leu Thr Ala Gly Ala Thr Ser Ala Asn Glu Thr Leu Met
        115                 120                 125

Phe Cys Leu Ala Asp Pro Gly Asp Ala Phe Leu Leu Pro Thr Pro Tyr
130                 135                 140

Tyr Pro Gly Phe Asp Arg Asp Leu Lys Trp Arg Thr Gly Ala Glu Ile
145                 150                 155                 160

Val Pro Ile Gln Cys Thr Ser Ser Asn Gly Phe Arg Ile Thr Glu Ser
                165                 170                 175

Ala Leu Glu Glu Ala Tyr Lys Glu Ala Glu Arg Arg Asn Leu Arg Val
            180                 185                 190

Lys Gly Val Leu Val Thr Asn Pro Ser Asn Pro Leu Gly Thr Thr Leu
        195                 200                 205

Thr Lys Lys Glu Leu Gln Leu Leu Thr Phe Val Ser Thr Lys Gln
210                 215                 220

Ile His Leu Ile Ser Asp Glu Ile Tyr Ser Gly Thr Val Phe Asn Ser
225                 230                 235                 240

Pro Lys Phe Val Ser Val Met Glu Val Leu Ile Glu Asn Asn Tyr Met
                245                 250                 255

Tyr Thr Glu Val Trp Asp Arg Val His Ile Val Tyr Ser Leu Ser Lys
            260                 265                 270

Asp Leu Gly Leu Pro Gly Phe Arg Val Gly Ala Ile Tyr Ser Asn Asp
        275                 280                 285

Val Met Ile Val Ser Ala Ala Thr Lys Met Ser Ser Phe Gly Leu Ile
290                 295                 300

Ser Ser Gln Thr Gln Tyr Leu Leu Ser Ala Leu Ser Asp Lys Lys
305                 310                 315                 320

Phe Thr Lys Lys Tyr Val Ser Glu Asn Gln Lys Arg Leu Lys Lys Arg
                325                 330                 335

His Glu Met Leu Val Gly Gly Leu Lys Gln Ile Gly Ile Arg Cys Leu

-continued

```
                    340                 345                 350
Glu Ser Asn Ala Gly Leu Phe Cys Trp Val Asp Met Arg His Leu Leu
        355                 360                 365

Ser Ser Asn Thr Phe Asp Gly Glu Met Glu Leu Trp Lys Lys Ile Val
    370                 375                 380

Tyr Glu Val Gly Leu Asn Ile Ser Pro Gly Ser Ser Cys His Cys Thr
385                 390                 395                 400

Glu Pro Gly Trp Phe Arg Ala Cys Phe Ala Asn Met Ser Glu Asp Thr
                405                 410                 415

Leu Asn Ile Ala Ile Gln Arg Leu Lys Ala Phe Val Asp Ser Arg Asp
                420                 425                 430

Asn Lys Asp Asp Ile Gln Asn Gln Lys His Ser Asn Lys Lys Lys Ser
        435                 440                 445

Phe Ser Lys Trp Val Phe Arg Leu Ser Phe Asn Glu Arg Gln Arg Glu
        450                 455                 460

Arg
465
```